United States Patent

Sueda et al.

Patent Number: 5,621,010
Date of Patent: Apr. 15, 1997

[54] UREA DERIVATIVES AND THEIR USE AS ACAT INHIBITORS

[75] Inventors: Noriyoshi Sueda, Saitama-ken; Kazuhiko Yamada, Komoro; Makoto Yanai, Saitama-ken; Katsutoshi Miura, Saitama-ken; Masato Horigome, Saitama-ken; Norio Oshida, Saitama-ken; Shigeru Hiramoto, Saitama-ken; Koichi Katsuyama, Saitama-ken; Fumihisa Nakata, Saitama-ken; Nobuhiro Kinoshita, Saitama-ken; Yoko Tsukada, Saitama-ken, all of Japan

[73] Assignee: Nisshin Flour Milling Co., Ltd., Tokyo, Japan

[21] Appl. No.: 245,013

[22] Filed: May 18, 1994

[30] Foreign Application Priority Data

May 21, 1993 [JP] Japan ..................... 5-119786
Oct. 21, 1993 [JP] Japan ..................... 5-285525
Feb. 4, 1994 [JP] Japan ..................... 6-032040

[51] Int. Cl.$^6$ ............ A61K 31/17; C07C 273/00; C07D 249/08; C07D 217/12
[52] U.S. Cl. ............ 514/596; 514/597; 514/598; 514/824; 546/146; 546/332; 546/275.4; 546/272.7; 548/178; 548/262.8; 548/356.1; 564/48; 564/50; 564/52; 564/53; 564/54; 544/360; 544/371; 544/372
[58] Field of Search ............ 564/48, 50, 52, 564/53, 54; 546/146, 332; 548/178, 202.8, 378; 514/596, 597, 598, 824

[56] References Cited

U.S. PATENT DOCUMENTS 5,290,814  3/1994  Jackson et al. ............ 514/596
5,422,373  6/1995  Franzmann ............ 514/598

FOREIGN PATENT DOCUMENTS 2115349   3/1993   Canada .
0344425  12/1989   European Pat. Off. .
0370740   5/1990   European Pat. Off. .
0450660  10/1991   European Pat. Off. .
 047778   4/1992   European Pat. Off. .
0477778   4/1992   European Pat. Off. .

OTHER PUBLICATIONS

Arterioschlerosis 4, 357–364 (1984), Morel, D.W., et al.
Proc. Natl. Acad. Sci., 84, 5928–5931 (1987) Kita, T., et al.
J. Lipid Resch. 30, 681–690 (1989), Largis, E.E., et al.
Japan J. Pharm., 42, 5127–523 (1986) Natori, K., et al.
J. Med. Chem., 34, 298–302 (1991), Mao, S.J.T., et al.

*Primary Examiner*—C. Warren Ivy
*Assistant Examiner*—Raymond Covington
*Attorney, Agent, or Firm*—Michael N. Meller

[57] ABSTRACT

Urea derivatives of formula (I)

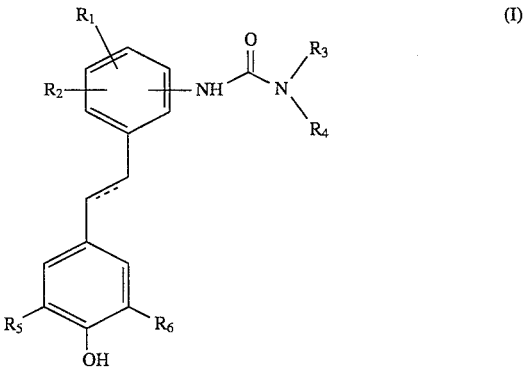

wherein the valuable groups are as defined in the specification, which possess both an ACAT inhibitory activity and an antioxidative activity. Those derivatives are useful in the prophylaxis and treatment of hypercholesterolemia and atherosclerosis.

8 Claims, No Drawings

UREA DERIVATIVES AND THEIR USE AS ACAT INHIBITORS

FIELD OF THE INVENTION

This invention relates to new urea derivatives, processes for their preparation and their use in medicine. More particularly, the invention relates to compounds having an inhibitory activity against an acyl coenzyme A cholesterol acyltransferase (called hereafter ACAT) and having a protective ability against an oxidative modification of low density lipoprotein (called hereafter LDL).

BACKGROUND OF THE INVENTION

In recent years, an interest has been directed to the relationship between an increase in the level of cholesterol in the serum and a human health condition. It has been pointed out that the level of cholesterol in the serum is associated with the amount of cholesterol deposited in the blood vessel system and the deposition of cholesterol in the blood vessel system brings about e.g. lesion of coronary artery, which is responsible for ischemic heart disease.

Drugs for reducing the level of cholesterol in the serum have been developed. These drugs, however, were effective in controlling blood cholesterol to an appropriate level, but ineffective in inhibiting absorption of cholesterol from the digestive tracts and deposition of cholesterol on the wall of blood vessels.

ACAT is an enzyme that catalyzes the synthesis of cholesteryl esters from acyl coenzyme A and cholesterol and plays an important role in metabolism of cholesterol and its absorption from the digestive tracts. It is believed that ACAT occurs in the site of mucosa cells of the intestinal tracts and is active in esterification and incorporation of cholesterol derived from the diet. On the other hand, the cholesterol deposited on the wall of blood vessels is the esterified cholesterol. The cholesterol accumulated in the foam cells which plays in important role in the formation of atherosclerosis lesion is also esterified cholesterol. The enzyme that catalyzes the esterification of cholesterol in these sites is also ACAT.

Accordingly, the inhibition of an ACAT activity can result in inhibiting the incorporation in vivo of cholesterol derived from the diet and further the formation of cholesteryl ester in specified cell sites.

Compounds having an ACAT inhibitory activity are disclosed in EP 0450660 A1 and EP 0477778 A2. However, those known compounds have only an ACAT inhibitory activity and give no effect on the oxidative modification of LDL causing the foam cell transformation of macrophage which is an important phenomenon for the formation of atherosclerosis lesion.

The foam cells which play an important role in the formation of atherosclerosis lesion are a product of uptake of oxidatively modified LDL into macrophage which results in the foam cell transformation of the macrophage. It is reported by Diane W. Morel et al. (Atheroma, Vol. 4, pages 357–364, 1984) that, the oxidatively modified LDL causes foam cell transformation of macrophage and plays an important role in the formation of atherosclerosis lesion. A report of TORU KITA et al. (Proc. Natl. Acad. Sci. U.S.A., Vol. 84, pages 5928–5931, 1987) demonstrates that prevention of the oxidative modification of LDL induces regression of the atherosclerosis lesion. Therefore, inhibition of the oxidative modification of LDL, in addition to the abovementioned ACAT inhibitory activity, is very important in preventing the formation and progression as well as inducing regression of atherosclerosis lesion.

Under such circumstances, it has been desired to develop the compound having an ACAT inhibitory activity and being capable of inhibiting an oxidative modification of LDL or the like, since such compound may decrease the serum cholesterol level and inhibit the oxidative modification of LDL cholesterol deposited on the blood vessel or tissue, thus being effective for inhibiting the formation and progression of atherosclerosis lesions and inducing its regression.

DETAILED DESCRIPTION OF THE INVENTION

We have now found new urea derivatives which exhibit both an ACAT inhibitory activity and an antioxidative activity. The urea derivatives of the present invention possess an ACAT inhibitory activity, thereby inhibiting an absorption of cholesterol from the intestinal tracts, lowering a blood cholesterol level and inhibiting an accumulation of cholesteryl esters in the wall of blood vessels, atheroma and macrophage, and simultaneously an antioxidative activity i.e. a protective activity against the oxidative modification of LDL which participates in foam cell transformation of macrophage thereby effectively inhibiting the formation and progression of atherosclerosis lesion and inducing its regression.

According to one aspect of the present invention, there is provided a compound of formula (I) and pharmaceutically acceptable salts thereof, which exhibits both an ACAT inhibitory activity and an antioxidative activity.

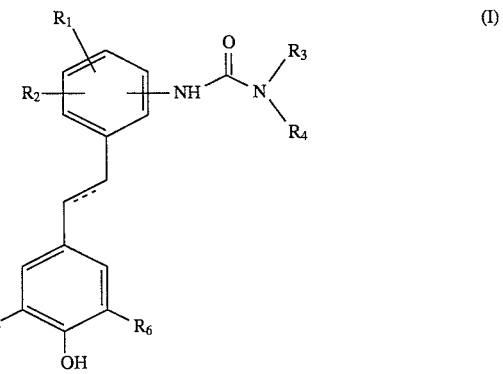

in which:
and $R_2$, which may be the same or different, each represents
  a hydrogen atom,
  a halogen atom,
  a straight or branched $(C_1-C_6)$alkyl group or
  a straight or branched $(C_1-C_6)$alkoxy group, $R_3$ and $R_4$, which may be the same or different, each represents
  a hydrogen atom,
  a straight or branched $(C_1-C_{12})$alkyl group,
  a straight or branched $(C_2-C_{20})$alkenyl group,
  a $(C_1-C_6)$alkoxy$(C_1-C_6)$alkyl group,
  a $(C_1-C_6)$alkoxycarbonyl$(C_1-C_9)$alkyl group,
  a benzyloxycarbonyl$(C_1-C_6)$alkyl group in which the alkyl moiety is optionally substituted by phenyl,
  a N,N-di$(C_1-C_6)$alkylamino$(C_1-C_6)$alkyl group,
  a N-$(C_1-C_6)$alkyl-N-benzylamino$(C_1-C_6)$alkyl group, a $(C_1-C_6)$alkylthio$(C_1-C_6)$alkyl group,
an oxo $(C_1-C_9)$alkyl group,
a hydroxy$(C_1-C_6)$alkyl group,
a dihydroxy$(C_1-C_6)$alkyl group,
a cyclo$(C_3-C_{15})$alkyl group,
a cyclo$(C_3-C_8)$alkyl$(C_1-C_6)$alkyl group,
a dicyclo$(C_3-C_9)$alkyl$(C_1-C_6)$alkyl group,
a bicyclo$(C_6-C_9)$alkyl group,
a tricyclo$(C_9-C_{12})$alkyl group,
  in which in all cases the cycloalkyl group or the cycloalkyl moiety is optionally substituted by one or two substituents selected from the group consisting of $(C_1-C_6)$alkyl, hydroxy, amino, acetoxy, acetamido, phenyl, benzyloxy, dimethylaminophenyl, and methylenedioxyphenyl, which may be further fused with a benzene ring,
an aryl group,
an aryl$(C_1-C_6)$alkyl group,
a diaryl$(C_1-C_6)$alkyl group,
  in which in all cases the aryl group or the aryl moiety is optionally substituted by one, two or three substituents selected from the group consisting of $(C_1-C_6)$alkyl, $(C_1-C_6)$alkyloxy, halogen, nitro, hydroxy, amino, dimethylamino, methylenedioxy, and pyrrolidinyl,
a heterocyclic group or
a heterocyclic group attached to a $(C_1-C_6)$alkylene chain,
  in which in all cases the heterocyclic group represents a saturated or unsaturated, 5 to 8 membered ring monocyclic or bicyclic, heterocyclic group containing 1 to 3 heteroatoms selected from the group consisting of S, O and N, and the heterocyclic group is optionally substituted by one or two substituents selected from the group consisting of acetyl, hydroxy, $(C_1-C_9)$alkyl, $(C_1-C_9)$alkyloxy, cyclo$(C_3-C_8)$alkyl, cyclo$(C_3-C_8)$alkyl$(C_3-C_{10})$alkyl, pyridyl$(C_1-C_6)$alkyl, phenyl, phenyl$(C_1-C_6)$alkyl, diphenyl$(C_1-C_6)$alkyl, and phenylpiperazinyl, the phenyl group or the phenyl moiety being optionally substituted by one or two substituents selected from the group consisting of halogen, hydroxy, $(C_1-C_6)$alkyl, $(C_1-C_6)$alkoxy, cyano, diethylamino and trifluoromethyl,
  which may be further fused with a benzene ring,
and further $R_3$ and $R_4$, together with the nitrogen atom to which they are attached, may form a saturated or unsaturated heterocyclic group,
  in which the heterocyclic group represents a 5 to 8 membered ring monocyclic or bicyclic, heterocyclic group or a group derived from a heterocyclic spiro compound, which may contain one or two heteroatoms selected from the group consisting of S, O or N, the heterocyclic group being optionally substituted by one or two substituents selected from the group consisting of $(C_1-C_6)$alkyl, hydroxy, hydroxy$(C_1-C_6)$alkyl, $(C_1-C_6)$alkoxy$(C_1-C_6)$alkyl, acetoxy$(C_1-C_6)$alkyl, $(C_1-C_9)$alkylcarbonyl, $(C_1-C_6)$alkoxycarbonyl, amino, tosyl, phenyl, halogenophenyl, $(C_1-C_6)$alkoxyphenyl, phenyl$(C_1-C_6)$alkyl, benzyloxy, benzyloxy$(C_1-C_6)$alkyl, tolyl, xylyl, benzoyl, methylenedioxyphenyl $(C_1-C_6)$alkyl, pyridyl, pyridylcarbonyl, piperidyl, pyrrolidinyl$(C_1-C_6)$alkyl and pyrrolidinylcarbonyl$(C_1-C_6)$alkyl, which may be further fused with a benzene ring,
  in which in all cases the alkyl and alkoxy moieties may be either straight or branched, with the proviso that both $R_3$ and $R_4$ do not represent a hydrogen atom at the same time;

$R_5$ and $R_6$, which may be the same or different, each represents a straight or branched $(C_1-C_6)$alkyl group; and the line

represents —$CH_2CH_2$— or —$CH=CH$—.

Referring to $R_1$ and $R_2$ in formula (I), the halogen atom includes fluorine, chlorine, bromine and iodine, the $(C_1-C_6)$alkoxy group includes e.g. methoxy, ethoxy, propoxy, isopropoxy, butoxy, isobutoxy, sec-butoxy, tert-butoxy, pentyloxy and hexyloxy, and the $(C_1-C_6)$alkyl group includes e.g. methyl, ethyl, propyl, isopropyl, butyl, isobutyl, tert-butyl, pentyl and hexyl.

Referring to $R_3$ and $R_4$ in formula (I), the $(C_1-C_{12})$alkyl group includes e.g. methyl, ethyl, propyl, isopropyl, butyl, isobutyl, sec-butyl, tert-butyl, pentyl, isopentyl, neopentyl, hexyl, isohexyl, heptyl, octyl, trimethylpentyl, 2,4,4-trimethyl-2-pentyl, nonyl, decyl and dodecyl. The $(C_2-C_{20})$alkenyl group includes e.g. vinyl, allyl, isopropenyl, 2-butenyl, 2-pentenyl, 4-pentenyl, 3-hexenyl, 5-hexenyl, 4-octenyl, 7-octenyl, 7-decenyl, 3,7-dimethyl-2,6-octadienyl, 10-tetradecenyl, 8-heptadecenyl, 8-octadecenyl and 4,7,10,13,16-nonadecapentaenyl. The $(C_1-C_6)$alkoxy$(C_1-C_6)$alkyl group includes e.g. 2-methoxyethyl, 4-methoxybutyl, 2-methoxybutyl, 6-methoxyhexyl, ethoxymethyl, 3-ethoxypropyl, 2-propoxyethyl, 5-propoxypentyl, isopropoxymethyl, butoxymethyl, 2-isobutoxyethyl, sec-butoxymethyl, tert-butoxymethyl, pentyloxymethyl, 2-pentyloxyethyl and hexyloxymethyl.

The $(C_1-C_6)$alkoxycarbonyl$(C_1-C_9)$alkyl group includes e.g. 2-(methoxycarbonyl)ethyl, 7-(methoxycarbonyl)heptyl, 2-(ethoxycarbonyl)ethyl, 4-(ethoxycarbonyl)butyl, propoxycarbonylmethyl, 3-(propoxycarbonyl)butyl, isopropoxycarbonylmethyl, butoxycarbonylmethyl, 1-(butoxycarbonyl)ethyl, 2-(isobutoxycarbonyl)ethyl, sec-butoxycarbonylmethyl, 2-(tert-butoxycarbonyl)ethyl, pentyloxycarbonylmethyl and 2-(hexyloxycarbonyl)ethyl, α-(methoxycarbonyl)benzyl, α-(ethoxycarbonyl)benzyl.

The benzyloxycarbonyl$(C_1-C_6)$alkyl group includes benzyloxycarbonylmethyl, 2-(benzyloxycarbonyl)ethyl, 6-(benzyloxycarbonyl)hexyl, 4-(benzyloxycarbonyl)butyl and α-(benzyloxycarbonyl)benzyl.

The N,N-di$(C_1-C_6)$alkylamino$(C_1-C_6)$alkyl group includes e.g. 2-(N,N-dimethylamino)ethyl, 4-(N,N-dimethylamino)butyl, 2-(N,N-diethylamino)ethyl, 3-(N,N-diethylamino)propyl, N,N-diisopropylaminomethyl, N,N-dibutylaminomethyl, 2-(N,N-dibutylamino)ethyl, 2-(N,N-diisobutylamino)ethyl, N,N-dipentylaminomethyl, 2-(N,N-dihexylamino)ethyl and N,N-diisohexylaminomethyl.

The N-$(C_1-C_6)$alkyl-N-benzylamino$(C_1-C_6)$alkyl includes e.g. 2-(N-benzyl-N-methylamino)ethyl, 2-(N-benzyl-N-ethylamino)ethyl, 4-(N-benzyl-N-methylamino)butyl, 2-(N-benzyl-N-ethylamino)ethyl and 3-(N-benzyl-N-ethylamino)propyl.

The $(C_1-C_6)$alkylthio$(C_1-C_6)$alkyl group includes e.g. 2-(methylthio)ethyl, 2-(ethylthio)ethyl, propylthiomethyl, 2-(isopropylthio)ethyl, 1-(butylthio)ethyl, isobutylthiomethyl, tert-butylthiomethyl, pentylthiomethyl and hexylthiomethyl.

The oxo$(C_1-C_9)$alkyl group includes e.g. 2-oxopropyl, 2-oxobutyl, 4-oxopentyl, 6-oxoheptyl and 2-oxooctyl.

The hydroxy($C_1$–$C_6$)alkyl group includes e.g. 2-hydroxyethyl, 2-hydroxypropyl, 3-hydroxypropyl, 3-hydroxybutyl and 6-hydroxyhexyl.

The dihydroxy($C_1$–$C_6$)alkyl group includes e.g. 2,3-dihydroxypropyl, 4,5-dihydroxypentyl, 1,5-dihydroxy-3-pentyl, 2-ethyl-1,3-dihydroxy-2-propyl, and 2,4-dihydroxy-3-methylpentyl.

The cyclo($C_3$–$C_{15}$)alkyl group includes e.g. cyclopropyl, cyclobutyl, cyclopentyl, cyclohexyl, cycloheptyl, cyclooctyl, cyclodecyl, cyclododecyl, 1-phenylcyclopentyl, 4-(benzyloxy)cyclohexyl, 4-aminocyclohexyl, 4-acetamidocyclohexyl, 4-hydroxycyclohexyl, 4-acetoxycyclohexyl, 4-tert-butylcyclohexyl, 2,3-dimethylcyclohexyl, 1,2,3,4-tetrahydronaphthyl, cyclododecyl and benzyloxycyclohexyl.

The cyclo($C_3$–$C_8$)alkyl($C_1$–$C_8$)alkyl group includes e.g. cyclopropylmethyl, 2-cyclobutylethyl, 2-cycloheptylethyl, cyclohexylmethyl, 3-cyclohexylpropyl, 4-cyclohexylbutyl, cyclooctylmethyl, 5-cyclooctylpentyl, 1-(4-dimethylaminophenyl)cyclopentylmethyl and 1-(3,4-methylenedioxyphenyl)cyclopentylmethyl.

The dicyclo($C_3$–$C_9$)alkyl($C_1$–$C_6$)alkyl group includes e.g. dicyclohexylmethyl, 2,2-dicyclohexylethyl and 3,3-dicyclohexylpropyl.

The bicyclo($C_6$–$C_9$)alkyl group includes e.g. bicyclo[3.3.0]-2-octyl, bicyclo[3.3.1]-2-nonyl and bicyclo[3.2.1]-2-octyl.

The tricyclo($C_9$–$C_{12}$)alkyl group includes e.g. tricyclo[5.2.1.0$^{2.6}$]decyl and tricyclo[3.3.1.1$^{3.7}$]decyl.

The aryl group includes e.g. phenyl, 1-naphthyl, 2-naphthyl, 3-naphthyl, 4-methylphenyl, 2,6-diisopropylphenyl, 3,5-di-tert-butyl-4-hydroxyphenyl, 2-methoxyphenyl, 4-hexyloxyphenyl, 4-fluorophenyl, 2-nitrophenyl, 4-chloronaphthyl, 3-amino-2-naphthyl, 5-hydroxynaphthyl, 5-methoxynaphthyl and anthryl.

The aryl($C_1$–$C_6$)alkyl group includes e.g. benzyl, phenethyl, α-methylbenzyl, 3-phenylpropyl, 4-phenylbutyl, 9-anthrylmethyl, 4-ethylbenzyl, 4-ethoxybenzyl, 4-fluorobenzyl, 3,4-methylenedioxybenzyl, 3,4,5-trimethoxybenzyl, 4-methylphenethyl, 2-methoxyphenethyl, 4-methoxyphenethyl, 3,4-dimethoxyphenethyl, 3-chlorophenethyl, 4-chlorophenethyl, 4-fluorophenethyl, 4-nitrophenethyl, 3,4,5-trimethoxyphenethyl, 4-nitrophenylbutyl, 1-(4-fluorophenyl)-2-methylpropyl, 3-(3,4-dichlorophenyl)propyl, 4-dimethylaminophenethyl, 2-(3,4-dichlorophenyl)-2-propyl, 2-(3,4-dichlorophenyl)-2-methylpropyl, 2-(2-fluorophenyl)-2-methylpropyl, 2-(3-fluorophenyl)-2-methylpropyl, 2-(4-fluorophenyl)-2-methylpropyl and 2-[4-(1-pyrrolidinyl)phenyl]-2-methylpropyl.

The diaryl($C_1$–$C_6$)alkyl group includes e.g. diphenylmethyl, 1,2-diphenylethyl, 2,2-diphenylethyl, 4,4-diphenylbutyl and 6,6-diphenylhexyl.

The monocyclic, heterocyclic group includes e.g. 3-furyl, 2-thienyl, 3-pyrrolyl, 2-pyrrolidinyl, 2H-pyran-3-yl, 2-pyridyl, 4-piperidyl, 3-morpholinyl, 2-piperazinyl, 1-methyl-4-piperidyl, 1-benzyl-4-piperidyl, 1-methyl-3-piperidyl, 1-(2,4-difluorobenzyl)-4-piperidyl, 1-(3,4-difluorobenzyl)-4-piperidyl, 1-(3,5-difluorobenzyl)-4-piperidyl, 1-[2,4-bis-(trifluoromethyl)benzyl]-4-piperidyl, 1-(4-methoxybenzyl)-4-piperidyl, 1-phenethyl-4-piperidyl, 1-(2-fluorobenzyl)-4-piperidyl, 1-(3-fluorobenzyl)-4-piperidyl, 1-(4-fluorobenzyl)-4-piperidyl, 1-(4-chlorobenzyl)-4-piperidyl, 1-(4-cyanobenzyl)-4-piperidyl, 1-(2-pyridylmethyl)-4-piperidyl, 1-(3-pyridylmethyl)-4-piperidyl, 1-(4-pyridylmethyl)-4-piperidyl, 1-[4-(N, N-diethylamino)benzyl]-4-piperidyl, 1-[bis(4-fluorophenyl)methyl]-4-piperidyl, 1-(4-fluorophenethyl)-4-piperidyl, 1-(2,4-dimethylbenzyl)-4-piperidyl, 1-acetyl-4-piperidyl, 1-(4-hydroxybenzyl)-4-piperidyl, 1-(3,4-dihydroxybenzyl)-4-piperidyl, 1-ethyl-4-piperidyl, 1-neopentyl-4-piperidyl, 1-cyclohexyl-4-piperidyl, 1-heptyl-4-piperidyl, 1-(2-propyl)-4-piperidyl, 1-benzyl-3-piperidyl, 2-phenyl-3-piperidyl, 1-cyclohexylmethyl-3-piperidyl, 1-benzyl-3-pyrrolidinyl, 2-methoxy-5-pyridyl, 2-(4-phenyl-1-piperazinyl)-5-pyridyl and 5,6-dimethyl-1,2,4-triazin-3-yl.

The bicyclic, heterocyclic group includes e.g. 3-indolyl, 5-indazolyl, 2-quinolyl, 5-isoquinolyl, 2,4-dimethyl-1,8-naphthyridin-7-yl, 3,9-dimethyl-3,9-diazabicyclo[3.3.1]-7-nonyl, 9-methyl-3-oxa-9-azabicyclo[3.3.1]-7-nonyl, 9-(4-fluorobenzyl)-3-oxa-9-azabicyclo[3.3.1]-7-nonyl, 9-methyl-3-thia-9-azabicyclo[3.3.1]-7-nonyl, 8-methyl-8-azabicyclo[3.2.1]-3-octyl and 1-azabicyclo[2.2.2]-3-octyl.

The heterocyclic group attached to an alkylene chain may be the above-mentioned monocyclic or bicyclic heterocyclic group attached to an alkylene chain, which includes e.g. 3-furylmethyl, 3-(2-thienyl)propyl, 2-(3-indolyl)ethyl, 2-(3-pyrrolyl)ethyl, 2-pyrrolidinylmethyl, 2-pyridylmethyl, 3-pyridylmethyl, 4-pyridylmethyl, 2-(2-pyridyl)ethyl, 2-(4-piperidyl)ethyl, 3-(3-morpholinyl)propyl, 3-indolylmethyl, 2-(5-indazolyl)ethyl, 2-quinolylmethyl, 3-(1-imidazolyl)propyl, 2-morpholinoethyl, 3-morpholinopropyl, 3-(2-methylpiperidyl)propyl, 2-(1-pyrrolidinyl)ethyl, [4-(4-fluorobenzyl)-3-morpholinyl]methyl and (1-benzyl-4-hydroxy-4-piperidyl)methyl.

When $R_3$ and $R_4$ in formula (I), together with the nitrogen atom to which they are attached form the heterocyclic ring, the monocyclic, heterocyclic group includes e.g. pyrrolidinyl, 2,5-dimethyl-1-pyrrolidinyl, 3-hydroxy-1-pyrrolidinyl, 2-hydroxymethyl-1-pyrrolidinyl, 2-hydroxyethyl-1-pyrrolidinyl, 2-methoxymethyl-1-pyrrolidinyl, 2-(1-pyrrolidinylmethyl)pyrrolidinyl, 3-pyrrolin-1-yl, 2,5-dimethyl-3-pyrrolin-1-yl, piperidino, 2-methylpiperidino, 2-ethylpiperidino, 3-methylpiperidino, 4-methylpiperidino, 4-piperidinopiperidino, 3,3-dimethylpiperidino, 2,6-dimethylpiperidino, 3,5-dimethylpiperidino, 2,4-dimethylpiperidino, 2-(hydroxymethyl)piperidino, 2-(2-hydroxyethyl)piperidino, 2-(2-acetoxyethyl)piperidino, 3-hydroxypiperidino, 4-hydroxypiperidino, 4-oxopiperidino, 4-aminopiperidino, 4-benzylpiperidino, 2-[2-(benzyloxy)ethyl]piperidino, 3-(benzyloxy)piperidino, 1,2,3,6-tetrahydropyridyl, perhydroazepinyl, perhydroazocinyl, piperazinyl, 4-methyl-1-piperazinyl, 3-methyl-1-piperazinyl, 3,5-dimethyl-1-piperazinyl, 2,5-dimethyl-1-piperazinyl, 4-(2-hydroxyethyl)-1-piperazinyl, 4-pentanoyl-1-piperazinyl, 4-acetyl-1-piperazinyl, 4-p-toluenesulfonyl-1-piperazinyl, 4-benzyl-1-piperazinyl, 4-(3,4-methylenedioxybenzyl)-1-piperazinyl, 4-(2-pyridyl)-1-piperazinyl, 4-nicotinoyl-1-piperazinyl, 4-(1-pyrrolidinylcarbonylmethyl)-1-piperazinyl, 4-benzyl-1-piperidyl, 4-phenyl-1-piperidyl, 4-phenyl-1,2,3,6-tetrahydropyridyl, 4-phenyl-1-piperazinyl, 4-benzyl-1-piperazinyl, 4-(o-tolyl)-1-piperazinyl, 4-(2-fluorophenyl)-1-piperazinyl, 4-(2,3-xylyl)-1-piperazinyl, 4-(2-chlorophenyl)-1-piperazinyl, 4-(2-methoxyphenyl)-1-piperazinyl, 4-(2-ethoxyphenyl)-1-piperazinyl, 4-(m-tolyl)-1-piperazinyl, 4-(3,4-difluorophenyl)-1-piperazinyl, 4-(4-chlorophenyl)-1-piperazinyl, 4-(3,4-dimethoxyphenyl)-1-piperazinyl, homopiperazinyl, morpholino, 2,6-dimethylmorpholino, thiazolidinyl, thiomorpholino, pyrrolyl, 2-ethyl-1-pyrrolyl, 2,5-dimethyl-1-pyrrolyl, pyrazolyl, 3-methyl-1-pyrazolyl, 4-methyl-1-pyrazolyl, imidazolyl, 4-methyl-1-imidazolyl, 4-phenyl-1-imidazolyl, 1H-1,2,3-triazol-1-yl, 1,2,4-triazol-1-yl, imidazolidinyl, 2-imidazolin-1-yl, pyrazolidinyl and 2-pyrazolin-1-yl.

The bicyclic, heterocyclic group includes e.g. 4,5,6,7-tetrahydroindol-1-yl, 1,5,6,7-tetrahydro-4-oxoindol-1-yl, indolinyl, isoindolinyl, perhydroindol-1-yl, decahydroquinolinyl, perhydroisoquinolin-2-yl, 1,2,3,4-tetrahydrocarbazol-1-yl, 1,2,3,4-tetrahydroquinolin-1-yl, 1,2,3,4-tetrahydroisoquinolin-1-yl, 6,7-dimethoxy-1,2,3,4-tetrahydroisoquinolin-2-yl, 5H-dibenz[b,f]azepin-5-yl, 10,11-dihydro-5H-dibenz[b,f]azepin-5-yl, 3-azabicyclo[3.2.2]nonan-3-yl, 3-methyl-3,9-diazabicyclo[3.3.1]nonan-9-yl, 3-oxa-9-azabicyclo[3.3.1]nonan-9-yl and 3-thia-9-azabicyclo[3.3.1]nonan-9-yl.

The group derived from the heterocyclic spiro compound includes e.g. 1,4-dioxa-8-azaspiro[4.5]-decan-8-yl, 1,4-dioxa-7-azaspiro[4.4]decan-7-yl, 1,5-dithia-9-azaspiro[5.5]undecan-9-yl and 1-phenyl-4-oxo-1,3,8-triazaspiro[4.5]decan-8-yl.

It should be understood that the compounds of formula (I) include all of their possible isomers including stereoisomer, metabolite, metabolic precursor and metabolic intermediate.

The compounds of formula (I) can be prepared by various conventional procedures as described below. The compounds of formula (I) are prepared by reacting a compound of formula (II)

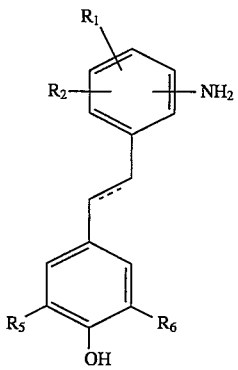

(II)

wherein $R_1$ and $R_2$ as well as $R_5$ and $R_6$ are as defined above, and

denotes —$CH_2$—$CH_2$— or —CH=CH— with an isocyanate of formula (III)

R—NCO  (III)

wherein R denotes $R_3$ or $R_4$, and $R_3$ and $R_4$ are as defined above in an organic solvent under ice-cooling or at a temperature up to room temperature. This reaction is performed using the compound of formula (III) in an amount of 0.1 to 10 moles, preferably 0.5 to 2 moles per mole of the compound of formula (II).

Alternatively, the compounds of formula (I) are prepared by reacting an isocyanate of formula (IV)

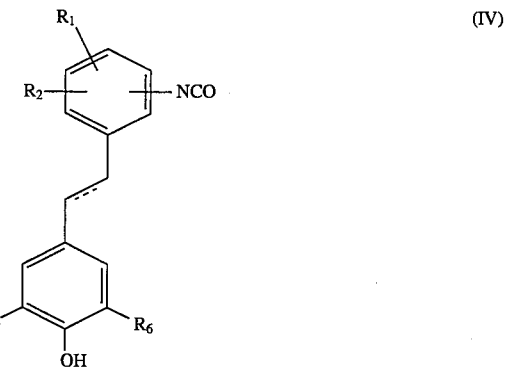

(IV)

wherein $R_1$ and $R_2$ as well as $R_5$ and $R_6$ are as defined above, and

denotes —$CH_2$—$CH_2$— or —CH=CH— with an amine of formula (V)

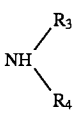

(V)

wherein R denotes $R_3$ or $R_4$, and $R_3$ and $R_4$ are as defined above in an organic solvent under ice-cooling or at a temperature up to room temperature. This reaction is performed using the compound of formula (V) in an amount of 0.1 to 10 moles, preferably 0.5 to 2 moles per mole of the compound of formula (IV).

Alternatively, the compounds of formula (I) are prepared by reacting a carbamate of formula (VI)

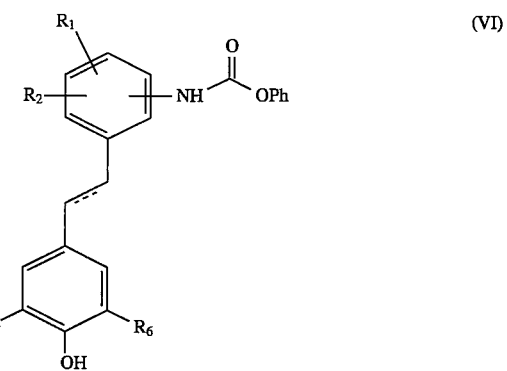

(VI)

wherein $R_1$ and $R_2$ as well as $R_5$ and $R_6$ are as defined above, and

denotes —CH$_2$—CH$_2$— or —CH=CH— with an amine of formula (V) wherein R denotes R$_3$ or R$_4$, and R$_3$ and R$_4$ are as defined above in an organic solvent while heating at 50°–150° C. This reaction is performed using the compound of formula (V) in an amount of 0.1 to 10 moles, preferably 0.5 to 2 moles per mole of the compound of formula (VI).

Alternatively, the compounds of formula (I) are prepared by reacting a compound of formula (II) with a carbamate of formula (VII)

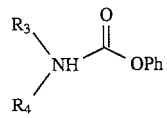
(VII)

wherein R denotes R$_3$ or R$_4$, and R$_3$ and R$_4$ are as defined above in an organic solvent while heating to 50°–150° C. This reaction is performed using the compound of formula (VII) in an amount of 0.1 to 10 moles, preferably 0.5 to 2 moles per mole of the compound of formula (II).

The isocyanates of formula (III) or (IV) are prepared, for example, by treating a carboxylic acid of formula RCOOH wherein R denotes R$_3$ or R$_4$, and R$_3$ and R$_4$ are as defined above or a derivative thereof with 1 to 10 moles, preferably 1 to 3 moles of diphenylphosphoryl azide, trimethylsilylazide or the like, per mole of the carboxylic acid, in an organic solvent to give an acyl azide, which is in turn subjected to a rearrangement reaction under heating at 50°–150° C., or alternatively by reacting a compound of formula (V) or (II) with phosgen.

The carbamate of formula (VI) or (VII) are prepared by reacting a compound of formula (II) or (V) with 0.1 to 10 moles, preferably 0.5 to 2 moles of phenyl chloroformate per mole of the compound in an organic solvent under ice-cooling or at a temperature up to room temperature. This reaction may be conducted in the presence of an acid binder. The acid binders include e.g. inorganic basic substances such as sodium hydride, potassium hydroxide, sodium carbonate, potassium carbonate and organic basic substances including secondary amines such as diisopropylamine and tertiary amines such as triethylamine, methylmorpholine, pyridine.

The organic solvents used in each of the abovedescribed reactions include aliphatic hydrocarbon solvents such as hexane, petroleum ether and cyclohexane, aromatic hydrocarbon solvents such as benzene, toluene and xylenes, halogenated hydrocarbon solvents such as methylene chloride, chloroform, carbon tetrachloride and dichloroethane, ether solvents such as ethyl ether, isopropyl ether, tetrahydrofuran and dioxane, ketone solvents such as acetone and methyl ethyl ketone, ethyl acetate, acetonitrile and N,N-dimethylformamide.

The process steps for the compounds of the invention according to the reactions as described above are shown in the following scheme 1:

Scheme 1

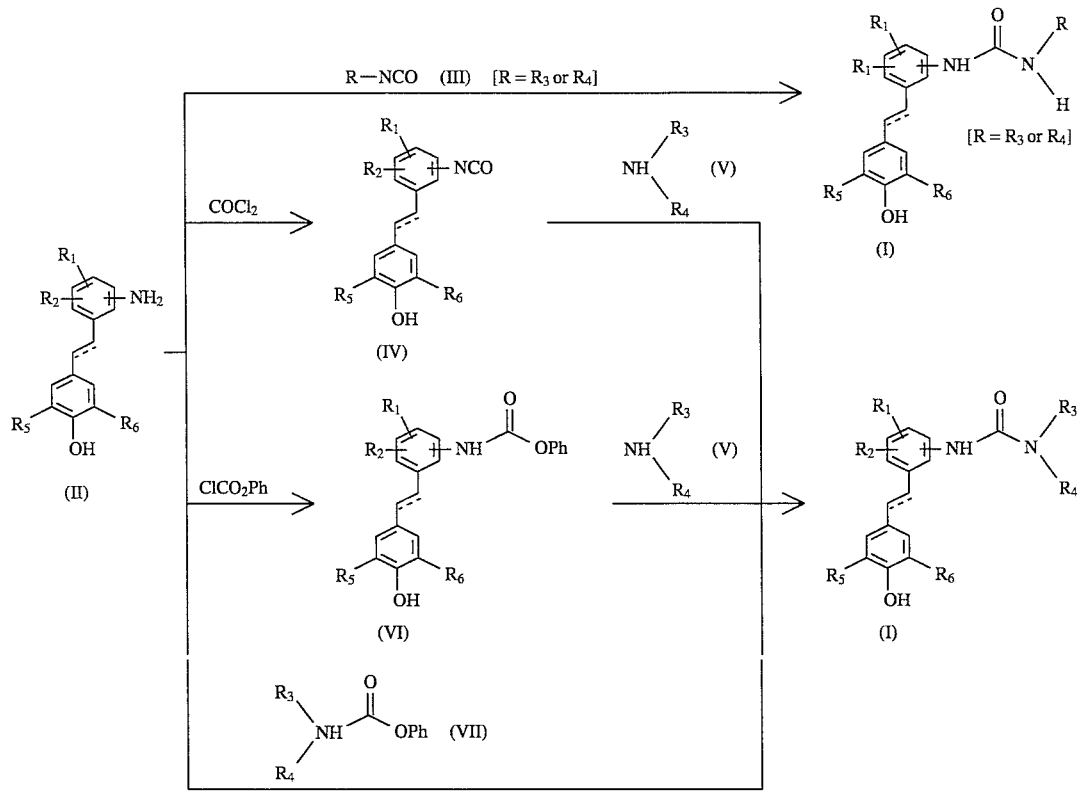

The compounds of formula (II) are prepared by reacting a nitrophenylacetic acid derivative of formula (IX)

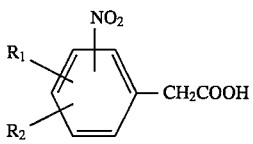

wherein $R_1$ and $R_2$ are as defined above with a benzaldehyde derivative of formula (VIII)

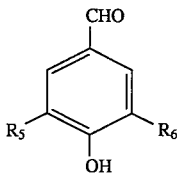

wherein $R_5$ and $R_6$ are as defined above while heating at 100° to 200° C. in the presence of a catalytic amount of a basic material such as piperidine, to form a compound of formula (X)

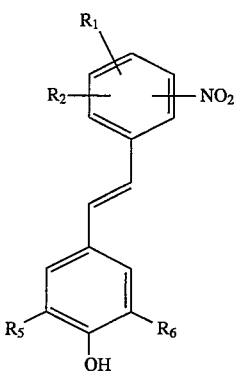

wherein $R_5$ and $R_6$ are as defined above, followed by reduction. The reaction is performed using the compound of formula (VIII) in an amount of 0.1 to 10 moles, preferably 0.5 to 2 moles per mole of the compound of formula (IX). The reduction process includes e.g. that using zinc, iron, tin, stannous chloride or the like in an acidic solution such as hydrochloric acid, acetic acid or a catalytic hydrogenation using a catalyst such as palladium carbon, platinum oxide or the like. The process steps by the reactions as described above are shown in the following scheme 2:

Scheme 2

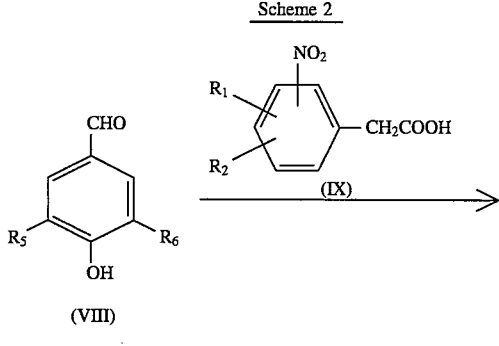

-continued
Scheme 2

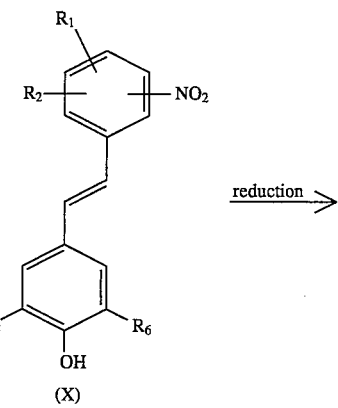

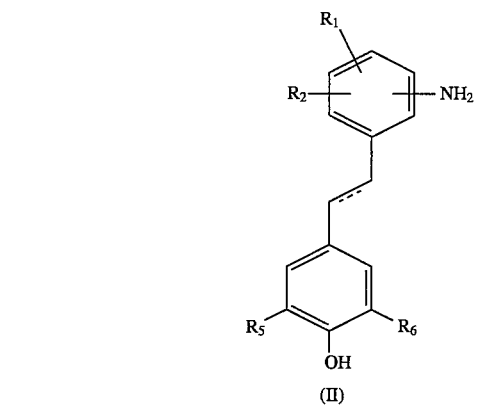

Pharmaceutically acceptable salts of the compounds of formula (I) may be formed in conventional way. The acid addition salts may be formed for example by reaction of the base compound of formula (I) with a pharmaceutically acceptable inorganic acid such as hydrochloric, hydrobromic, hydroiodic, sulfuric and phosphoric acids or a pharmaceutically acceptable organic acid such as oxalic, maleic, fumaric, lactic, malic, citric, tartaric, benzoic and methanesulphonic acids.

The compounds of formula (I) according to the present invention possess both an ACAT inhibitor activity and an antioxidative activity, especially a protective ability against an oxidative modification of LDL. By the ACAT inhibitory activity, the present compounds can inhibit an absorption of cholesterol from the intestinal tracts, reduce a plasma cholesterol level and inhibit an accumulation of cholesteryl esters in the wall of blood vessels, atheroma lesion and macrophage. By the antioxidative activity, especially a protective activity against the oxidative modification of LDL, the present compounds can inhibit the formation and progression of atherosclerosis lesion and inducing its regression.

Thus, the compounds of the present invention are useful in the prophylaxis or treatment of hypercholesterolemia and atherosclerosis.

According to another aspect of the present invention, there is provided an ACAT inhibitor comprising the compound of formula (I) or a pharmaceutically acceptable salt thereof.

In further aspects, the present invention provides a pharmaceutical composition for the prophylaxis or treatment of hypercholesterolemia or atherosclerosis, which comprises as an active ingredient the compound of formula (I) or a pharmaceutically acceptable salt thereof and a pharmaceutically acceptable carrier and/or excipient.

The compounds of the invention can usually be administered orally or parenterally in the form of a pharmaceutical preparation. The pharmaceutical preparations include tablets, capsules, troches, syrups, granules, powders, injections, suspensions and the like. It may be in bilayered or multilayered tablet with other drugs. The tablets may also be coated with a conventional coating to form, e.g., sugar-coated, enteric-coated or film-coated tablets.

In preparing solid preparations, additives such as lactose, refined sugar, crystalline cellulose, corn starch, calcium phosphate, sorbitol, glycin, carboxymethylcellulose, gum arabic, polyvinylpyrrolidone, hydroxypropylcellulose, polyethylene glycol, stearic acid, magnesium stearate and talc are employed.

A vegetable or synthetic wax or fat or a similar base is used in preparing the semi-solid preparations.

As additives in preparing the liquid preparations are used, for example, sodium chloride, sorbitol, glycerin, olive oil, almond oil, propylene glycol and ethyl alcohol.

The active ingredient is contained in the formulation in an amount of 0.0001–100% by weight, suitably 0.001–50% by weight in the case of formulations for oral administration and 0.0001–10% by weight in the case of formulations for injection based on the weight of the preparations.

Route and dosage of administration for the compounds of the invention are not specifically limited and are appropriately chosen depending upon form of the formulation, age and sex of the patient, severity of the disease and other factors. Daily dosage of the active ingredient is 0.01–1000 mg. No adverse toxicological effects are indicated at any of the above dosage ranges.

The invention is further illustrated by the following examples.

EXAMPLE 1

N-[2-(3,5-di-tert-butyl-4-hydroxyphenethyl)phenyl]-N'-(4-hexyloxyphenyl)urea

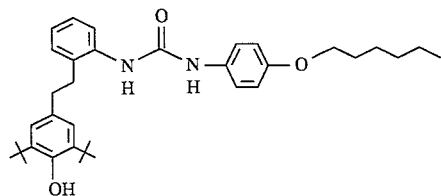

A solution of diphenylphosphorylazide (0.93 g, 3.4 mmol), 4-hexyloxybenzoic acid (0.68 g, 3.1 mmol) and triethylamine (0.34 g, 3.4 mmol) in toluene (10 ml) was stirred at room temperature for 3.5 hrs and heated at about 90° C. for 2 hrs with stirring. After allowing the mixture to cool (under 0° C.), a solution of 4-(2-aminophenethyl)-2,6-di-tert-butylphenol (1.0 g, 3.1 mmol) in toluene (4 ml) was added dropwise. The solution was warmed up to room temperature and stirred overnight. After distilling off the solvent and purification of the residue by a silica gel column chromatography, recrystallization from ethyl acetate/hexane afforded N-[2-(3,5-di-tert-butyl-4-hydroxyphenethyl)phenyl]-N'-(4-hexyloxyphenyl)urea (1.2 g, 71% yield). m.p. 174°–176° C.

$^1$H-NMR($\delta$ ppm, CDCl$_3$) 7.40–7.42(m, 1H), 7.14–7.26(m, 5H), 6.81(s, 2H), 6.76–6.79(m, 2H), 5.98(s, 1H), 5.39(s, 1H), 5.13(s, 1H), 3.88(t, J=7 Hz, 2H), 2.83–2.87(m, 2H), 2.76–2.80(m, 2H), 1.70–1.77(m, 2H), 1.38(s, 18H), 1.30–1.45(m, 6H), 0.87–0.93(m, 3H)

IR (cm$^{-1}$) 3640, 3310, 2950, 1630, 1560, 1490, 1440, 1230

EXAMPLE 2

N-[2-(3,5-di-tert-butyl-4-hydroxyphenethyl)phenyl]-N'-(8-heptadecenyl)urea

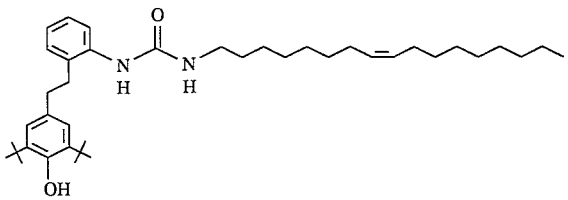

The title compound was prepared in a similar manner to that mentioned in Example 1, using 9-octadecenoic acid instead of 4-hexyloxybenzoic acid.

$^1$H-NMR ($\delta$ ppm, CDCl$_3$) 7.16–7.26(m, 4H), 6.78(s, 2H), 5.29–5.34(m, 2H), 5.12(s, 1H), 5.00(s, 1H), 4.19(t, J=6 Hz, 1H), 3.11(dd, J=14, 6 Hz, 2H), 2.77–2.87(m, 4H), 1.93–2.02(m, 4H), 1.38(s, 18H), 1.18–1.38(m, 25H)

IR (cm$^{-1}$) 3642, 3288, 2926, 1639, 1558, 1435, 1233, 750

EXAMPLE 3

N-[2-(3,5-di-tert-butyl-4-hydroxyphenethyl)phenyl]-N'-(7-methoxycarbonylheptyl)urea

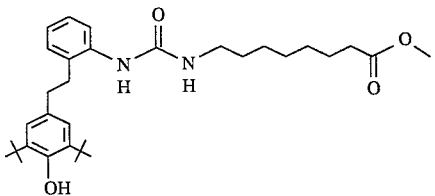

The title compound was prepared in similar manner to that mentioned in Example 1, using 8-methoxycarbonyloctanoic acid instead of 4-hexyloxybenzoic acid $^1$H-NMR ($\delta$ ppm, CDCl$_3$) 7.16–7.26(m, 4H), 6.78(s, 2H), 5.12(s, 1H), 4.98(s, 1H), 4.17(t, J=6 Hz, 1H), 3.66(s, 3H), 3.09–3.14(m, 2H), 2.77–2.87(m, 4H), 2.28(t, J=8Hz, 2H), 1.53–1.61(m, 2H), 1.38(s, 18H), 1.18–1.30(m, 6H), 0.88(t, J=7Hz, 2H)

IR (cm$^{-1}$) 3640, 2928, 1737, 1639, 1547, 1436, 1234

EXAMPLE 4

N-[2-(3,5-di-tert-butyl-4-hydroxyphenethyl)phenyl]-N'-cycloheptylurea

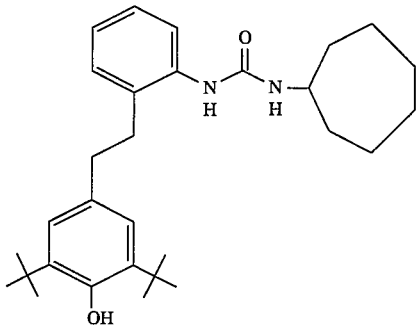

The title compound was prepared in a similar manner to that mentioned in Example 1, using cycloheptanecarboxylic acid instead of 4-hexyloxybenzoic acid. m.p. 177°–178° C.

$^1$H-NMR (δ ppm, CDCl$_3$) 7.17–7.26(m, 4H), 6.79(s, 2H), 5.10(s, 1H), 5.05(bs, 1H), 4.19(d, J=8Hz, 1H), 3.75–3.85(m, 1H), 2.80–2.88(m, 2H), 2.75–2.80(m, 2H), 1.83–1.90(m, 2H), 1.38(s, 18H), 1.21–1.58(m, 10H)

IR (cm$^{-1}$) 3650, 3300, 2930, 2860, 1630, 1570, 1440, 1240

EXAMPLE 5

N-[2-(3,5-di-tert-butyl-4-hydroxyphenethyl)phenyl]-N'-phenethylurea

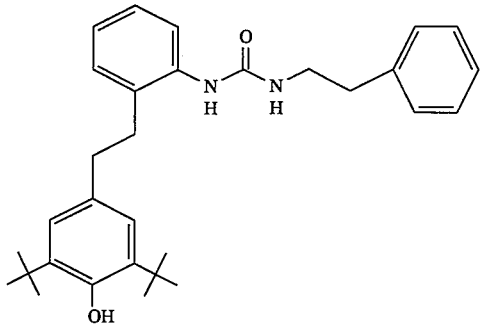

The title compound was prepared in a similar manner to that mentioned in Example 1, using 3-phenylpropionic acid instead of 4-hexyloxybenzoic acid.

m.p. 197°–198° C.

$^1$H-NMR (δ ppm, CDCl$_3$) 7.08–7.25(m, 9H), 6.76(s, 2H), 5.10(s, 1H), 5.00(s, 1H), 4.24(t, J=6 Hz, 1H), 3.36–3.41(m, 2H), 2.72–2.80(m, 6H), 1.36(s, 18H)

IR (cm$^{-1}$) 3632, 3284, 2954, 1640, 1559, 1436, 1235, 748

EXAMPLE 6

N-[2-(3,5-di-tert-butyl-4-hydroxyphenethyl)phenyl]-N'-(2,2-diphenylethyl)urea

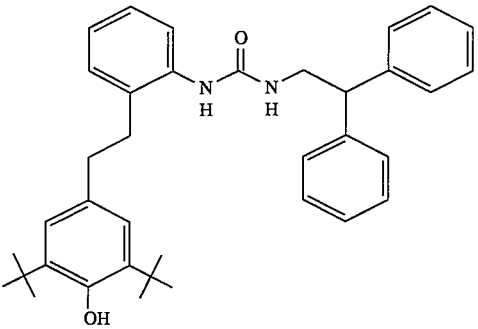

The title compound was prepared in a similar manner to that mentioned in Example 1, using 3,3-diphenylpropionic acid instead of 4-hexyloxybenzoic acid.

m.p. 179° C.

$^1$H-NMR (δ ppm, CDCl$_3$) 7.09–7.44(m, 12H), 6.97–7.01(m, 1H), 6.78(d, J=8 Hz, 1H), 6.72(s, 2H), 5.07(s, 1H), 4.93(s, 1H), 4.23(t, J=6 Hz, 1H), 4.15(t, J=8 Hz, 1H), 3.77(dd, J=8, 6 Hz, 2H), 2.70(s, 4H), 1.35(s, 18H)

IR (cm$^{-1}$) 3644, 2930, 1650, 1553, 1510, 1234

EXAMPLE 7

N-[2-(3,5-di-tert-butyl-4-hydroxyphenethyl)phenyl]-N'-(2,6-diisopropylphenyl)urea

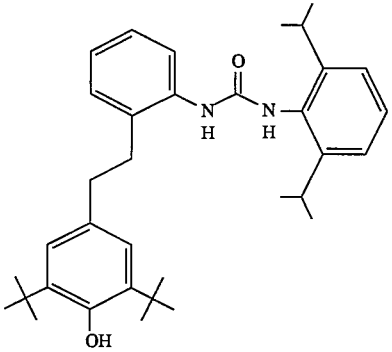

The title compound was prepared in a similar manner to that mentioned in Example 1, using 2,6-diisopropylbenzoic acid instead of 4-hexyloxybenzoic acid.

m.p. 209°–210° C.

$^1$H-NMR(δ ppm, DMSO) 8.01(bs, 1H), 7.85(bs, 1H), 7.65(d, J=8 Hz, 1H), 7.20–7.24(m, 1H), 7.10–7.14(m, 4H), 6.93–6.97(m, 3H), 6.62(s, 1H), 3.32–3.53(m, 1H), 3.18–3.25(m, 1H), 2.75–2.85(m, 4H), 1.37(s, 18H), 1.13(d, J=7 Hz, 12H)

IR (cm$^{-1}$) 3612, 3320, 2958, 1646, 1586, 1534, 1435, 1231, 745

EXAMPLE 8

N-[2-(3,5-di-tert-butyl-4-hydroxyphenethyl)phenyl]-N'-(3-cyclohexylpropyl)urea

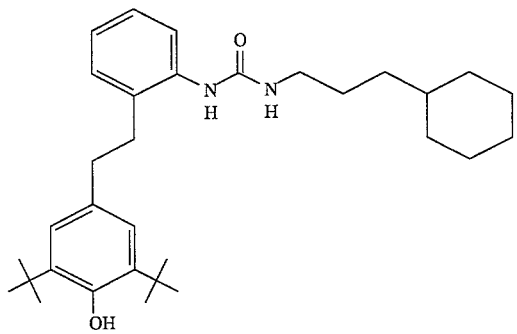

The title compound was prepared in a similar manner to that mentioned in Example 1, using 4-cyclohexylbutanoic acid instead of 4-hexyloxybenzoic acid.

m.p. 166° C.

$^1$H-NMR(δ ppm, CDCl$_3$)7.18–7.26(m, 4H), 6.78(s, 2H), 5.11(s, 1H), 5.02(s, 1H), 4.20(t, 1H), 3.10 (dt, J=6, 7 Hz, 2H), 2.83–2.85(m, 2H), 2.76–2.80(m, 2H), 1.56–1.68(m, 4H), 1.38(s, 18H), 1.33–1.43(m, 2H), 1.04–1.30(m, 6H), 0.75–0.88(m, 3H)

IR (cm$^{-1}$) 3640, 3316, 2924, 1640, 1558, 1436, 1233, 749

EXAMPLE 9

N-[2-(3,5-di- tert-butyl-4-hydroxyphenethyl)phenyl]-N'-[3-(2-thienyl)propyl]urea

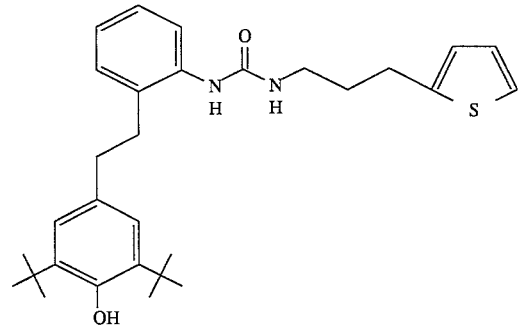

The title compound was prepared in a similar manner to that mentioned in Example 1, using 4-(2-thienyl)butanoic acid instead of 4-hexyloxybenzoic acid.

m.p. 150° C.

$^1$H-NMR (δ ppm, CDCl$_3$) 7.19–7.27(m, 4H), 7.07(dd, J=4, 1 Hz, 1H), 6.87 (dd, J=3, 2 Hz, 1H), 6.77(s, 2H), 6.71(t, J=2 Hz, 1H), 5.11(s, 1H), 4.96(s, 1H), 4.21(t, 1H), 3.20(s, 2H), 2.77–2.87(m, 6H), 1.81(qui, J=7 Hz, 2H), 1.37(s, 18H)

IR (cm$^{-1}$) 3638, 3286, 2918, 1630, 1570, 1434, 1233, 696

EXAMPLE 10

N-[2-(3,5-di-tert-butyl-4-hydroxyphenethyl)phenyl]-N'-phenylurea

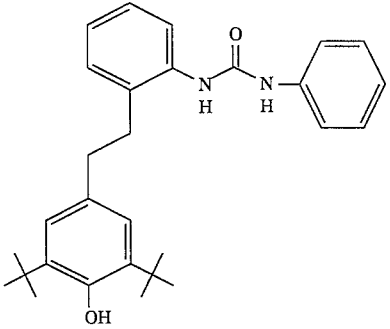

The title compound was prepared in a similar manner to that mentioned in Example 1, using benzoic acid instead of 4-hexyloxybenzoic acid. m.p. 207° C. $^1$H-NMR(δ ppm, CDCl$_3$) 7.22–7.36(m, 8H), 7.02(t, J=7 Hz, 1H), 6.80(s, 2H), 6.02(s, 1H), 5.18(s, 1H), 5.15(s, 1H), 2.79–2.91(m, 4H), 1.38(s, 18H)

IR (cm$^{-1}$) 3630, 3350, 2950, 1650, 1600, 1550, 1500, 1230, 750

EXAMPLE 11

(1) N-[2-(3,5-di-tert-butyl-4-hydroxyphenethyl)phenyl]phenyl carbamate

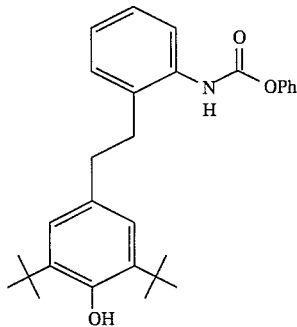

To a solution of 4-(2-aminophenethyl)-2,6-di-tert-butylphenol (7.00 g, 21.5 mmol) and diisopropylamine (3.4 ml, 24 mmol) in dichloromethane (50 ml) was added dropwise a solution of phenyl chloroformate (3.60 g, 23.0 mmol) in dichloromethane (10 ml) so that the internal temperature does not exceed 0° C. over a ice-cold water bath. The mixture was stirred at the same temperature for 2 hrs, washed with water, dried over MgSO$_4$ and concentrated. Purification of the residue by a silica gel column chromatography gave a viscous oil of N-[2-(3,5-di-tert-butyl-4-hydroxyphenethyl)phenyl]phenyl carbamate (8.16 g, 85.2% yield).

$^1$H-NMR (δ ppm, CDCl$_3$) 7.63 (bs, 1H), 7.34 (t, J=8 Hz, 2H), 7.08–7.29(m, 6H), 6.80(s, 2H), 5.74(bs, 1H), 5.13(s, 1H), 2.8–2.9(m, 4H), 1.35(s, 18H)

(2) N-[2-(3,5-di-tert-butyl-4-hydroxyphenethyl)phenyl]-N'-decylurea

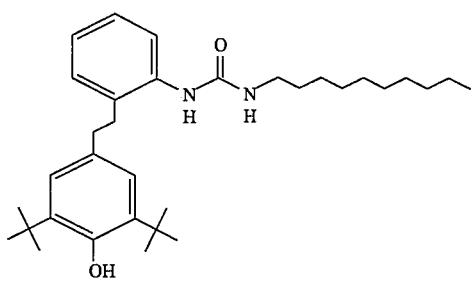

A solution of N-[2-(3,5-di-tert-butyl-4-hydroxyphenethyl)phenyl]phenyl carbamate (1.0 g, 2.2 mmol) and decylamine (0.38 g, 2.4 mmol) in xylene (10 ml) was heated under reflux for 2.5 hrs. After distilling off the solvent, purification of the residue by a silica gel column chromatography afforded waxy N-[2-(3,5-di-tert-butyl-4-hydroxyphenethyl)phenyl]-N'-decylurea (0.93 g, 85% yield).

$^1$H-NMR (δ ppm, CDCl$_3$) 7.17–7.26(m, 4H), 6.78(s, 2H), 5.11(s, 1H), 4.98(s, 1H), 4.17(t, J=6 Hz, 1H), 3.09–3.16(m, 2H), 2.76–2.87(m, 4H), 1.50–2.50(m, 16H), 1.38(s, 18H), 0.87(t, J=7 Hz, 3H)

IR (cm$^{-1}$) 3650, 3350, 2960, 2930, 2850, 1640, 1570

EXAMPLE 12

N-[2-(3,5-di-tert-butyl-4-hydroxyphenethyl)phenyl]-N'-heptylurea

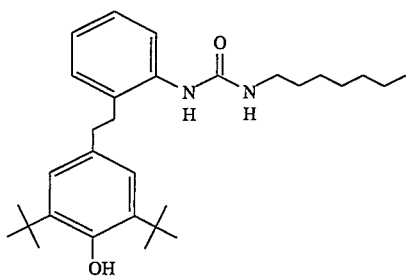

The title compound was prepared in a similar manner to that mentioned in Example 11, using heptylamine instead of decylamine. m.p. 100° C.

$^1$H-NMR (δ ppm, CDCl$_3$) 7.18–7.27(m, 4H), 6.78(s, 2H), 5.11(s, 1H), 4.99(s, 1H), 4.18(bt, J=5 Hz, 1H), 2.89(q, J=6 Hz, 2H), 2.79–2.85(m, 4H), 1.38–1.45(m, 2H), 1.38(s, 18H), 1.15–1.30(m, 8H), 0.86(t, J=7 Hz, 3H)

IR (cm$^{-1}$) 3650, 3320, 2970, 2940, 2870, 1640, 1570, 1440, 1240, 760

EXAMPLE 13

N-[2-(3,5-di-tert-butyl-4-hydroxyphenethyl)phenyl]-N'-(3,7-dimethyl-2,6-octadienyl)urea

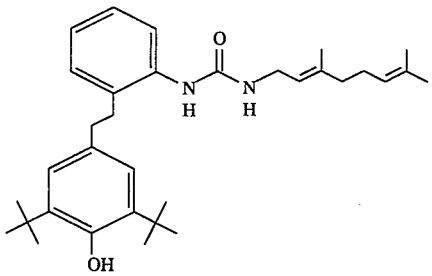

The title compound was prepared in a similar manner to that mentioned in Example 11, using 3,7-dimethyl-2,6-octadienylamine instead of decylamine. m.p. 87.0°–87.5° C.

$^1$H-NMR(δ ppm, CDCl$_3$) 7.16–7.30(m, 4H), 6.78(s, 2H), 5.10(s, 1H), 5.05–5.13(m, 1H), 5.02(bs, 2H), 4.05–4.12(m, 1H), 3.75(t, J=6 Hz, 2H), 2.80–2.85(m, 2H), 2.75–2.80(m, 2H), 1.95–2.08(m, 2H), 1.89–1.95(m, 2H), 1.65(s, 3H), 1.60(s, 3H), 1.57(s, 3H), 1.37(s, 18H)

IR (cm$^{-1}$) 3628, 3312, 2956, 1638, 1585, 1436, 1233, 752

EXAMPLE 14

N-[2-(3,5-di-tert-butyl-4-hydroxyphenethyl)phenyl]-N'-(2,4,4-trimethyl-2-pentyl)urea

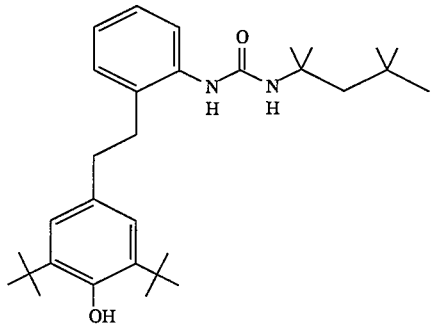

The title compound was prepared in a similar manner to that mentioned in Example 11, using 2,2,4-trimethyl-2-pentylamine instead of decylamine. m.p. 168°–169° C.

$^1$H-NMR (δ ppm, CDCl$_3$) 7.15–7.26(m, 4H), 6.83(s, 2H), 5.09(s, 2H), 4.18(s, 1H), 2.71–2.87(m, 4H), 1.64(s, 2H), 1.39(s, 18H), 1.34(s, 6H), 0.90(s, 9H)

IR (cm$^{-1}$) 3640, 3334, 2956, 1645, 1556, 1437, 1365, 1226

EXAMPLE 15

N-[2-(3,5-di-tert-butyl-4-hydroxyphenethyl)phenyl]-N'-(3-ethoxypropyl)urea

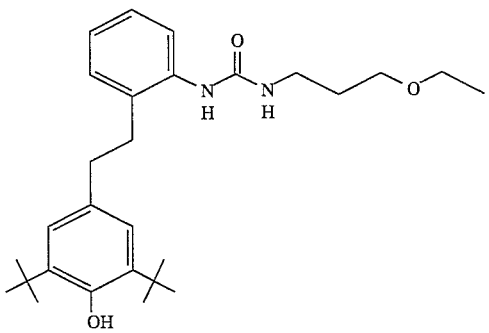

The title compound was prepared in a similar manner to that mentioned in Example 11, using 3-ethoxypropylamine instead of decylamine. m.p. 136°–137° C.

$^1$H-NMR (δ ppm, CDCl$_3$) 7.16–7.27(m, 4H), 6.79(s, 2H), 5.10(s, 1H), 5.06(s, 1H), 4.78(t, J=5 Hz, 1H), 3.40(t, J=6 Hz, 2H), 3.32(dd, J=14, 7 Hz, 2H), 3.28(q, J=6 Hz, 2H), 2.84–2.88(m, 2H), 2.77–2.80(m, 2H), 1.67–1.73(m, 2H), 1.38(s, 18H), 0.99(t, J=7 Hz, 3H)

IR (cm$^{-1}$) 3600, 3346, 2952, 1638, 1563, 1436, 1288, 1238, 1108, 753

EXAMPLE 16

N-[2-(3,5-di-tert-butyl-4-hydroxyphenethyl)phenyl]-N'-cyclopentylurea

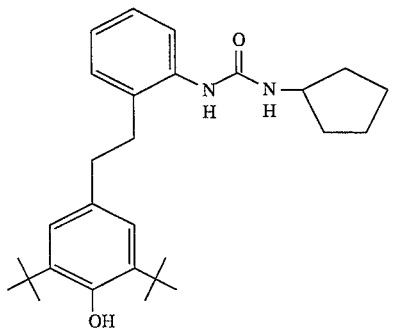

The title compound was prepared in a similar manner to that mentioned in Example 11, using cyclopentylamine instead of decylamine. m.p. 186°–187° C.

$^1$H-NMR (δ ppm, CDCl$_3$) 7.15–7.28(m, 4H), 6.79(s, 2H), 5.11(s, 1H), 5.08(s, 1H), 4.17(d, J=7 Hz, 1H), 4.01–4.10(m, 1H), 2.76–2.87(m, 4H), 1.89–1.96(m, 2H), 1.50–1.61(m, 4H), 1.39(s, 18H), 1.22–1.29(m, 2H)

IR (cm$^{-1}$) 3650, 3350, 2950, 1640, 1580, 1560, 1440, 1240

EXAMPLE 17

N-[2-(3,5-di-tert-butyl-4-hydroxyphenethyl)phenyl]-N'-cyclohexylurea

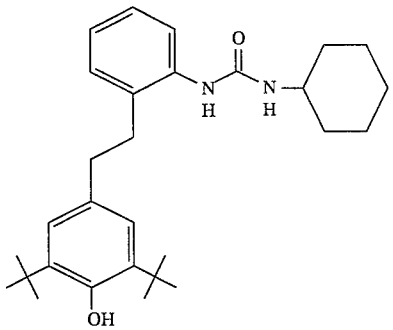

The title compound was prepared in similar manner to that mentioned in Example 11, using cyclohexylamine instead of decylamine. m.p. 198°–200° C.

$^1$H-NMR(δ ppm, CDCl$_3$) 7.16–7.25(m, 4H), 6.78(s, 2H), 5.14(s, 1H), 4.99(s, 1H), 4.09(d, J=5 Hz, 1H), 3.59–3.62(m, 1H), 2.83(d, J=6 Hz, 2H), 2.79(d, J=6 Hz, 2H), 1.95–1.99(m, 2H), 1.53–1.64(m, 4H), 1.38(s, 18H), 1.26–1.30(m, 2H), 0.96–0.99(m, 2H)

IR (cm$^{-1}$) 3290, 2930, 1630, 1561, 1232

EXAMPLE 18

N-[2-(3,5-di-tert-butyl-4-hydroxyphenethyl)phenyl]-N'-cyclooctylurea

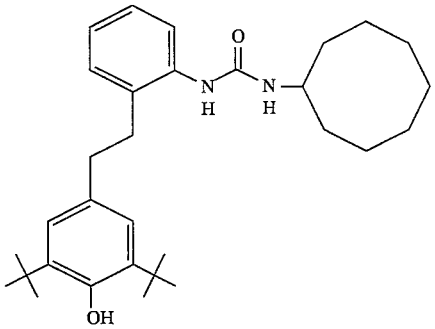

The title compound was prepared in a similar manner to that mentioned in Example 11, using cyclooctylamine instead of decylamine. m.p. 174°–176° C.

¹H-NMR (δ ppm, CDCl₃) 7.17–7.24(m, 4H), 6.79(s, 2H), 5.10(s, 1H), 5.05(s, 1H), 4.19(d, J=5 Hz, 1H), 3.68–3.98(m, 1H), 2.83(d, J=6 Hz, 2H), 2.79(d, J=6 Hz, 2H), 1.74–1.81(m, 2H), 1.42–1.58(m, 12H), 1.38(s, 18H)

IR (cm⁻¹) 3308, 2922, 1630, 1554, 1435, 1233

EXAMPLE 19

N-[2-(3,5-di-tert-butyl-4-hydroxyphenethyl)phenyl]-N'-adamantylurea

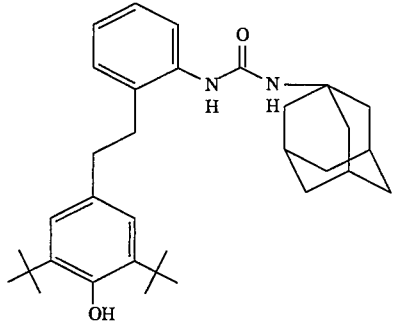

The title compound was prepared in a similar manner to that mentioned in Example 11, using 1-adamantanamine instead of decylamine. m.p. 197°–199° C.

¹H-NMR (δ ppm, CDCl₃) 7.14–7.29(m, 4H), 6.83(s, 2H), 5.11(s, 1H), 5.10(s, 1H), 4.06(s, 1H), 2.79–2.85(m, 4H), 1.91–2.05(m, 9H), 1.60–1.70(m, 6H), 1.39(s, 18H)

IR (cm⁻¹) 3350, 2900, 2850, 1640, 1550, 1440, 1300, 1240

EXAMPLE 20

N-[2-(3,5-di-tert-butyl-4-hydroxyphenethyl)phenyl]-N'-benzylurea

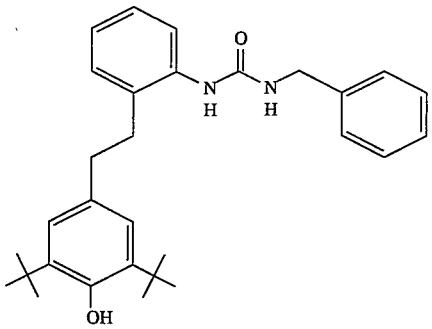

The title compound was prepared in a similar manner to that mentioned in Example 11, using benzylamine instead of decylamine. m.p. 181°–183° C.

¹H-NMR (δ ppm, CDCl₃) 7.15–7.30(m, 9H), 6.77(s, 2H), 5.13(s, 1H), 5.08(s, 1H), 4.54(t, J=6 Hz, 1H), 4.33(d, J=6 Hz, 2H), 2.82(d, J=6 Hz, 2H), 2.78(d, J=6 Hz, 2H), 1.35(s, 18H)

IR (cm⁻¹) 3294, 2956, 1629, 1579, 1435, 1233, 741

EXAMPLE 21

N-[2-(3,5-di-tert-butyl-4-hydroxyphenethyl)phenyl]-N'-(4-methylphenethyl)urea

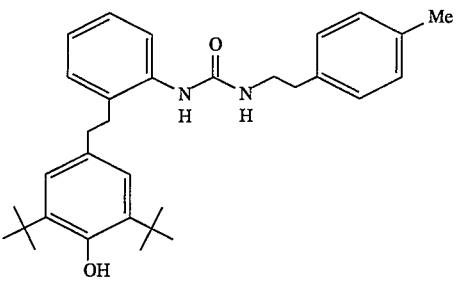

The title compound was prepared in a similar manner to that mentioned in Example 11, using 4-methylphenethylamine instead of decylamine.

m.p. 170°–172° C.

¹H-NMR (δ ppm, CDCl₃) 7.12–7.23(m, 4H), 7.04(d, J=8 Hz, 2H), 6.98(d, J=8 Hz, 2H), 6.76(s, 2H), 5.09(s, 1H), 4.96(s, 1H), 4.22(t, J=6 Hz, 1H), 3.36(q, J=6 Hz, 2H), 2.80(d, J=6 Hz, 2H), 2.69(t, J=6 Hz, 2H), 2.68(d, J=6 Hz, 2H), 2.29(s, 3H), 1.36(s, 18H)

IR (cm⁻¹) 3342, 2950, 1643, 1563, 1435

EXAMPLE 22

N-[2-(3,5-di-tert-butyl-4-hydroxyphenethyl)phenyl]-N'-(4-methoxyphenethyl)urea

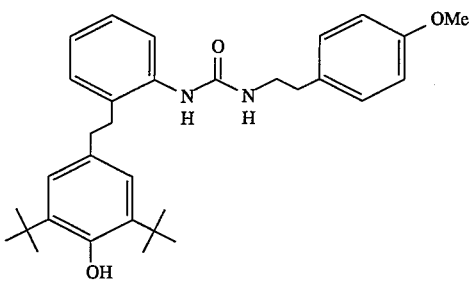

The title compound was prepared in a similar manner to that mentioned in Example 11, using 4-methoxyphenethylamine instead of decylamine.

m.p. 148°–149° C.

¹H-NMR (δ ppm, CDCl₃) 7.10–7.24(m, 4H), 7.00(d, J=9 Hz, 2H), 6.77(d, J=9 Hz, 2H), 6.76(s, 2H), 5.09(s, 1H), 4.95(s, 1H), 4.20(t, J=6 Hz, 1H), 3.76(s, 3H), 3.33(q, J=6 Hz, 2H), 2.80(d, J=6 Hz, 2H), 2.77(d, J=6 Hz, 2H), 2.67(t, J=6 Hz, 2H), 1.36(s, 18H)

IR (cm⁻¹) 3420, 2960, 1641, 1561, 1525, 1249

EXAMPLE 23

N-[2-(3,5-di-tert-butyl-4-hydroxyphenethyl)phenyl]-N'-cyclododecylurea

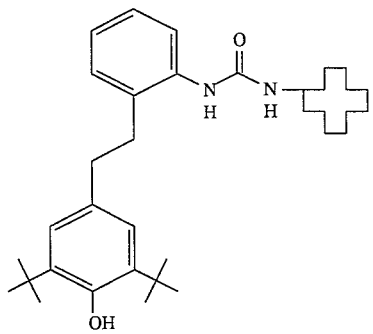

The title compound was prepared in a similar manner to that mentioned in Example 11, using cyclododecylamine instead of decylamine.

$^1$H-NMR (δ ppm, CDCl$_3$) 7.06–7.29(m, 4H), 6.80(s, 2H), 5.10(s, 2H), 4.05(d, J=9 Hz, 1H), 3.89(s, 1H), 2.76–2.87(m, 4H), 1.38(s, 18H), 1.20–1.30(m, 22H)

IR (cm$^{-1}$) 3650, 3340, 2950, 2920, 1640, 1560, 1440, 1240

EXAMPLE 24

N-[2-(3,5-di-tert-butyl-4-hydroxyphenethyl)phenyl]-N'-butylurea

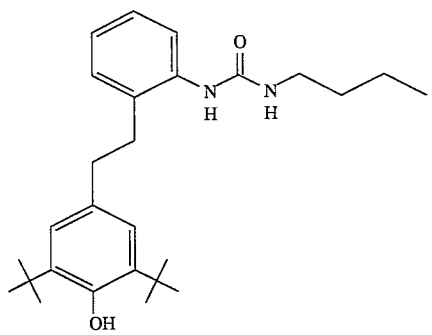

The title compound was prepared in a similar manner to that mentioned in Example 11, using butylamine instead of decylamine. m.p. 133°–134° C.

$^1$H-NMR (δ ppm, CDCl$_3$) 7.16–7.26(m, 4H), 6.78(s, 2H), 5.12(s, 1H), 4.97(s, 1H), 4.16(t, J=6 Hz, 1H), 3.11–3.16(m, 2H), 2.77–2.87(m, 4H), 1.38(s, 18H), 1.21–1.34(m, 4H), 0.87(t, J=7 Hz, 3H)

IR (cm$^{-1}$) 3450, 3320, 2960, 1640, 1570, 1460, 1440, 1250, 1230

EXAMPLE 25

N-[2-(3,5-di-tert-butyl-4-hydroxyphenethyl)phenyl]-N'-[-2-(N,N-dibutylamino)ethyl]urea

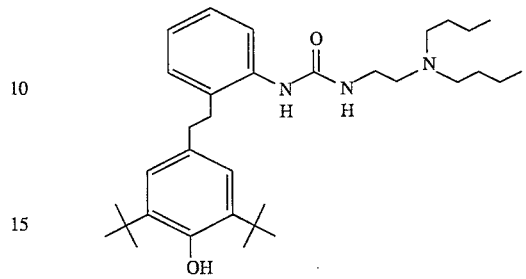

The title compound was prepared in a similar manner to that mentioned in Example 11, using N,N-dibutylethylenediamine instead of decylamine.

$^1$H-NMR (δ ppm, CDCl$_3$) 7.18–7.26(m, 4H), 6.80(s, 2H), 5.18(s, 1H), 5.10(s, 1H), 5.02(bs, 1H), 3.17–3.21(m, 2H), 2.76–2.87(m, 4H), 2.40(t, J=6 Hz, 2H), 2.24(t, J=7 Hz, 4H), 1.38(s, 18H), 1.04–1.26(m, 8H), 0.82(t, J=7 Hz, 6H)

IR (cm$^{-1}$) 3650, 3360, 2960, 2880, 1640, 1560, 1440, 1240

Further, the hydrochloride of the title compound was prepared in the following manner.

Conc. hydrochloric acid (0.17 ml) was added to a solution of the title compound (0.95 g) in ethanol (12 ml). Distilling off the solvent afforded a waxy hydrochloride of the title compound (1.05 g).

EXAMPLE 26

N-[2-(3,5-di-tert-butyl-4-hydroxyphenethyl)phenyl]-N'-(3,4-dimethoxyphenethyl)urea

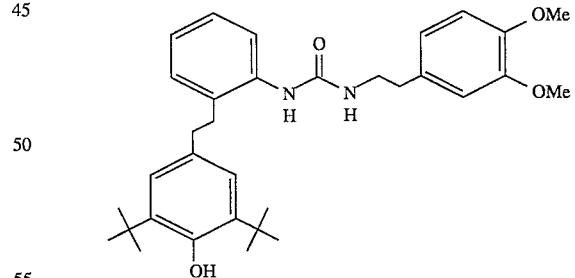

The title compound was prepared in a similar manner to that mentioned in Example 11, using 3,4-dimethoxyphenethylamine instead of decylamine. m.p. 158°–160° C.

$^1$H-NMR(δ ppm, CDCl$_3$) 7.10–7.24(m, 4H), 6.76(s, 2H), 6.70–6.75(m, 1H), 6.60–6.65(m, 2H), 5.10(s, 1H), 5.00(s, 1H), 4.27(t, J=6 Hz, 1H), 3.83(s, 3H), 3.81(s, 3H), 3.35–3.40(dt, J=6, 7 Hz, 2H), 2.72–2.84(m, 4H), 2.68(t, J=7 Hz, 2H), 1.36(s, 18H)

IR (cm$^{-1}$) 3628, 3318, 1632, 1562, 1518, 1264, 1234

EXAMPLE 27

N-[2-(3,5-di-tert-butyl-4-hydroxyphenethyl)phenyl]-N'-(3-phenylpropyl)urea

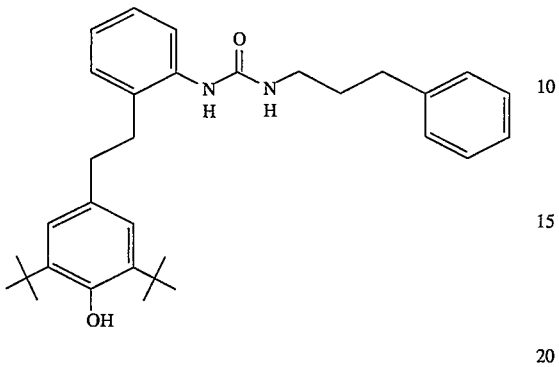

The title compound was prepared in a similar manner to that mentioned in Example 11, using 3-phenylpropylamine instead of decylamine. m.p. 161°–162° C.

$^1$H-NMR (δ ppm, CDCl$_3$) 7.13–7.25(m, 7H), 7.10(d, J=8Hz, 2H), 6.77(s, 2H), 5.10(s, 1H), 4.98(s, 1H), 4.20(t, J=7 Hz, 1H), 3.17(q, J=7 Hz, 2H), 2.83(d, J=6 Hz, 2H), 2.79(d, J=6 Hz, 2H), 2.56(t, J=7 Hz, 2H), 1.74(qui, J=7 Hz, 2H), 1.36(s, 18H)

IR (cm$^{-1}$) 3628, 3328, 2952, 1637, 1562, 1435, 1234, 748, 697

EXAMPLE 28

N-[2-(3,5-di-tert-butyl-4-hydroxyphenethyl)phenyl]-N'-(4-chlorophenethyl)urea

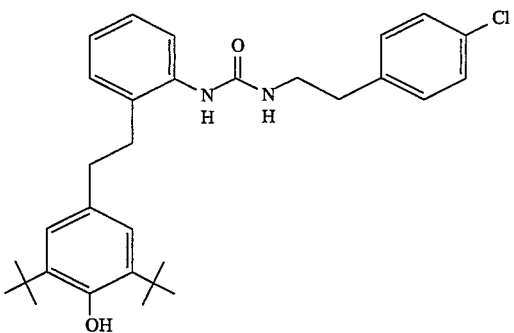

The title compound was prepared in a similar manner to that mentioned in Example 11, using 4-chlorophenethylamine instead of decylamine. m.p. 173°–174° C.

$^1$H-NMR (δ ppm, CDCl$_3$) 7.09–7.20(m, 6H), 7.02(d, 2H), 6.75(s, 2H), 5.10(s, 1H), 4.91(s, 1H), 4.16(t, J=6 Hz, 1H), 3.35(q, J=6 Hz, 2H), 2.78(q, J=5 Hz, 4H), 2.70(t, J=7 Hz, 2H), 1.35(s, 18H)

IR (cm$^{-1}$) 3626, 3322, 2950, 1638, 1561, 1493, 1436, 1234

EXAMPLE 29

N-[2-(3,5-di-tert-butyl-4-hydroxyphenethyl)phenyl]-N'-diphenylmethylurea

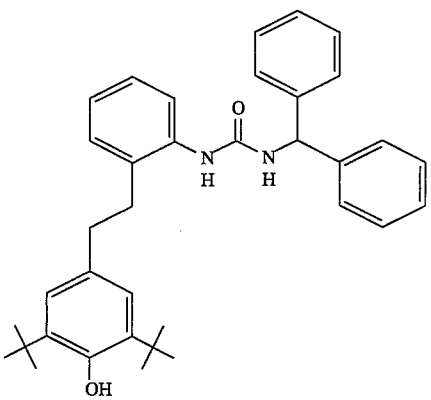

The title compound was prepared in a similar manner to that mentioned in Example 11, using benzhydrylamine instead of decylamine. m.p. 187.4° C.

$^1$H-NMR (δ ppm, CDCl$_3$) 7.14–7.33(m, 14H), 6.75(s, 2H), 6.10(d, J=8 Hz, 1H), 5.17(s, 1H), 5.08(s, 1H), 4.86(d, J=8 Hz, 1H), 2.73–2.81(m, 4H), 1.35(s, 18H)

IR (cm$^{-1}$) 2960, 1640, 1560, 1500, 1460, 1440, 1240, 740, 700

EXAMPLE 30

N-[2-(3,5-di-tert-butyl-4-hydroxyphenethyl)phenyl]-N'-[(2-furyl)methyl]urea

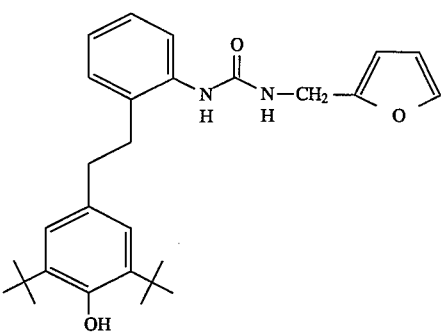

The title compound was prepared in a similar manner to that mentioned in Example 11, using 2-aminomethylfuran instead of decylamine. m.p. 169.7° C.

$^1$H-NMR (δ ppm, CDCl$_3$) 7.15–7.28(m, 5H), 6.76(s, 2H), 6.26–6.27(m, 1H), 6.14–6.15(m, 1H), 5.10(s, 1H), 4.99(s, 1H), 4.45(t, J=6 Hz, 1H), 4.32(d, J=6 Hz, 2H), 2.76–2.86(m, 4H), 1.36(s, 18H)

IR (cm$^{-1}$) 3320, 2950, 1640, 1590, 1570, 1460, 1440, 1240, 730

EXAMPLE 31

N-[2-(3,5-di-tert-butyl-4-hydroxyphenethyl)phenyl]-N'-(4-phenylbutyl)urea

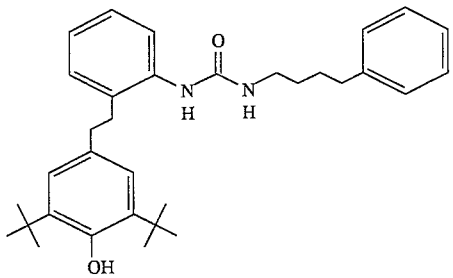

The title compound was prepared in a similar manner to that mentioned in Example 11, using 4-phenylbutylamine instead of decylamine. m.p. 157.0° C.

$^1$H-NMR (δ ppm, CDCl$_3$) 7.11–7.27(m, 9H), 6.77(s, 2H), 5.10(s, 1H), 4.95(s, 1H), 4.15(t, 1H), 3.12—3.17(m, 2H), 2.74–2.86(m, 4H), 2.58(t, J=8 Hz, 2H), 1.39–1.61(m, 4H), 1.37(s, 18H)

IR (cm$^{-1}$) 3300, 2950, 2860, 1620, 1600, 1580, 1440, 1250, 1240

EXAMPLE 32

N-[2-(3,5-di-tert-butyl-4-hydroxyphenethyl)phenyl]-N'-[3-(1-imidazolyl)propyl]urea

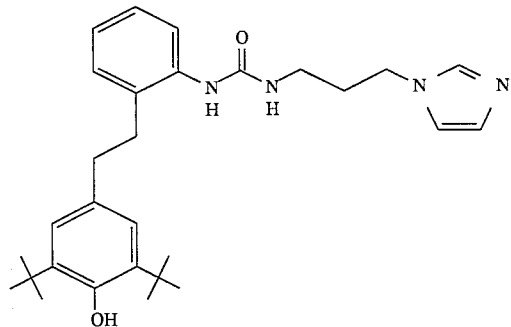

The title compound was prepared in a similar manner to that mentioned in Example 11, using N-(3-aminopropyl)imidazole instead of decylamine.

m.p. 163.5° C.

$^1$H-NMR (δ ppm, CDCl$_3$) 7.39(s, 1H), 7.20–7.29(m, 4H), 7.01(s, 1H), 6.85–6.86(m, 1H), 6.77(s, 2H), 5.15(s, 1H), 4.97(s, 1H), 4.25(t, J=6 Hz, 1H), 3.92(t, J=7 Hz, 2H), 3.13(dt, J=8, 7 Hz, 2H), 2.77–2.86(m, 4H), 1.88–1.95(m, 2H), 1.37(s, 18H)

IR (cm$^{-1}$) 3360, 3320, 2960, 1640, 1570, 1520, 1440, 1240

EXAMPLE 33

N-[2-(3,5-di-tert-butyl-4-hydroxyphenethyl)phenyl]-N'-[2-(2-pyridyl)ethyl]urea

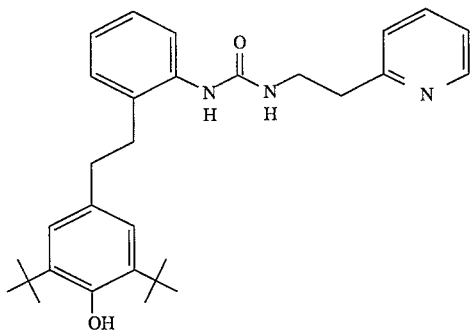

The title compound was prepared in a similar manner to that mentioned in Example 11, using 2-(2-aminoethyl)pyridine instead of decylamine.

m.p. 179.7° C.

$^1$H-NMR (δ ppm, CDCl$_3$) 8.32(d, J=4 Hz, 1H), 7.52–7.56(m, 1H), 7.06–7.27(m, 6H), 6.77(s, 2H), 5.21(t, J=6 Hz, 1H), 5.11(s, 1H), 5.10(s, 1H), 3.56(q, J=6 Hz, 2H), 2.93(t, J=6 Hz, 2H), 2.67–2.83(m, 4H), 1.37(s, 18H)

IR (cm$^{-1}$) 3350, 2960, 1650, 1590, 1570, 1440, 760

EXAMPLE 34

N-[2-(3,5-di-tert-butyl-4-hydroxyphenethyl)phenyl]-N'-[1-(4-fluorophenyl)-2-methyl-2-propyl]urea

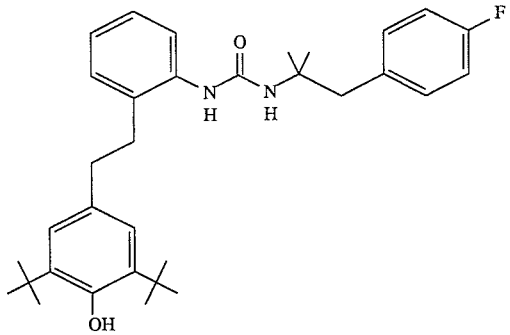

The title compound was prepared in a similar manner to that mentioned in Example 11, using 4-fluoro-α,α-dimethylphenethylamine instead of decylamine.

m.p. 150.6° C.

$^1$H-NMR (δ ppm, CDCl$_3$) 6.84–7.26(m, 8H), 6.80(s, 2H), 5.10(s, 1H), 5.09(s, 1H), 3.95(s, 1H), 2.95(s, 2H), 2.72–2.82(m, 4H), 1.37(s, 18H), 1.25(s, 6H)

IR (cm$^{-1}$) 3350, 2960, 1640, 1560, 1510, 1440, 1240

EXAMPLE 35

N-[2-(3,5-di-tert-butyl-4-hydroxyphenethyl)phenyl]-N'-(1-benzyl-4-piperidyl)urea

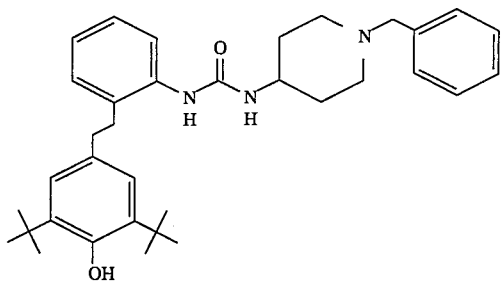

The title compound was prepared in a similar manner to that mentioned in Example 11, using 4-amino-1-benzylpiperidine instead of decylamine. m.p. 79°–81° C.

$^1$H-NMR (δ ppm, CDCl$_3$) 7.20–7.34 (m, 9H), 6.77(s, 2H), 5.10(s, 1H), 4.99(s, 1H), 4.07–4.15(m, 1H), 3.58–3.72(m, 1H), 3.44(s, 2H), 2.68–2.86(m, 6H), 2.00–2.10(m, 2H), 1.80–1.90(m, 2H), 1.37(s, 18H), 1.24–1.35(m, 2H)

IR (cm$^{-1}$) 3632, 3350, 1640, 1552

EXAMPLE 36

N-[2-(3,5-di-tert-butyl-4-hydroxyphenethyl)phenyl]-N'-[2-(3-indolyl)ethyl]urea

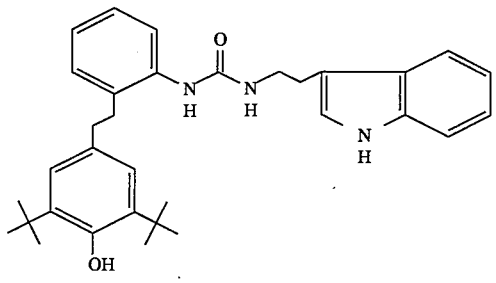

The title compound was prepared in a similar manner to that mentioned in Example 11, using 3-(2-aminoethyl)indole instead of decylamine.

m.p. 193°–194° C.

$^1$H-NMR (δ ppm, CDCl$_3$) 7.92 (s, 1H), 7.54(d, J=8 Hz, 1H), 7.33(d, J=8 Hz, 1H), 7.05–7.26(m, 6H), 6.90(d, J=2 Hz, 1H), 6.77(s, 2H), 5.10(s, 1H), 5.00(s, 1H), 4.32(t, J=6 Hz, 1H), 3.47(dt, J=6, 7 Hz, 2H), 2.90(t, J=7 Hz, 2H), 2.73–2.81(m, 4H), 1.35(s, 18H)

IR (cm$^{-1}$) 3430, 3340, 2880, 1640, 1560, 1440, 1240, 750

EXAMPLE 37

N-[2-(3,5-di-tert-butyl-4-hydroxyphenethyl)phenyl]-N'-(1,2,3,4-tetrahydro-1-naphthyl)urea

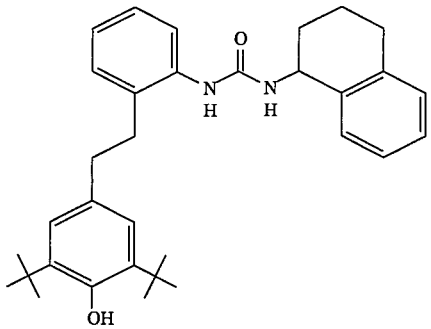

The title compound was prepared in a similar manner to that mentioned in Example 11, using 1,2,3,4-tetrahydro-1-naphthylamine instead of decylamine. m.p. 168°–169° C.

$^1$H-NMR (δ ppm, CDCl$_3$) 7.01–7.27(m, 8H), 6.77(s, 2H), 5.08(s, 1H), 5.01–5.06(m, 2H), 4.42(d, J=8 Hz, 1H), 2.65–2.90(m, 6H), 1.50–2.10(m, 4H), 1.35(s, 18H)

IR (cm$^{-1}$) 3650, 3350, 2960, 1640, 1560, 1440, 1240

EXAMPLE 38

N-[2-(3,5-di-tert-butyl-4-hydroxyphenethyl)phenyl]-N'-(2-ethylthioethyl)urea

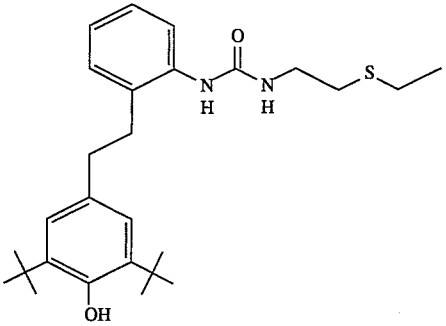

The title compound was prepared in a similar manner to that mentioned in Example 11, using 2-ethylthioethylamine instead of decylamine.

m.p. 131°–132° C.

$^1$H-NMR (δ ppm, CDCl$_3$) 7.19–7.28(m, 4H), 6.78(s, 2H), 5.12(s, 1H), 5.03(s, 1H), 4.63(t, J=6 Hz, 1H), 3.33(dt, J=6, 7 Hz, 2H), 2.80–2.85(m, 4H), 2.60(t, J=7 Hz, 2H), 2.48(q, J=7 Hz, 2H), 1.38(s, 18H), 1.20(t, J=7 Hz, 3H)

IR (cm$^{-1}$) 3570, 3320, 2950, 2920, 1640, 1570, 1440, 1250, 1240

EXAMPLE 39

N-[2-(3,5-di-tert-butyl-4-hydroxyphenethyl)phenyl]-N'-(3,9-dimethyl-3,9-diazabicyclo[3.3.1]-7-nonyl)urea

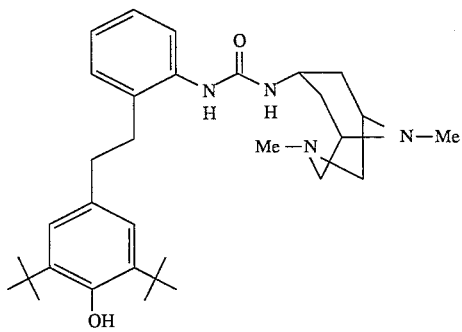

The title compound was prepared in a similar manner to that mentioned in Example 11, using 7-amino-3,9-dimethyl-3,9-diazabicyclo[3.3.1]nonane instead of decylamine.

$^1$H-NMR (δ ppm, CDCl$_3$) 8.55(d, J=10 Hz, 1H), 7.14–7.27(m, 4H), 6.85(s, 2H), 5.14(s, 1H), 5.09(s, 1H), 4.10–4.26(m, 1H), 2.87–2.90(m, 2H), 2.77–2.80(m, 2H), 2.70(bs, 2H), 2.41(s, 3H), 2.19–2.38(m, 7H), 1.39(s, 18H), 1.23–1.37(m, 4H)

IR(cm$^{-1}$) 3638, 2926, 1651, 1509, 1435, 1377, 733

EXAMPLE 40

N-[2-(3,5-di-tert-butyl-4-hydroxyphenethyl)phenyl]-N'-benzyl-N'-heptylurea

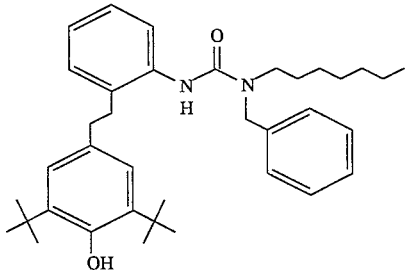

The title compound was prepared in a similar manner to that mentioned in Example 11, using N-heptylbenzylamine instead of decylamine.

$^1$H-NMR (δ ppm, CDCl$_3$) 7.7–7.75(m, 1H), 6.9–7.3(m, 8H), 6.78(s, 2H), 5.96(s, 1H), 5.06(s, 1H), 4.49(s, 2H), 3.30(t, J=8 Hz, 2H), 2.65–2.69(m, 2H), 2.51–2.54(m, 2H), 1.59–1.63(m, 2H), 1.38(s, 18H), 1.22–1.28(m, 8H), 0.86(t, J=7 Hz, 3H)

IR (cm$^{-1}$) 3640, 2960, 2940, 2870, 1660, 1530, 1460, 1440, 1240, 760

EXAMPLE 41

N-[2-(3,5-di-tert-butyl-4-hydroxyphenethyl)phenyl]-N'-heptyl-N'-methylurea

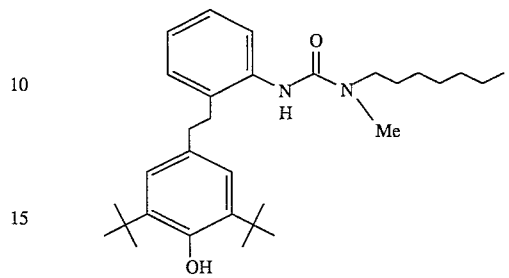

The title compound was prepared in a similar manner to that mentioned in Example 11, using N-methylheptylamine instead of decylamine.

$^1$H-NMR (δ ppm, CDCl$_3$) 7.36(d, J=8 Hz, 1H), 7.18–7.22(m, 2H), 7.07–2.10(m, 1H), 6.81(s, 2H), 5.66(s, 1H), 5.08(s, 1H), 3.23(t, J=8 Hz, 2H), 2.82(s, 4H), 2.71(s, 3H), 1.45–1.55(s, 2H), 1.36(s, 18H), 1.20–1.30(m, 8H), 0.86(t, J=7 Hz, 3H)

IR (cm$^{-1}$) 2880, 2870, 2820, 1660, 1520, 1490, 1450, 1440, 1250, 760

EXAMPLE 42

N-[2-(3,5-di-tert-butyl-4-hydroxyphenethyl)phenyl]-N',N'-dibenzylurea

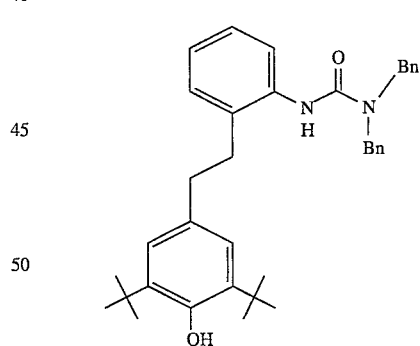

The title compound was prepared in a similar manner to that mentioned in Example 11, using N,N-dibenzylamine instead of decylamine.

$^1$H-NMR (δ ppm, CDCl$_3$) 7.69(d, J=8 Hz, 1H), 7.15–7.29(m, 10H), 7.00(m, 1H), 6.90(t, J=8 Hz, 1H), 6.80(d, J=8 Hz, 1H), 6.74(s, 2H), 6.01(bs, 1H), 5.05(s, 1H), 4.54(s, 4H), 2.59(t, J=8 Hz, 2H), 2.38(t, J=8 Hz, 2H), 1.37(s, 18H)

IR (cm$^{-1}$) 3628, 3280, 2958, 1710, 1645, 1594, 1498, 1475, 1362, 1231, 754, 696

EXAMPLE 43

N-[2-(3,5-di-tert-butyl-4-hydroxyphenethyl)phenyl]-N'-cyclohexyl-N'-methylurea

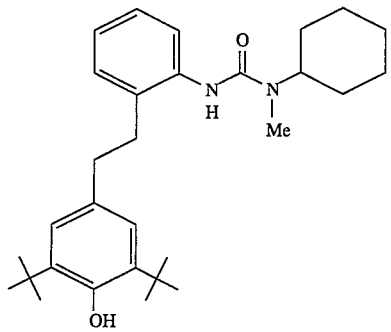

The title compound was prepared in a similar manner to that mentioned in Example 11, using N-methylcyclohexylamine instead of decylamine. Amorphous powders.

$^1$H-NMR (δ ppm, CDCl$_3$) 7.65(d, J=7 Hz, 1H), 7.15–7.21(m, 2H), 7.06(t, J=7 Hz, 1H), 6.81(s, 2H), 5.68(bs, 1H), 5.08(s, 1H), 4.13(m, 1H), 2.82(s, 4H), 2.54(s, 3H), 1.75–1.81(m, 2H), 1.60–1.75(m, 3H), 1.25–1.40(m, 23H)

IR (cm$^{-1}$) 3638, 3426, 2930, 1639, 1520, 1484, 1450, 1314, 1249, 1166, 1121, 751

EXAMPLE 44

N-[2-(3,5-di-tert-butyl-4-hydroxyphenethyl)phenyl]-N'-(9-anthryl)methyl-N'-methylurea

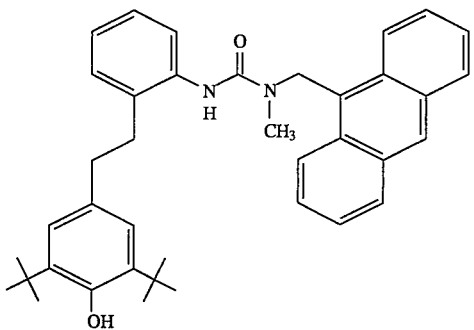

The title compound was prepared in a similar manner to that mentioned in Example 11, using 9-(methylaminomethyl)anthracene instead of decylamine.

m.p. 205°–206° C.

$^1$H-NMR (δ ppm, CDCl$_3$) 8.47(s, 1H), 8.37(d, J=9 Hz, 2H), 8.02–8.04(m, 8.02H), 7.70(d, J=8 Hz, 1H), 7.43–7.57 (m, 4H), 7.15–7.31(m, 3H), 6.67(s, 2H), 5.67(s, 1H), 5.59(s, 2H), 4.94(s, 1H), 2.76–2.86(m, 4H), 2.34(s, 3H), 1.19(s, 18H)

IR (cm$^{-1}$) 3420, 2950, 1640, 1520, 1490, 1450, 1440, 1250, 740

EXAMPLE 45

N-[2-(3,5-di-tert-butyl-4-hydroxyphenethyl)phenyl]-N',N'-dioctylurea

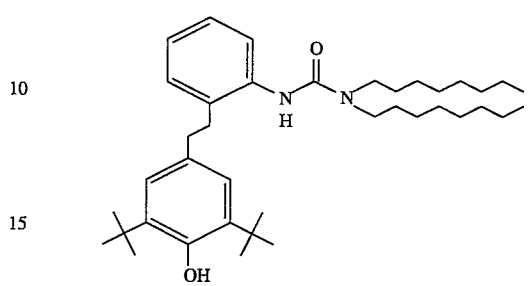

The title compound was prepared in a similar manner to that mentioned in Example 11, using N,N-dioctylamine instead of decylamine. m.p. 55°–60° C.

$^1$H-NMR (δ ppm, CDCl$_3$) 7.73(dd, J=8, 1 Hz, 1H), 7.13–7.25(m, 2H), 7.00–7.05(m, 1H), 6.85(s, 2H), 5.94(s, 1H), 5.07(s, 1H), 3.18(t, J=8 Hz, 4H), 2.81(s, 4H), 1.51–1.61(m, 4H), 1.39(s, 18H), 1.20–1.34(m, 20H), 0.87(t, J=7 Hz, 6H)

IR (cm$^{-1}$) 3646, 3420, 3322, 1626, 1511

EXAMPLE 46

N-[2-(3,5-di-tert-butyl-4-hydroxyphenethyl)phenyl]-N',N'-dicyclohexylurea

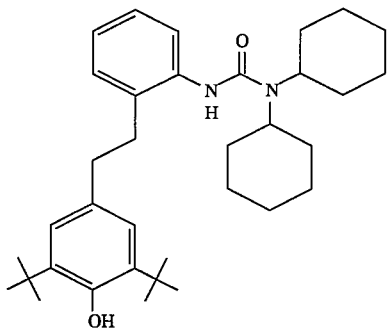

The title compound was prepared in a similar manner to that mentioned in Example 11, using N,N-dicyclohexylamine instead of decylamine.

m.p. 149°–152° C.

$^1$H-NMR (δ ppm, CDCl$_3$) 7.73(dd, J=8, 1 Hz, 1H), 7.15–7.20(m, 1H), 7.13(dd, J=7, 2 Hz, 1H), 7.00–7.05(m, 1H), 6.94(s, 2H), 6.15(s, 1H), 5.06(s, 1H), 3.42–3.52(m, 2H), 2.84(s, 4H), 1.55–1.83(m, 14H), 1.41(s, 18H), 1.22–1.34(m, 4H), 0.98–1.13(m, 2H)

IR (cm$^{-1}$) 3474, 3400, 1644, 1588, 1517

EXAMPLE 47

N-[2-(3,5-diisopropyl-4-hydroxyphenethyl)phenyl]-N'-heptylurea

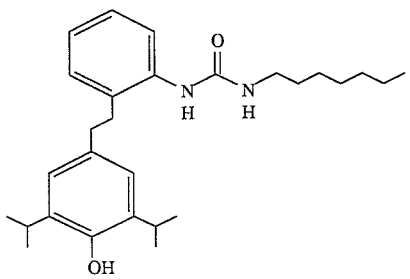

A solution of diphenylphosphoryl azide (0.88 g, 3.2 mmol), octanoic acid (0.42 g, 2.9 mmol) and triethylamine (0.32 g, 3.2 mmol) in toluene (10 ml) was stirred at room temperature for 1.5 hrs and further stirred at about 90° C. for 2 hrs. After allowing the mixture to cool, a solution of 4-(2-aminophenethyl)-2,6-diisopropylphenol (0.85 g, 2.9 mmol) in toluene (2 ml) was added dropwise under ice-cooling while stirring. The reaction solution was returned slowly to room temperature and stirred overnight. The solvent was distilled off, the residue was purified by a silica gel column chromatography and recrystallized from ethyl acetate/hexane to give crystals of the title compound (0.99 g, 76%). m.p. 150°–151° C.

$^1$H-NMR (δ ppm, CDCl$_3$) 7.16–7.26(m, 4H), 6.69(s, 2H), 5.14(s, 1H), 4.73(s, 1H), 4.18(t, J=6 Hz, 1H), 3.01–3.15(m, 4H), 2.71–2.89(m, 4H), 1.34–1.44(m, 2H), 1.2–1.3(m, 8H), 1.20,(s, 6H), 1.19(s, 6H), 0.86(t, J=7 Hz, 3H)

IR (cm$^{-1}$) 3330, 2960, 2930, 1640, 1580, 1470, 1450, 1260, 750

EXAMPLE 48

N-[2-(3,5-di-tert-butyl-4-hydroxystyryl)phenyl]-N'-heptylurea

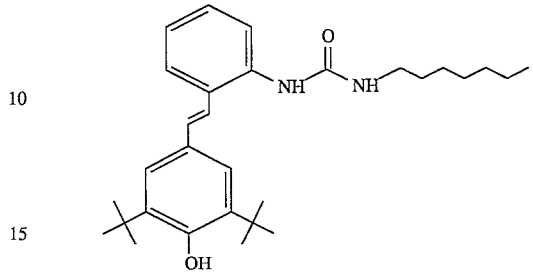

A solution of diphenylphosphoryl azide (0.36 g, 1.3 mmol), octanoic acid (0.17 g, 1.2 mmol) and triethylamine (0.13 g, 1.3 mmol) in toluene (5 ml) was stirred at room temperature for 1.5 hrs and further stirred at about 90° C. for 2 hrs. After allowing the mixture to cool, a solution of 4-(2-aminostyryl)-2,6-di-tert-butylphenol (0.89 g, 1.2 mmol) in toluene (2 ml) was added dropwise under ice-cooling while stirring. The reaction solution was returned slowly to room temperature and stirred overnight. The solvent was distilled off, the residue was purified by a silica gel column chromatography and recrystallized from ethyl acetate/hexane to give crystals of the title compound (0.39 g, 70%). m.p. 162°–164° C.

$^1$H-NMR (δ ppm, CDCl$_3$)7.63(dd, J=7, 2 Hz, 1H), 7.33–7.37(m, 3H), 7.21–7.28(m, 2H), 7.08(d, J=16 Hz, 1H), 7.01(d, J=16 Hz, 1H), 6.01(bs, 1H), 5.33(s, 1H), 4.54(t, J=6 Hz, 1H), 3.20(dt, J=6, 7 Hz, 2H), 1.42–1.47(m, 20H), 1.20–1.36(m, 8H), 0.83(t, J=7 Hz, 3H)

IR (cm$^{-1}$) 3626, 3334, 2954, 2926, 1642, 1568, 1454, 1439, 1235, 1152, 960, 751

EXAMPLE 49

N-[2-(3,5-di-tert-butyl-4-hydroxyphenethyl)phenyl]-N'-[2-(4-phenyl-1-piperadinyl)-5-pyridyl]urea

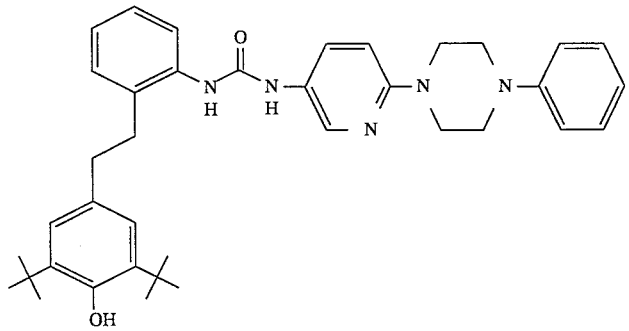

The title compound was prepared in a similar manner to that mentioned in Example 1, using 6-(4-phenyl-1-piperadinyl)nicotinic acid instead of 4-hexyloxybenzoic acid. m.p. 197°–199° C.

¹H-NMR(δ ppm, CDCl₃) 7.95(d, J=2 Hz, 1H), 7.67(dd, J=9, 2 Hz, 1H), 7.39(d, J=9 Hz, 1H), 7.17–7.33(m, 5H), 6.94–7.00(m, 2H), 6.89(dd, J=7, 7 Hz, 1H), 6.81(s, 2H), 6.65(d, J=9 Hz, 1H), 5.85(bs, 1H), 5.22(bs, 1H), 5.16(s, 1H), 3.62(t, J=5 Hz, 4H), 3.28(t, J=5 Hz, 4H), 2.76–2.92(m, 4H), 1.38(s, 18H)

IR (cm⁻¹) 3620, 3330, 3290, 2954, 1646, 1600, 1547, 1492, 1233, 951, 760

EXAMPLE 50

N-[2-(3,5-di-tert-butyl-4-hydroxyphenethyl)phenyl]-N'-(dicyclohexylmethyl)urea

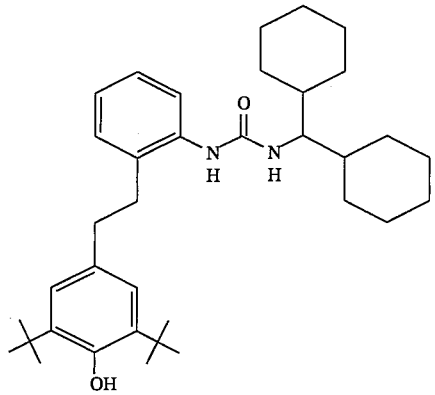

The title compound was prepared in a similar manner to that mentioned in Example 1, using dicyclohexylacetic acid instead of 4-hexyloxybenzoic acid.

m.p. 194°–195° C.

¹H-NMR(δ ppm, CDCl₃) 7.29–7.18(m, 4H), 6.81(s, 2H), 5.19(bs, 1H), 5.09(s, 1H), 4.00(d, J=10 Hz, 1H), 3.47(bs, 1H), 2.88(t, J=7 Hz, 2H), 2.80(t, J=7 Hz, 2H), 1.54–1.70(m, 10H), 1.38(s, 18H), 1.38–1.42(m, 2H), 1.01–1.19(m, 8H), 0.73–0.80(m, 2H)

IR(cm⁻¹) 3642, 3362, 2924, 2852, 1641, 1553, 1436, 1235, 744

EXAMPLE 51

N-[2-(3,5-di-tert-butyl-4-hydroxyphenethyl)phenyl]-N'-(6-oxoheptyl)urea

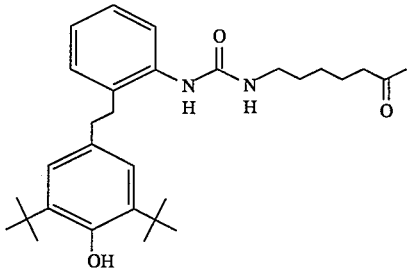

The title compound was prepared in a similar manner to that mentioned in Example 1, using 7-oxooctanoic acid instead of 4-hexyloxybenzoic acid. m.p. 73°–76° C.

¹H-NMR(δ ppm, CDCl₃) 7.16–7.25(m, 4H), 6.77(s, 2H), 5.12(s, 1H), 4.97(s, 1H), 4.17–4.24(m, 1H), 3.12(td, J=7, 6 Hz, 2H), 2.76–2.86(m, 4H), 2.38(t, J=7 Hz, 2H), 2.10(s, 3H), 1.49–1.57(m, 2H), 1.33–1.45(m, 4H), 1.37(s, 18H)

IR(cm⁻¹) 3368, 2950, 1712, 1632, 1574

EXAMPLE 52

N-[2-(3,5-di-tert-butyl-4-hydroxyphenethyl)phenyl]-N'-(4-tert-butylcyclohexyl)urea

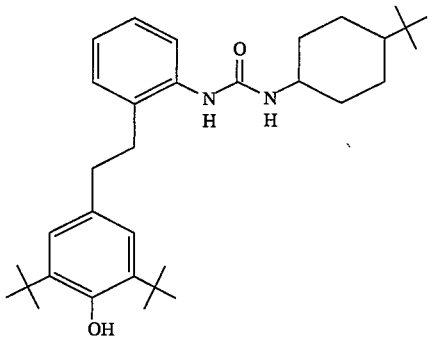

The title compound was prepared in a similar manner to that mentioned in Example 1, using 4-tert-butylcyclohexanecarboxylic acid instead of 4-hexyloxybenzoic acid. m.p. 206°–208° C.

¹H-NMR(δ ppm, CDCl₃) 7.15–7.25(m, 4H), 6.78(s, 2H), 5.10(s, 1H), 5.00(s, 1H), 4.02(d, J=8 Hz, 1H), 3.47–3.57(m, 1H), 2.76–2.86(m, 4H), 1.96–1.98(m, 2H), 1.70–1.73(m, 2H), 1.38(s, 18H), 0.84–1.13(m, 5H), 0.81(s, 9H)

IR(cm⁻¹) 3642, 3356, 2948, 1640, 1585, 1436, 1234

EXAMPLE 53

N-[2-(3,5-di-tert-butyl-4-hydroxyphenethyl)phenyl]-N'-cycloheptyl-N'-heptylurea

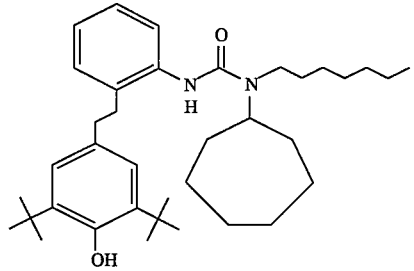

The title compound was prepared in a similar manner to that mentioned in Example 11, using N-heptylcycloheptylamine instead of decylamine. m.p. 70°–72° C.

¹H-NMR(δ ppm, CDCl₃) 7.77(dd, J=8, 1 Hz, 1H), 7.20(ddd, J=8, 8, 2 Hz, 1H), 7.13(dd, J=8, 1 Hz, 1H), 7.02(ddd, J=8, 8, 1 Hz, 1H), 6.89(s, 2H), 6.04(s, 1H), 5.06(s, 1H), 4.02(bs, 1H), 3.07–3.11(m, 2H), 2.82(s, 4H), 1.82–1.87(m, 2H), 1.58–1.70(m, 8H), 1.40–1.56(m, 4H), 1.40(s, 18H), 1.25(bs, 8H), 0.84–0.90(m, 3H)

IR(cm⁻¹) 3642, 3296, 2910, 1631, 1588, 1435, 1235, 751

EXAMPLE 54

N-[2-(3,5-di-tert-butyl-4-hydroxyphenethyl)phenyl]-
N'-benzyl-N'-cycloheptylurea

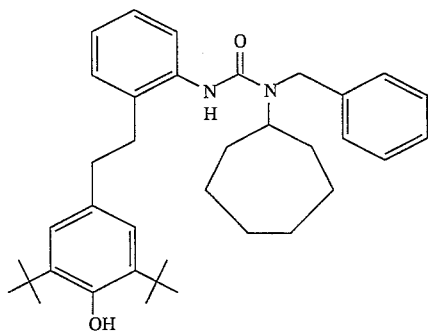

The title compound was prepared in a similar manner to that mentioned in Example 11, using benzylcycloheptylamine instead of decylamine. m.p. 183°–184° C.

$^1$H-NMR(δ ppm, CDCl$_3$) 7.74(d, J=8 Hz, 1H), 7.25–7.30(m, 2H), 7.07–7.21(m, 4H), 6.90–6.93(m, 2H), 6.76(s, 2H), 5.95(s, 1H), 5.06(s, 1H), 4.42–4.50(m, 1H), 4.43(s, 2H), 2.52(t, J=8 Hz, 2H), 2.23(t, J=8 Hz, 2H), 1.92–1.99(m, 2H), 1.43–1.72(s, 10H), 1.42(s, 18H)

IR(cm$^{-1}$) 3638, 3402, 2926, 1671, 1589, 1527, 1455, 1232, 1213, 752

EXAMPLE 55

N-[2-(3,5-di-tert-butyl-4-hydroxyphenethyl)phenyl]-
N'-[[1-(4-dimethylaminophenyl)cyclopentyl]methyl]
urea

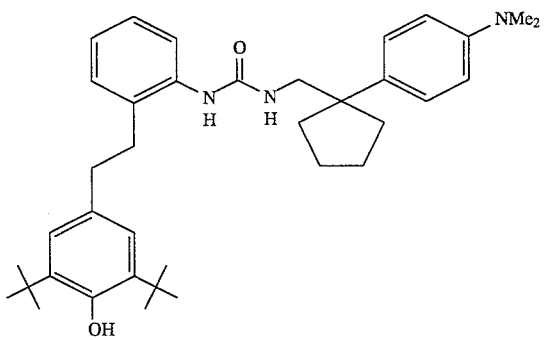

The title compound was prepared in a similar manner to that mentioned in Example 11, using 4-[1-(aminomethyl)cyclopentyl]-N,N-dimethylaniline instead of decylamine. m.p. 174°–175° C.

$^1$H-NMR(δ ppm, CDCl$_3$) 7.08–7.21(m, 3H), 7.03(d, J=7 Hz, 1H), 6.92 (d, J=9 Hz, 2H), 6.77 (s, 2H), 6.54(d, J=8 Hz, 2H), 5.07(s, 2H), 4.07–4.15(m, 1H), 3.22(d, J=5 Hz, 2H), 2.88(s, 6H), 2.69–2.79(m, 4H), 1.63–1.83(m, 8H), 1.36(s, 18H)

IR(cm$^{-1}$) 3640, 3360, 1644, 1525, 1435, 1233, 814, 749

EXAMPLE 56

N-[2-(3,5-di-tert-butyl-4-hydroxyphenethyl)phenyl]-
N'-(2-ethyl-1,3-dihydroxy-2-propyl)urea

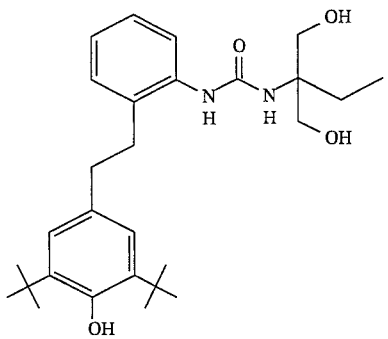

The title compound was prepared in a similar manner to that mentioned in Example 11, using 2-amino-2-ethyl-1,3-propanediol instead of decylamine. m.p. 145°–146° C.

$^1$H-NMR(δ ppm, CDCl$_3$) 7.16–7.31(m, 4H), 6.78(s, 2H), 5.12(s, 1H), 5.11(s, 1H), 4.61(s, 1H), 3.75–3.89(m, 4H), 3.46–3.55(m, 2H), 2.75–2.88(m, 4H), 1.51(q, J=8 Hz, 2H), 1.38(s, 18H), 0.75(t, J=8 Hz, 3H)

IR(cm$^{-1}$) 3640, 3570, 3400, 3340, 2970, 1660, 1610, 1560, 1440, 1250, 750, 650

EXAMPLE 57

N-[2-(3,5-di-tert-butyl-4-hydroxyphenethyl)phenyl]-
N'-(4-benzyloxycyclopropyl)urea

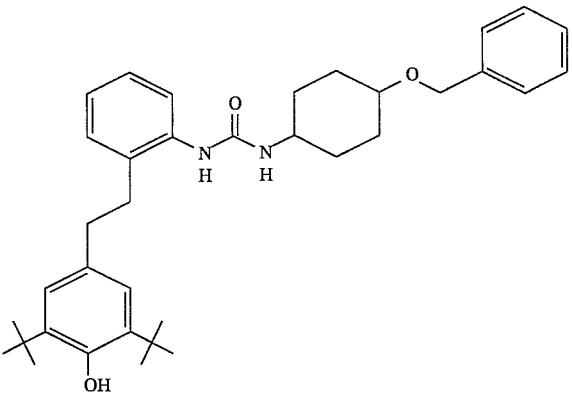

The title compound was prepared in a similar manner to that mentioned in Example 11, using 4-benzyloxycyclohexylamine instead of decylamine.

m.p. 152°–153° C.

$^1$H-NMR(δ ppm, CDCl$_3$) 7.16–7.36(m, 9H), 6.77(s, 2H), 5.11(s, 1H), 4.94(s, 1H), 4.51(s, 2H), 4.00(d, J=8 Hz, 1H), 3.56–3.68(m, 1H), 3.18–3.28(m, 1H), 2.74–2.86(m, 4H), 1.93–2.15(m, 4H), 1.31–1.47(m, 2H), 1.38(s, 18H), 0.94–1.08(m, 2H)

IR(cm$^{-1}$) 3630, 3370, 3330, 2950, 1645, 1565, 1235, 1090,

EXAMPLE 58

N-[2-(3,5-di-tert-butyl-4-hydroxyphenethyl)phenyl]-N'-(2-ethoxycarbonylethyl)urea

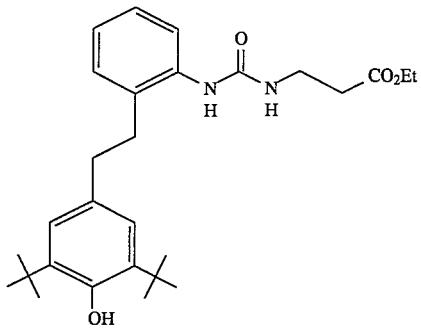

The title compound was prepared in a similar manner to that mentioned in Example 11, using ethyl 3-aminopropionate instead of decylamine. m.p. 158°–159° C.

$^1$H-NMR($\delta$ ppm, CDCl$_3$) 7.14–7.28(m, 4H), 6.78(s, 2H), 5.12(s, 1H), 5.08(s, 1H), 4.75(t, J=6 Hz, 1H), 4.07(q, J=7 Hz, 2H), 3.41(dt J=6, 6 Hz, 1H), 2.74–2.86(m, 4H), 2.49(t, J=6 Hz, 2H), 1.38(18H.s, 18H), 1.18(t, J=7 Hz, 3H)

IR(cm$^{-1}$) 3630, 3320, 3270, 2960, 1730, 1630, 1570, 1440, 1235, 1190, 745

EXAMPLE 59

N-[2-(3,5-di-tert-butyl-4-hydroxyphenethyl)phenyl]-N'-(4-aminocyclohexyl)urea

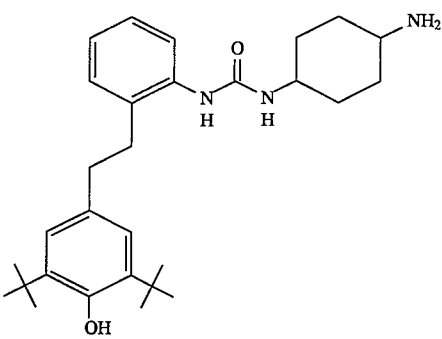

The title compound was prepared in a similar manner to that mentioned in Example 11, using 1,4-diaminocyclohexane instead of decylamine.

m.p. >280° C. (dec.)

$^1$H-NMR($\delta$ ppm, CDC$_3$) 7.14–7.28(m, 4H), 6.77(s, 2H), 5.12(bs, 1H), 4.97(bs, 1H), 3.98–4.05(m, 1H), 3.53–3.64(m, 1H), 2.74–2.87(m, 4H), 2.52–2.62(m, 1H), 1.89–1.97(m, 2H), 1.77–1.86(m, 2H), 1.38(s, 18H), 0.97–1.24(m, 4H)

IR(cm$^{-1}$) 3630, 3420, 3340, 2940, 1635, 1590, 1570, 1240, 935

EXAMPLE 60

N-[2-(3,5-di-tert-butyl-4-hydroxyphenethyl)phenyl]-N'-(4-acetamidocyclohexyl)urea

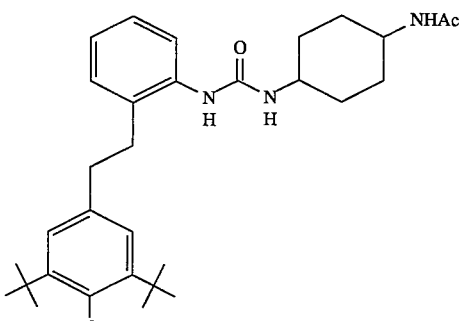

The title compound was prepared in a similar manner to that mentioned in Example 11, using N-(4-aminocyclohexyl)acetamide instead of decylamine.

m.p. 250° C. (dec.)

$^1$H-NMR($\delta$ ppm, CDCl$_3$) 7.16–7.30(m, 4H), 6.77(s, 2H), 5.26(bd, J=8 Hz, 1H), 5.11(s, 1H), 4.93(s, 1H), 4.05(d, J=8 Hz, 1H), 3.54–3.73(m, 2H), 2.74–2.87(m, 4H), 1.92–2.00(m, 4H), 1.93(s, 3H), 1.37(s, 18H), 1.03–1.27(m, 4H)

IR(cm$^{-1}$) 3640, 3290, 2950, 1635, 1550, 1440, 1235, 760

EXAMPLE 61

N-[2-(3,5-di-tert-butyl-4-hydroxyphenethyl)phenyl]-N'-(4-hydroxycyclohexyl)urea

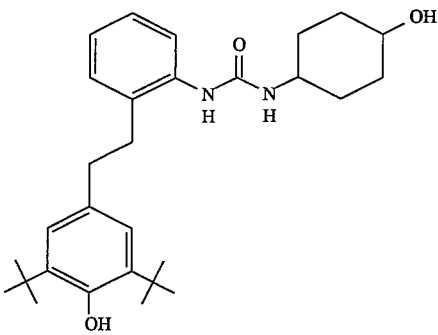

The title compound was prepared in a similar manner to that mentioned in Example 11, using 4-aminocyclohexanol instead of decylamine. m.p. 202°–203° C.

$^1$H-NMR($\delta$ ppm, CDCl$_3$) 7.17–7.29(m, 4H), 6.77(s, 2H), 5.12(s, 1H), 4.94(s, 1H), 3.99(d, J=8 Hz, 1H), 3.43–3.69(m, 2H), 2.75–2.87(m, 4H), 1.87–2.01(m, 4H), 1.28–1.43(m, 2H), 1.38(s, 18H), 0.97–1.12(m, 2H)

IR(cm$^{-1}$) 3645, 3320, 2950, 1640, 1570, 1440, 1235, 1070, 880, 745

EXAMPLE 62

N-[2-(3,5-di-tert-butyl-4-hydroxyphenethyl)phenyl]-N'-(4-acetoxycyclohexyl)urea

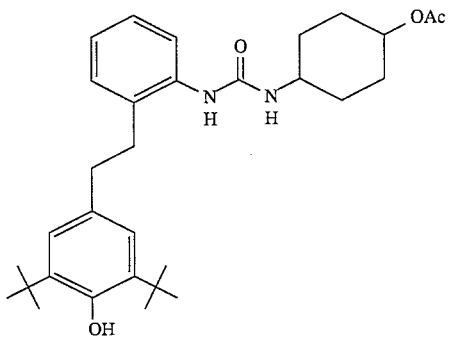

The title compound was prepared in a similar manner to that mentioned in Example 11, using 4-aminocyclohexyl acetate instead of decylamine. m.p. 92°–94° C.

$^1$H-NMR($\delta$ ppm, CDCl$_3$) 7.17–7.28(m, 4H), 6.77(s, 2H), 5.12(s, 1H), 4.93(s, 1H), 4.53–4.64(m, 1H), 4.02(d, J=8 Hz, 1H), 3.57–3.71(m, 1H), 2.78–2.87(m, 4H), 2.01(s, 3H), 1.87–2.02(m, 4H), 1.32–1.52(m, 2H), 1.38(s, 18H), 1.02–1.16(m, 2H)

IR(cm$^{-1}$) 3640, 3380, 2960, 1740, 1645, 1560, 1440, 1245, 1050, 765

EXAMPLE 63

N-[2-(3,5-di-tert-butyl-4-hydroxyphenethyl)phenyl]-N'-(3-pyridylmethyl)urea

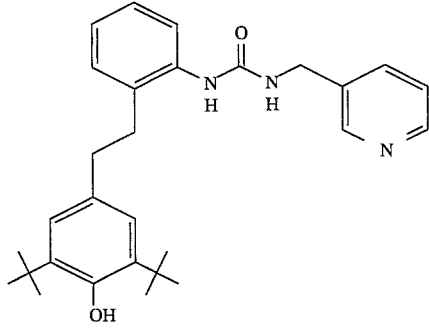

The title compound was prepared in a similar manner to that mentioned in Example 11, using 3-(aminomethyl)pyridine instead of decylamine. m.p. 163°–164° C.

$^1$H-NMR($\delta$ ppm, CDCl$_3$) 8.48(dd, J=5, 1 Hz, 1H), 8.45(d, J=2 Hz, 1H), 7.58(d, J=8 Hz, 1H), 7.18–7.27(m, 5H), 6.75(s, 2H), 5.12(s, 1H), 4.95(s, 1H), 4.45–4.50(m, 1H), 4.34(d, J=6 Hz, 2H), 2.75–2.86(m, 4H), 1.35(s, 18H)

IR(cm$^{-1}$) 3294, 1634, 1574, 1430, 1239, 1119, 760, 712

EXAMPLE 64

N-[2-(3,5-di-tert-butyl-4-hydroxyphenethyl)phenyl]-N'-(4-pyridylmethyl)urea

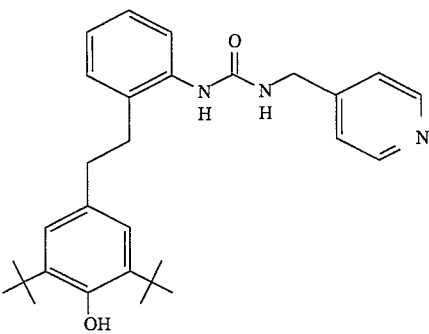

The title compound was prepared in a similar manner to that mentioned in Example 11, using 4-(aminomethyl)pyridine instead of decylamine. m.p. 214°–215° C.

$^1$H-NMR($\delta$ ppm, CDCl$_3$) 8.50(dd, J=4, 1 Hz, 2H), 7.30–7.25(m, 2H), 7.20–7.24(m, 2H), 7.12(d, J=6 Hz, 2H), 6.77(s, 2H), 5.13(s, 1H), 5.00(s, 1H), 4.54(t, J=6 Hz, 1H), 4.34(d, J=6 Hz, 2H), 2.86–2.90(m, 2H), 2.79–2.82(m, 2H), 1.35(s, 18H)

IR(cm$^{-1}$) 3292, 1632, 1573, 1436, 1237, 761

EXAMPLE 65

N-[2-(3,5-di-tert-butyl-4-hydroxyphenethyl)phenyl]-N'-(2-pyridylmethyl)urea

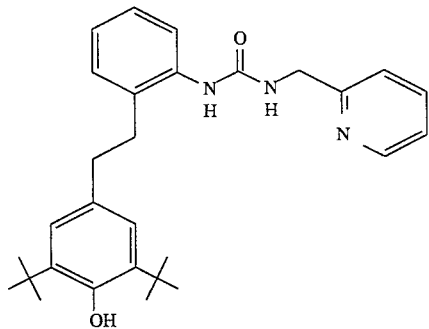

The title compound was prepared in a similar manner to that mentioned in Example 11, using 2-(aminomethyl)pyridine instead of decylamine. m.p. 189°–190° C.

$^1$H-NMR($\delta$ ppm, CDCl$_3$) 8.42(dd, J=4, 1 Hz, 1H), 7.61 (ddd, J=8, 8, 2 Hz, 1H), 7.38(dd, J=8, 1 Hz, 1H), 7.12–7.24(m, 5H), 6.80(s, 2H), 5.48(bs, 1H), 5.36(t, J=5 Hz, 1H), 5.29(s, 1H), 4.47(d, J=6 Hz, 2H), 2.78–2.89(m, 4H), 1.36(s, 18H)

IR(cm$^{-1}$) 3632, 3612, 3296, 1627, 1576, 1437, 1234, 755

EXAMPLE 66

N-[2-(3,5-di-tert-butyl-4-hydroxyphenethyl)phenyl]-
N'-ethyl-N'-(4-pyridylmethyl)urea

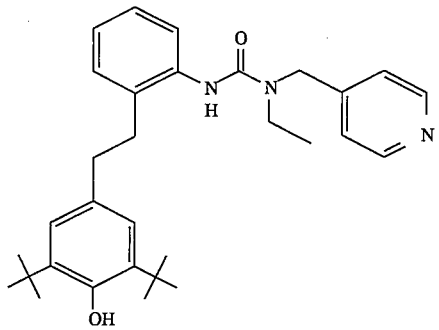

The title compound was prepared in a similar manner to that mentioned in Example 11, using 4-(ethylaminomethyl)pyridine instead of decylamine.

$^1$H-NMR($\delta$ ppm, CDCl$_3$) 8.51(dd, J=4, 1 Hz, 2H), 7.66(dd, J=8, 1 Hz, 1H), 7.09–7.25(m, 5H), 6.79(s, 2H), 5.85(s, 1H), 5.09(s, 1H), 4.50(s, 2H), 3.09(q, J=7 Hz, 2H), 2.74–2.82(m, 4H), 1.36(s, 18H), 1.14(t, J=7 Hz, 3H)

IR(cm$^{-1}$) 3266, 3060, 1630, 1606, 1516, 1492, 1451, 1431, 1269, 755, 746

EXAMPLE 67

N-[2-(3,5-di-tert-butyl-4-hydroxyphenethyl)phenyl]-
N'-(8-methyl-8-azabicyclo[3.2.1]-3-octyl)urea

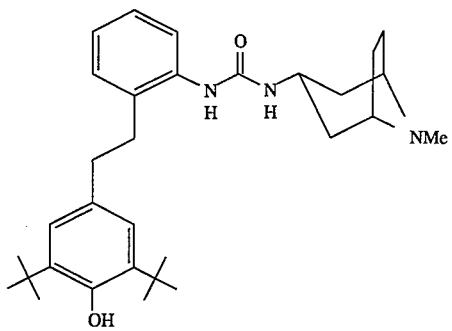

The title compound was prepared in a similar manner to that mentioned in Example 11, using 3-amino-8-methyl-8-azabicyclo[3.2.1]octane instead of decylamine.

m.p. 229°–230° C.

$^1$H-NMR($\delta$ ppm, CDCl$_3$) 7.27(d, J=4 Hz, 1H), 7.13–7.21(m, 3H), 6.79(s, 2H), 5.51(bs, 1H), 5.14(s, 1H), 4.77(bs, 1H), 4.07–4.13(m, 1H), 3.51(bs, 2H), 2.76–2.87(m, 4H), 2.51(s, 3H), 2.13–2.15(m, 2H), 1.89–1.96(m, 6H), 1.38(m, 18H)

IR(cm$^{-1}$) 3360, 1645, 1565, 1435, 1240, 745

EXAMPLE 68

N-[2-(3,5-di-tert-butyl-4-hydroxyphenethyl)phenyl]-
N'-(2-pyridylmethyl)-N'-(3-pyridylmethyl)urea

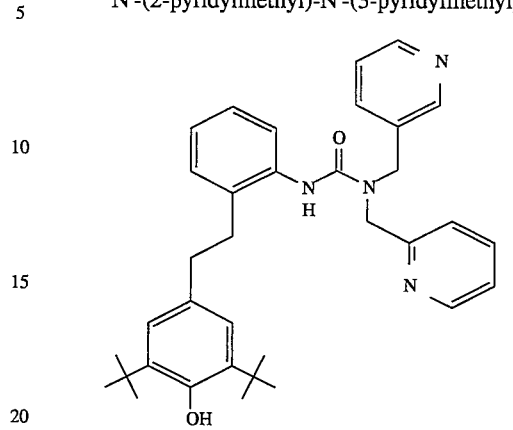

The title compound was prepared in a similar manner to that mentioned in Example 11, using N-(3-pyridylmethyl)-2-pyridylmethylamine instead of decylamine.

$^1$H-NMR($\delta$ ppm, CDCl$_3$) 9.47(s, 2H), 8.52(d, J=4 Hz, 1H), 8.48(dd, J=5, 1 Hz, 1H), 7.89(d, J=6 Hz, 1H), 7.76(dd, J=8, 1 Hz, 1H), 7.67 (ddd, J=8, 8, 2 Hz, 1H), 7.54(dd, J=8, 2 Hz, 1H), 7.23(t, J=7 Hz, 2H), 7.14–7.18(m, 1H), 7.02–7.06(m, 2H), 6.97(d, J=8 Hz, 1H), 6.93(s, 2H), 5.19(s, 1H), 4.60(s, 2H), 4.37(s,2H), 2.96–3.05(m, 2H), 2.90–2.94(m, 2H), 1.35(s, 18H)

IR(cm$^{-1}$) 3632, 3250, 1661, 1591, 1533, 1480, 1436, 1393, 1362, 1295, 1214, 755

EXAMPLE 69

(S)-N-[2-(3,5-di-tert-butyl-4-hydroxyphenethyl)phenyl]-N'-($\alpha$-ethoxycarbonyl)benzylurea

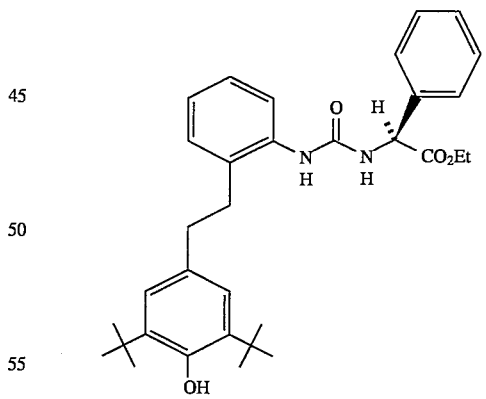

The title compound was prepared in a similar manner to that mentioned in Example 11, using (S)-$\alpha$-phenylglycine ethyl ester instead of decylamine.

$^1$H-NMR($\delta$ ppm, CDCl$_3$) 7.44(d, J=8 Hz, 1H), 7.19–7.33(m, 8H), 6.78(s, 2H), 5.90(s, 1H), 5.74(d, J=7 Hz, 1H), 5.59(d, J=8 Hz, 1H), 5.16(s, 1H), 4.10–4.24(m, 2H), 2.89–2.92(m, 2H), 2.82–2.85(m, 2H), 1.43(s, 18H), 1.21(t, J=7 Hz, 3H)

IR(cm$^{-1}$) 3636, 3294, 1737, 1643, 1542, 1435, 1233, 754

EXAMPLE 70

N-[2-(3,5-di-tert-butyl-4-hydroxyphenethyl)phenyl]-N'-(1-methyl-3-piperidyl)urea

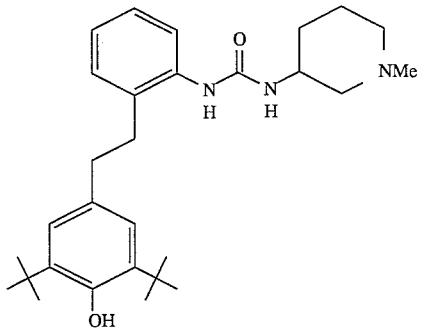

The title compound was prepared in a similar manner to that mentioned in Example 11, using 3-amino-1-methylpiperidine instead of decylamine.

$^1$H-NMR($\delta$ ppm, CDCl$_3$) 7.45(d, J=8 Hz, 1H), 7.16–7.26(m, 3H), 6.92(s, 2H), 6.35(bs, 1H), 5.40(bs, 1H), 5.17(s, 1H), 3.45(bs, 1H), 3.18–3.23(m, 1H), 2.93–3.01(m, 1H), 2.83–2.92(m, 4H), 2.45–2.51(m, 1H), 2.34(s, 3H), 2.18–2.27(m, 1H), 1.82–1.95(m, 1H), 1.60–1.73(m, 3H), 1.46(s, 18H)

IR(cm$^{-1}$) 3638, 3250, 1643, 1548, 1436, 1235, 910, 733

EXAMPLE 71

N-[2-(3,5-di-tert-butyl-4-hydroxyphenethyl)phenyl]-N'-benzyl-N'-(2-pyridylmethyl)urea

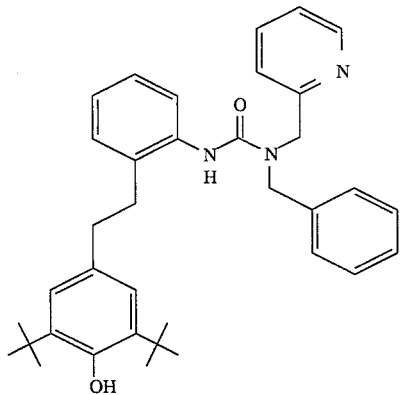

The title compound was prepared in a similar manner to that mentioned in Example 11, using N-benzyl-2-pyridylmethylamine instead of decylamine.

$^1$H-NMR($\delta$ ppm, CDCl$_3$) 9.20(bs, 1H), 7.92(d, J=4 Hz, 1H), 7.78(d, J=7 Hz, 1H), 7.52(ddd, J=8, 8, 2 Hz, 1H), 7.19–7.30(m, 7H), 7.01–7.05(m, 2H), 6.93(s, 2H), 6.92–6.94(m, 1H), 5.06(s, 1H), 4.60(s, 2H), 4.41(s, 2H), 2.88–3.00(m, 4H), 1.36(s, 18H)

IR(cm$^{-1}$) 3620, 3250, 2244, 1657, 1590, 1532, 1453, 1436, 1213, 752, 732

EXAMPLE 72

N-[2-(3,5-di-tert-butyl-4-hydroxyphenethyl)phenyl]-N'-($\alpha$-ethoxycarbonyl)benzylurea

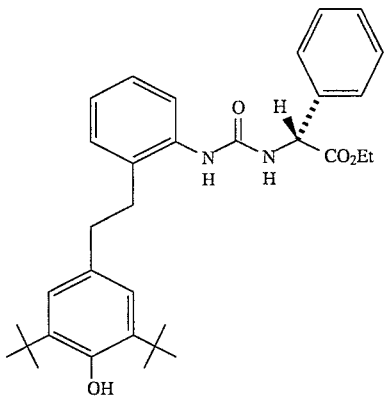

The title compound was prepared in a similar manner to that mentioned in Example 11, using (R)-$\alpha$-phenylglycine ethyl ester instead of decylamine.

$^1$H-NMR($\delta$ ppm, CDCl$_3$) 7.18–7.35(m, 9H), 6.77(s, 2H), 5.50(d, J=8 Hz, 1H), 5.37(d, J=8 Hz, 1H), 5.33(s, 1H), 5.09(s, 1H), 4.07–4.18(m, 2H), 2.78–2.84(m, 4H), 1.35(s, 18H), 1.17(t, J=7 Hz, 3H)

IR(cm$^{-1}$) 3636, 3330, 1739, 1640, 1542, 1436, 1234, 1180, 935, 751, 698

EXAMPLE 73

N-[2-(3,5-di-tert-butyl-4-hydroxyphenethyl)phenyl]-N'-(1-azabicyclo[2.2.2]-3-octyl)urea

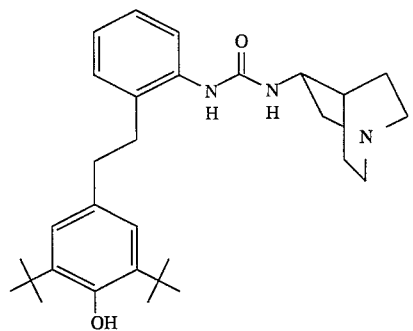

The title compound was prepared in a similar manner to that mentioned in Example 11, using 3-amino-1-azabicyclo[2.2.2]octane instead of decylamine.

m.p. 227°–229° C.

$^1$H-NMR($\delta$ ppm, CDCl$_3$) 7.21–7.27(m, 4H), 6.77(s, 2H), 5.11(s, 1H), 5.07(s, 1H), 4.43(d, J=7 Hz, 1H), 3.78–3.85(m, 1H), 3.28(ddd, J=14, 10, 2 Hz, 1H), 2.65–2.89(m, 8H), 2.29–2.33(m, 1H), 1.85–1.87(m, 1H), 1.55–1.70(m, 4H), 1.38(s, 18H)

IR(cm$^{-1}$) 3636, 3368, 3260, 1640, 1587, 1564, 1434, 1237, 1122, 765, 753

EXAMPLE 74

N-[2-(3,5-di-tert-butyl-4-hydroxyphenethyl)phenyl]-N'-[2-(3,4-dichlorophenyl)-2-propyl]urea

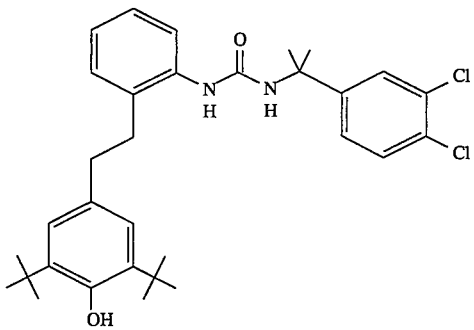

The title compound was prepared in a similar manner to that mentioned in Example 11, using 3,4-dichloro-α,α-dimethylbenzylamine instead of decylamine.

m.p. 203°–205° C.

$^1$H-NMR(δ ppm, CDCl$_3$) 7.41(d, J=2 Hz, 1H), 7.16–7.32(m, 6H), 6.81(s, 2H), 5.17(s, 1H), 5.11(s, 1H), 4.60(s, 1H), 2.79–2.83(m, 4H), 1.56(s, 6H), 1.39(s, 18H)

IR(cm$^{-1}$) 3638, 3352, 3282, 1644, 1564, 1558, 1437, 1235, 1171, 1030, 768, 745

EXAMPLE 75

N-[2-(3,5-di-tert-butyl-4-hydroxyphenethyl)phenyl]-N'-(4-dimethylaminophenethyl)urea

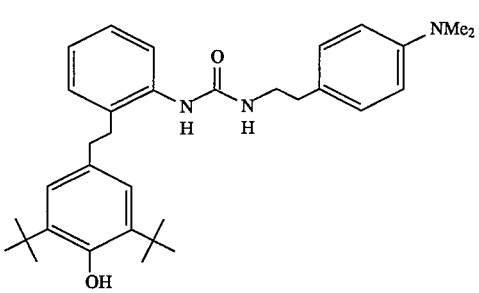

The title compound was prepared in a similar manner to that mentioned in Example 11, using 4-dimethylaminophenethylamine instead of decylamine.

$^1$H-NMR(δ ppm, CDCl$_3$) 7.11–7.24(m, 4H), 6.96(d, J=9 Hz, 2H), 6.77(s, 2H), 6.62(s, 2H), 5.09(s, 1H), 5.08(s, 1H), 4.03(t, J=6 Hz, 1H), 3.33(td, J=7, 6 Hz, 2H), 2.89(s, 6H), 2.72–2.86(m, 4H), 2.64(t, J=7 Hz, 2H), 1.37(s, 18H)

IR(cm$^{-1}$) 3640, 3342, 2940, 1640, 1562, 1521, 1439, 660, 643

EXAMPLE 76

N-[2-(3,5-di-tert-butyl-4-hydroxyphenethyl)phenyl]-N'-[[1-(3,4-methylenedioxyphenyl)cyclopentyl]methyl]urea

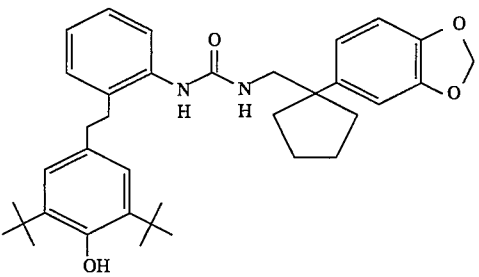

The title compound was prepared in a similar manner to that mentioned in Example 11, using 5-[1-(aminomethyl)cyclopentyl]-1,3-dioxaindane instead of decylamine. m.p. 188°–189° C.

$^1$H-NMR(δ ppm, CDCl$_3$) 7.12–7.22(m, 3H), 7.03(d, J=7 Hz, 1H), 6.75(s, 2H), 6.59(d, J=2 Hz, 1H), 6.57(d, J=8 Hz, 1H), 6.47(dd, J=8, 2 Hz, 1H), 5.88(s, 2H), 5.08(s, 1H), 5.00(s, 1H), 3.95–4.00(m, 1H), 3.21(d, J=5 Hz, 2H), 2.70–2.80(m, 4H), 1.55–1.85(m, 8H), 1.36(s, 18H)

IR(cm$^{-1}$) 3640, 3388, 3328, 1645, 1561, 1488, 1435, 1363, 1234, 1042, 940, 760

EXAMPLE 77

N-[2-(3,5-di-tert-butyl-4-hydroxyphenethyl)phenyl]-N'-[2-(3,4-dichlorophenyl)-2-methylpropyl]urea

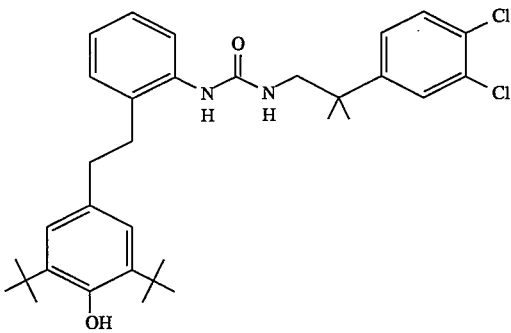

The title compound was prepared in a similar manner to that mentioned in Example 11, using 3,4-dichloro-β,β-dimethylphenethylamine instead of decylamine.

m.p. 165°–167° C.

$^1$H-NMR(δ ppm, CDCl$_3$) 6.95–7.29(m, 7H), 6.73(s, 2H), 5.09(s, 1H), 4.90–5.00(m, 1H), 3.96(bs, 1H), 3.29(d, J=6 Hz, 2H), 2.65–2.75(m, 4H), 1.35(s, 18H), 1.23(s, 6H)

IR(cm$^{-1}$) 3638, 3364, 1646, 1587, 1563, 1475, 1437, 1235, 762

EXAMPLE 78

N-[2-(3,5-di-tert-butyl-4-hydroxyphenethyl)phenyl]-N'-methyl-N'-(1-methyl-4-piperidyl)urea

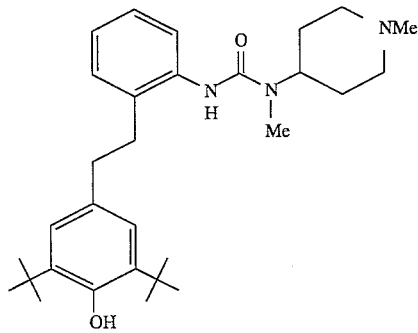

The title compound was prepared in a similar manner to that mentioned in Example 11, using 1-methyl-4-(methylamino)piperidine instead of decylamine.

$^1$H-NMR($\delta$ ppm, CDCl$_3$) 7.63(d, J=7 Hz, 1H), 7.19–7.26(m, 2H), 7.10(ddd, J=7, 7; 1 Hz, 1H), 6.79(s, 2H), 5.63(s, 1H), 5.08(s, 1H), 4.20–4.27(m, 1H), 2.85–2.90(m, 2H), 2.82(s, 4H), 2.48(s, 3H), 2.28(s, 3H), 1.98–2.07(m, 2H), 1.55–1.90(m, 4H), 1.35(s, 18H)

IR(cm$^{-1}$) 3424, 1638, 1511, 1484, 1450, 1436, 1287, 1042, 754

EXAMPLE 79

N-[2-(3,5-di-tert-butyl-4-hydroxyphenethyl)phenyl]-N'-(4-fluorophenethyl)urea

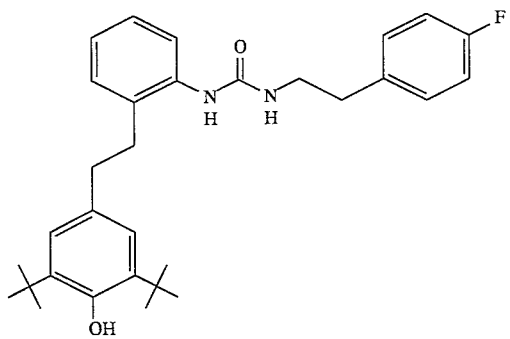

The title compound was prepared in a similar manner to that mentioned in Example 11, using 4-fluorophenethylamine instead of decylamine. m.p. 177°–179° C.

$^1$H-NMR($\delta$ ppm, CDCl$_3$) 7.03–7.26(m, 6H), 6.89–6.93(m, 2H), 6.76(m, 2H), 5.10(s, 1H), 4.94(s, 1H), 4.15–4.20(m, 1H), 3.35(q, J=7 Hz, 2H), 2.76–2.82(m, 4H), 2.71(t, J=7 Hz, 2H), 1.36(s, 18H)

IR(cm$^{-1}$) 3636, 3348, 1643, 1563, 1511, 1438, 1234, 831, 747

EXAMPLE 80

N-[2-(3,5-di-tert-butyl-4-hydroxyphenethyl)phenyl]-N'-[1-(2,4-difluorobenzyl)-4-pyperidyl]urea

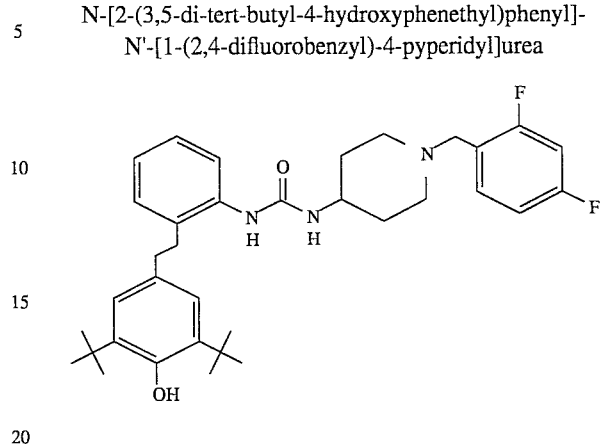

The title compound was prepared in a similar manner to that mentioned in Example 11, using 4-amino-1-(2,4-difluorobenzyl)pyperidine instead of decylamine.

m.p. 157°–158° C.

$^1$H-NMR($\delta$ ppm, CDCl$_3$) 7.15–7.36(m, 5H), 6.89–6.72(m, 4H), 5.11(s, 1H), 4.97(s, 1H), 4.09(d, J=8 Hz, 1H), 3.57–3.72(m, 1H), 3.47(s, 2H), 2.68–2.88(m, 6H), 2.14–2.20(m, 2H), 1.82–1.95(m, 2H), 1.58–1.74(m, 2H), 1.20–1.40(m, 2H), 1.37(s, 18H)

IR(cm$^{-1}$) 3640, 3370, 3250, 2960, 1690, 1650, 1590, 1565, 1505, 1235, 850, 760

EXAMPLE 81

N-[2-(3,5-di-tert-butyl-4-hydroxyphenethyl)phenyl]-N'-[1-(4-methoxybenzyl)-4-piperidyl]urea

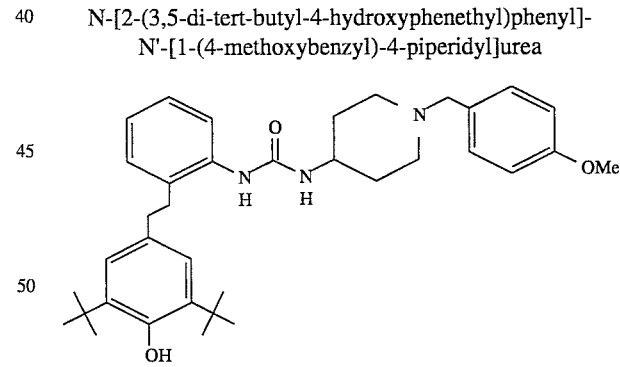

The title compound was prepared in a similar manner to that mentioned in Example 11, using 4-amino-1-(4-methoxybenzyl)piperidine instead of decylamine.

m.p. 152°–153° C.

$^1$H-NMR($\delta$ ppm, CDCl$_3$) 7.14–7.30(m, 6H), 6.74–6.88(m, 4H), 5.11(s, 1H), 4.97(s, 1H), 4.09(d, J=8 Hz, 1H), 3.79(s, 3H), 3.56–3.72(m, 1H), 3.38(s, 2H), 2.67–2.88(m, 6H), 1.96–2.09(m, 2H), 1.82–1.92(m, 2H), 1.37(s, 18H), 1.18–1.35(m, 2H)

IR(cm$^{-1}$) 3640, 3360, 3260, 2950, 1645, 1595, 1565, 1515, 1245, 1045, 760

EXAMPLE 82

N-[2-(3,5-di-tert-butyl-4-hydroxyphenethyl)phenyl]-N'-(1-phenethyl-4-piperidyl)urea

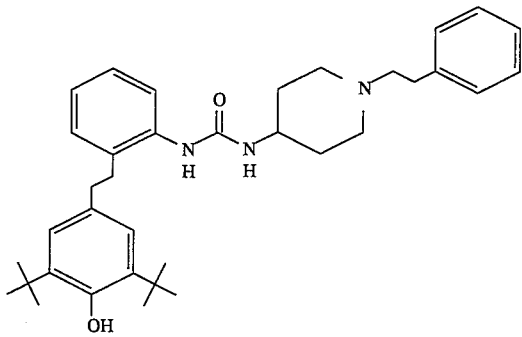

The title compound was prepared in a similar manner to that mentioned in Example 11, using 4-amino-1-phenethylpiperidine instead of decylamine. m.p. 175°–176° C.

$^1$H-NMR($\delta$ ppm, CDCl$_3$) 7.15–7.31(m, 9H), 6.78(s, 2H), 5.12(s, 1H), 5.01(s, 1H), 4.13(d, J=8 Hz, 3.58–3.73(m, 1H), 2.72–2.91(m, 8H), 2.50–2.57(m, 2H), 2.05–2.16(m,2H), 1.38(s, 18H), 1.24–1.35(m, 2H)

IR(cm$^{-1}$) 3640, 3340, 2950, 1640, 1590, 1565, 1435, 1235, 770, 750, 700

EXAMPLE 83

N-[2-(3,5-di-tert-butyl-4-hydroxyphenethyl)phenyl]-N'-[1-(4-fluorobenzyl)-4-piperidyl]urea

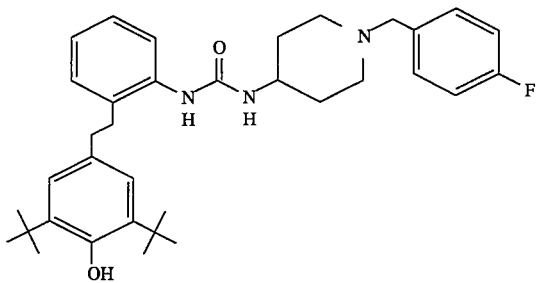

The title compound was prepared in a similar manner to that mentioned in Example 11, using 4-amino-1-(4-fluorobenzyl)piperidine instead of decylamine.

m.p. 174°–175° C.

$^1$H-NMR($\delta$ ppm, CDCl$_3$) 7.16–7.29(m, 6H), 6.93–7.00(m, 2H), 6.77(s, 2H), 5.11(s, 1H), 4.97(s, 1H), 4.09(d, J=8 Hz, 1H), 3.57–3.71(m, 1H), 3.39(s, 2H), 2.66–2.87(m, 6H), 1.98–2.08(m, 2H), 1.82–1.90(m, 2H), 1.37(s, 18H), 1.22–1.34(m, 2H)

IR(cm$^{-1}$) 3645, 3370, 2950, 1540, 1590, 1560, 1510, 1225, 750

EXAMPLE 84

N-[2-(3,5-di-tert-butyl-4-hydroxyphenethyl)phenyl]-N'-[1-(4-cyanobenzyl)-4-piperidyl]urea

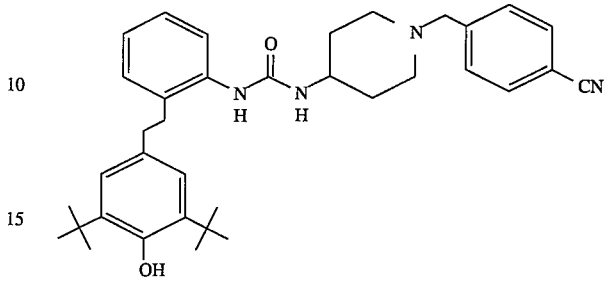

The title compound was prepared in a similar manner to that mentioned in Example 11, using 4-amino-1-(4-cyanobenzyl)piperidine instead of decylamine. m.p. 197°–198° C.

$^1$H-NMR($\delta$ ppm, CDCl$_3$) 7.58(d, J=8 Hz, 2H), 7.40(d, J=8 Hz, 2H), 7.17–7.29(m, 4H), 6.77(s, 2H), 5.12(s, 1H), 4.97(s, 1H), 4.10(d, J=8 Hz, 1H), 3.59–3.72(m, 1H), 3.48(s, 2H), 2.75–2.87(m, 4H), 2.64–2.73(m, 2H), 2.03–2.13(m, 2H), 1.83–1.91(m, 2H), 1.37(s, 18H), 1.23–1.35(m, 2H)

IR(cm$^{-1}$) 3580, 3355, 3250, 2960, 2240, 1645, 1590, 1560, 1235, 825, 765, 550

EXAMPLE 85

N-[2-(3,5-di-tert-butyl-4-hydroxyphenethyl)phenyl]-N'-[1[-2,4-bis(trifluoromethyl)benzyl]-4-piperidyl]urea

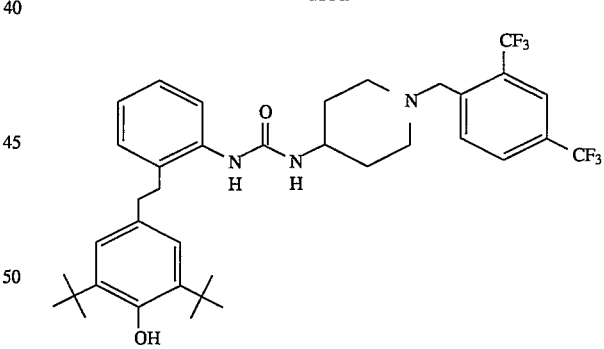

The title compound was prepared in a similar manner to that mentioned in Example 11, using 4-amino-1-[2,4-bis(trifluoromethyl)benzyl]piperidine instead of decylamine. m.p. 156°–157° C.

$^1$H-NMR($\delta$ ppm, CDCl$_3$) 7.92(d, J=8 Hz, 1H), 7.85(s, 1H), 7.73(d, J=8 Hz, 1H), 7.17–7.29(m, 4H), 6.78(s, 2H), 5.12(s, 1H), 4.98(s, 1H), 4.11(d, J=8 Hz, 1H), 3.61–3.74(m, 1H), 3.64(s, 2H), 2.75–2.88(m, 4H), 2.64–2.73(m, 2H), 2.13–2.23(m, 2H), 1.84–1.92(m, 2H), 1.38(s, 18H), 1.27–1.36(m, 2H)

IR(cm$^{-1}$) 3645, 3350, 2955, 1600, 1565, 1440, 1350, 1280, 1175, 1130, 1060, 750, 680

EXAMPLE 86

N-[2-(3,5-di-tert-butyl-4-hydroxyphenethyl)phenyl]-
N'-[1-(3-pyridylmethyl)-4-piperidyl]urea

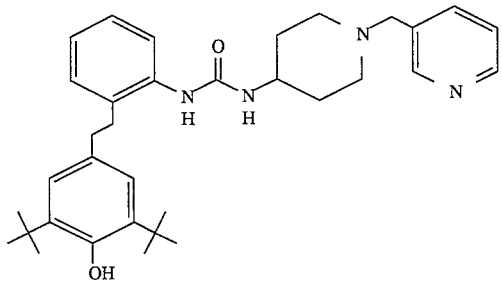

The title compound was prepared in a similar manner to that mentioned in Example 11, using 4-amino-1-(3-pyridylmethyl)piperidine instead of decylamine.

m.p. 156°–158° C.

$^1$H-NMR($\delta$ ppm, CDCl$_3$) 8.46–8.52(m, 2H), 7.60(d, J=8 Hz, 1H), 7.16–7.28(m, 5H), 6.77(s, 2H), 5.12(s, 1H), 5.02(s, 1H), 4.13(d, J=8 Hz, 1H), 3.58–3.72(m, 1H), 3.45(s, 2H), 2.67–2.87(m, 6H), 2.03–2.12(m, 2H), 1.82–1.90(m, 2H), 1.37(s, 18H), 1.22–1.37(m, 2H)

IR(cm$^{-1}$) 3632, 3362, 2950, 1645, 1561, 1433, 1232, 759, 713

EXAMPLE 87

N-[2-(3,5-di-tert-butyl-4-hydroxyphenethyl)phenyl]-
N'-[1-(4-pyridylmethyl)-4-piperidyl]urea

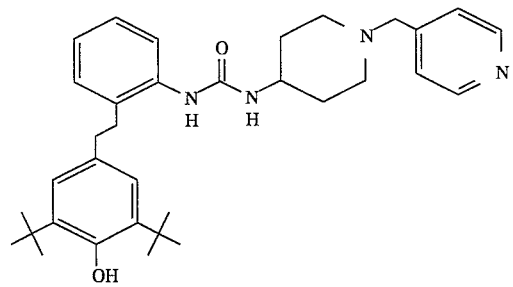

The title compound was prepared in a similar manner to that mentioned in Example 11, using 4-amino-1-(4-pyridylmethyl)piperidine instead of decylamine.

m.p. 156°–158° C.

$^1$H-NMR($\delta$ ppm, CDCl$_3$) 8.51(dd, J=4, 2 Hz, 2H), 7.16–7.28(m, 6H), 6.77(s, 2H), 5.12(s, 1H), 5.00(s, 1H), 4.12(d, J=8 Hz, 1H), 3.60–3.72(m, 1H), 3.44(s, 2H), 2.74–2.88(m, 4H), 2.66–2.74(m, 2H), 2.04–2.14(m, 2H), 1.83–1.92(m, 2H), 1.38(s, 18H), 1.25–1.38(m, 2H)

IR(cm$^{-1}$) 3630, 3292, 2948, 1620, 1560, 1435, 1237, 1109, 759

EXAMPLE 88

N-[2-(3,5-di-tert-butyl-4-hydroxyphenethyl)phenyl]-
N'-[1-(4-diethylaminobenzyl)-4-piperidyl]urea

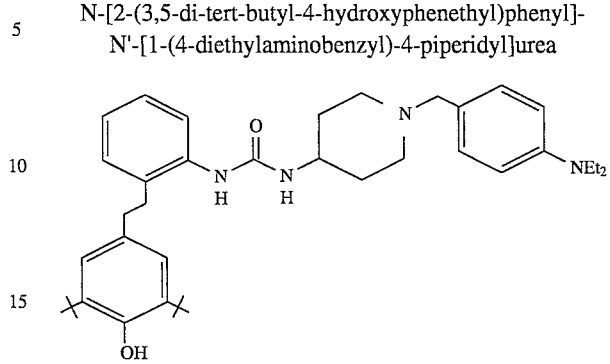

The title compound was prepared in a similar manner to that mentioned in Example 11, using 4-amino-1-(4-diethylaminobenzyl)piperidine instead of decylamine.

m.p. 138°–141° C.

$^1$H-NMR($\delta$ ppm, CDCl$_3$) 7.16–7.27(m, 4H), 7.09(d, J=8 Hz, 2H), 6.77(s, 2H), 6.60(d, J=8 Hz, 2H), 5.11(s, 1H), 4.99(s, 1H), 4.12(bd, J=7 Hz, 1H), 3.58–3.70(m, 1H), 3.28–3.40(m, 6H), 2.73–2.86(m, 6H), 1.98–2.08(m, 2H), 1.82–1.89(m, 2H), 1.37(s, 18H), 1.25–1.37(m, 2H), 1.14(t, J=7 Hz, 6H)

IR(cm$^{-1}$) 3630, 3410, 2950, 1641, 1553, 1520, 1232, 758

EXAMPLE 89

N-[2-(3,5-di-tert-butyl-4-hydroxyphenethyl)phenyl]-
N'-[1-(2-pyridylmethyl)-4-piperidyl]urea

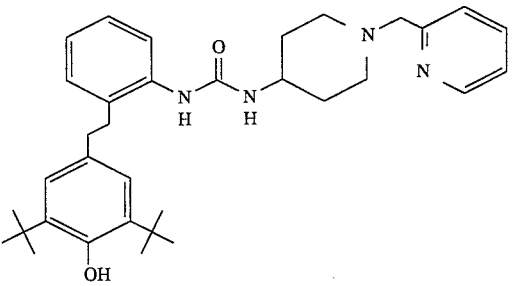

The title compound was prepared in a similar manner to that mentioned in Example 11, using 4-amino-1-(2-pyridylmethyl)piperidine instead of decylamine.

m.p. 106°–109° C.

$^1$H-NMR($\delta$ ppm, CDCl$_3$) 8.54(d, J=4 Hz, 1H), 7.58–7.65(m, 1H), 7.33(d, J=8 Hz, 1H), 7.12–7.27(m, 6H), 6.77(s, 2H), 5.11(s, 1H), 5.01(s, 1H), 4.14(d, J=7 Hz, 1H), 3.61–3.73(m, 1H), 3.59(s, 2H), 2.70–2.86(m, 6H), 2.12–2.21(m, 2H), 1.83–1.91(m, 2H), 1.37(s, 18H), 1.30–1.42(m, 2H)

IR(cm$^{-1}$) 3630, 3330, 2948, 1639, 1589, 1543, 1436, 1233, 1121, 756

EXAMPLE 90

N-[2-(3,5-di-tert-butyl-4-hydroxyphenethyl)phenyl]-N'-(cyclohexylmethyl)urea

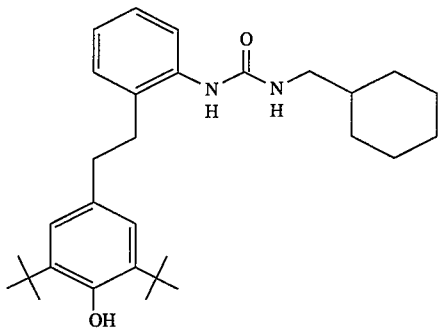

The title compound was prepared in a similar manner to that mentioned in Example 11, using aminomethylcyclohexane instead of decylamine. m.p. 208°–210° C.

$^1$H-NMR(δ ppm, CDCl$_3$) 7.18–7.24(m, 4H), 6.78(s, 2H), 5.11(s, 1H), 4.98(bs, 1H), 4.18–4.28(m, 1H), 2.97(t, J=6 Hz, 2H), 2.74–2.90(m, 4H), 1.55–1.70(m, 5H), 1.38(s, 18H), 1.08–1.30(m, 4H), 0.78–0.90(m, 2H)

IR(cm$^{-1}$) 3616, 3304, 2922, 1627, 1579, 1435, 1233

EXAMPLE 91

N-[2-(3,5-di-tert-butyl-4-hydroxyphenethyl)phenyl]-N'-(1-benzyl-4-pyperidyl)-N'-(3-pyridylmethyl)urea

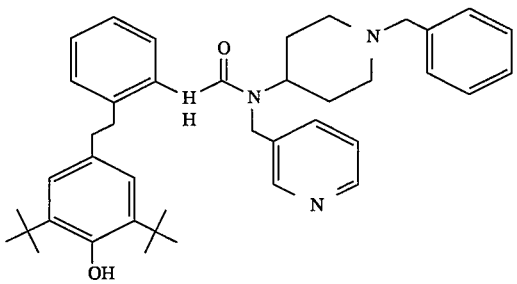

The title compound was prepared in a similar manner to that mentioned in Example 11, using 1-benzyl-4-(3-pyridylmethylamino)piperidine instead of decylamine.

m.p. 127°–130° C.

$^1$H-NMR(δ ppm, CDCl$_3$)8.55(d, J=2 Hz, 1H), 8.41(dd, J=5, 2 Hz, 1H), 7.65(d, J=8 Hz, 1H), 7.59(d, J=8 Hz, 1H), 7.13–7.30(m, 6H), 7.18(m, 1H), 7.10(dd, J=8, 5 Hz, 1H), 7.01(d, J=4 Hz, 2H), 6.75(s, 2H), 5.90(bs, 1H), 5.11(s, 1H), 4.45(s, 2H), 4.22–4.33(m, 1H), 3.47(s, 2H), 2.86–2.97(m, 2H), 2.61(t, J=7 Hz, 2H), 2.44(t, J=7 Hz, 2H), 2.00–2.14(m, 2H), 1.60–1.86(m, 4H), 1.38(s, 18H)

IR(cm$^{-1}$) 3450, 3290, 1628, 1512, 1264, 1121, 1029, 742

EXAMPLE 92

N-[2-(3,5-di-tert-butyl-4-hydroxyphenethyl)phenyl]-N'-(1-benzyl-4-piperidyl)-N'-methylurea

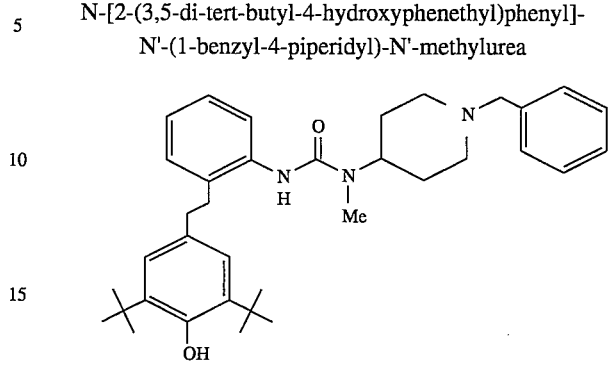

The title compound was prepared in a similar manner to that mentioned in Example 11, using 1-benzyl-4-(methylamino)piperidine instead of decylamine.

m.p. 144°–146° C.

$^1$H-NMR(δ ppm, CDCl$_3$) 7.62(d, J=8 Hz, 1H), 7.10–7.30(m, 7H), 7.10(d, J=7 Hz, 1H), 6.78(s, 2H), 5.62(bs, 1H), 5.08(s, 1H), 4.23(s, 1H), 3.48(s, 2H), 2.86–2.98(m, 2H), 2.81(s, 4H), 2.50(s, 3H), 1.98–2.10(m, 2H), 1.50–1.70(m, 4H), 1.35(s, 18H)

IR(cm$^{-1}$) 3328, 2954, 1632, 1512, 1196, 1041, 755, 701

EXAMPLE 93

N-[2-(3,5-di-tert-butyl-4-hydroxyphenethyl)phenyl]-N'-(1-benzyl-4-piperidyl)-N'-cycloheptyhrea

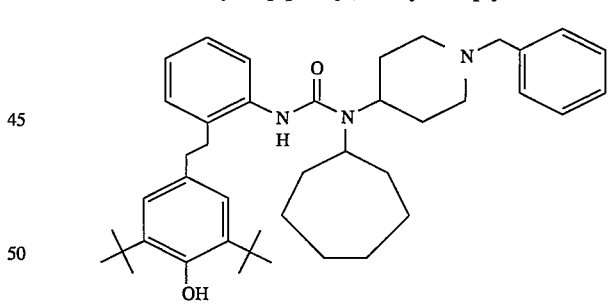

The title compound was prepared in a similar manner to that mentioned in Example 11, using 1-benzyl-4-(cycloheptylamino)piperidine instead of decylamine.

m.p. 107°–109° C.

$^1$H-NMR(δ ppm, CDCl$_3$) 7.72(d, J=8 Hz, 1H), 7.23–7.36(m, 5H), 7.19(t, J=7 Hz, 1H), 7.13(d, J=6 Hz, 1H), 7.02(t, J=7 Hz, 1H), 6.93(s, 2H), 6.12(bs, 1H), 5.05(s, 1H), 4.04–4.154(m, 1H), 3.49(s, 2H), 3.37–3.50(m, 1H), 2.90–3.00(m, 2H), 2.84(s, 4H), 1.97–2.10(m, 4H), 1.78–1.89(m, 4H), 1.20–1.65(m, 28H)

IR(cm$^{-1}$) 3476, 2922, 1662, 1528, 1454, 1236, 753

EXAMPLE 94

N-[2-(3,5-di-tert-butyl-4-hydroxyphenethyl)phenyl]-N'-(1-acetyl-4-piperidyl)urea

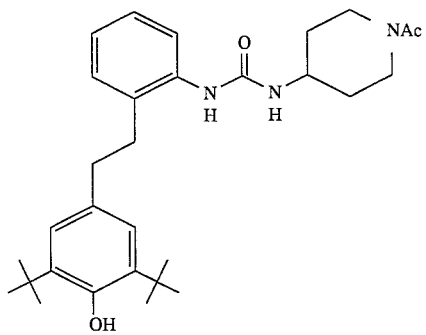

The title compound was prepared in a similar manner to that mentioned in Example 11, using 1-acetyl-4-aminopiperidine instead of decylamine. m.p. 218°–221° C.

$^1$H-NMR($\delta$ ppm, CDCl$_3$) 7.15–7.29(m, 4H), 6.76(s, 2H), 5.13(s, 1H), 4.93(bs, 1H), 4.43–4.52(m, 1H), 4.05–4.13(m, 1H), 3.76–3.90(m, 1H), 3.66–3.73(m, 1H), 3.04–3.14(m, 1H), 2.71–2.85(m, 4H), 2.58–2.70(m, 1H), 2.05(s, 3H), 1.95–2.06(m, 1H), 1.82–1.90(m, 1H), 1.37(s, 18H), 1.10–1.20(m, 2H)

IR(cm$^{-1}$) 3302, 2952, 1629, 1561, 1434, 1234

EXAMPLE 95

N-[2-(3,5-di-tert-butyl-4-hydroxyphenethyl)phenyl]-N'-(1-ethyl-4-piperidyl)urea

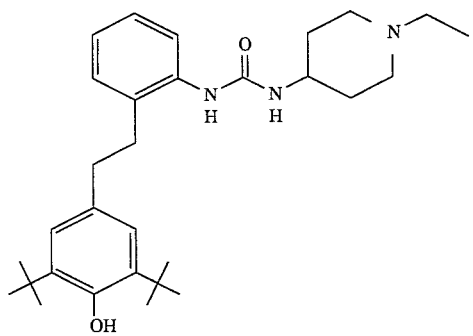

The title compound was prepared in a similar manner to that mentioned in Example 11, using 4-amino-1-ethylpiperidine instead of decylamine. m.p. 182°–184° C.

$^1$H-NMR($\delta$ ppm, CDCl$_3$) 7.10–7.30(m, 4H), 6.77(s, 2H), 5.11(s, 1H), 5.00(bs, 1H), 4.14(bd, J=8 Hz, 1H), 3.58–3.72(m, 1H), 2.70–2.90(m, 6H), 2.39(q, J=7 Hz), 1.97–2.12(m, 2H), 1.85–1.97(m, 2H), 1.37(s, 18H), 1.30–1.40(m, 2H), 1.07(t, J=7 Hz, 3H)

IR(cm$^{-1}$) 3362, 2950, 1640, 1563, 1435, 1235

EXAMPLE 96

N-[2-(3,5-di-tert-butyl-4-hydroxyphenethyl)phenyl]-N'-(1-methyl-4-piperidyl)urea

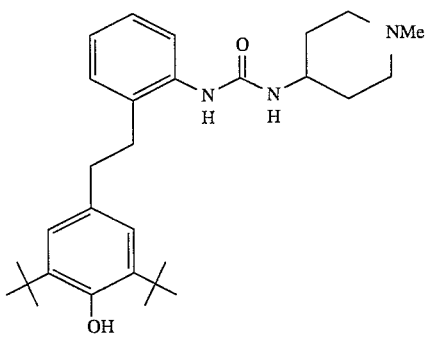

The title compound was prepared in a similar manner to that mentioned in Example 11, using 4-amino-1-methylpiperidine instead of decylamine. m.p. 193°–195° C.

$^1$H-NMR($\delta$ ppm, CDCl$_3$) 7.15–7.25(m, 4H), 6.77(s, 2H), 5.12(s, 1H), 4.97(bs, 1H), 4.10(bd, J=8 Hz, 1H), 3.58–3.70(m, 1H), 2.70–2.85(m, 6H), 2.25(s, 3H), 2.02–2.12(m, 2H), 1.84–1.93(m, 2H), 1.38(s, 18H), 1.30–1.43(m, 2H)

IR(cm$^{-1}$) 3360, 2944, 1639, 1562

EXAMPLE 97

N-[2-(3,5-di-tert-butyl-4-hydroxyphenethyl)phenyl]-N'-[1-(2,2-dimethylpropyl)-4-piperidyl]urea

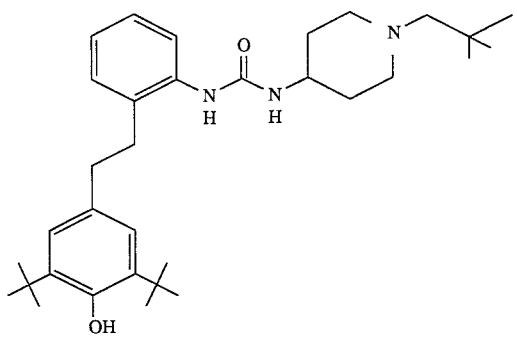

The title compound was prepared in a similar manner to that mentioned in Example 11, using 4-amino-1-(2,2-dimethylpropyl)piperidine instead of decylamine.

$^1$H-NMR($\delta$ ppm, CDCl$_3$) 7.18–7.26(m, 4H), 6.78(s, 2H), 5.11(s, 1H), 5.06(bs, 1H), 4.12(bd, J=8 Hz, 1H), 3.53–3.65(m, 1H), 2.75–2.90(m, 4H), 2.60–2.68(m, 2H), 2.22–2.32(m, 2H), 1.98(s, 2H), 1.73–1.83(m, 2H), 1.38(s, 18H), 1.20–1.40(m, 2H), 0.81(s, 9H)

IR(cm$^{-1}$) 3322, 2952, 1638, 1536, 1435, 1234

EXAMPLE 98

N-[2-(3,5-di-tert-butyl-4-hydroxyphenethyl)phenyl]-N'-(1-benzyl-3-pyrrolidinyl)urea

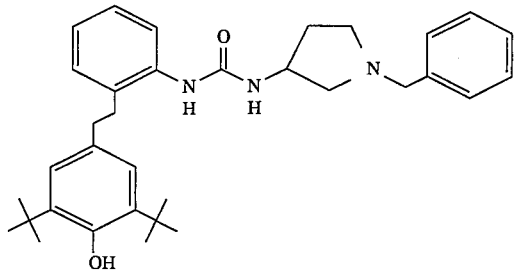

The title compound was prepared in a similar manner to that mentioned in Example 11, using 3-amino-1-benzylpyrrolidine instead of decylamine.

$^1$H-NMR(δ ppm, CDCl$_3$) 7.10–7.30(m, 9H), 6.78(s, 2H), 5.37(bs, 1H), 5.10(s, 1H), 4.71(bd, J=8 Hz, 1H), 4.23–4.34(m, 1H), 3.55(d, J=13 Hz, 1H), 3.50(d, J=13 Hz, 1H), 2.70–2.81(m, 6H), 2.49(d, J=4 Hz, 2H), 2.14–2.36(m, 2H), 1.37(s, 18H)

IR(cm$^{-1}$) 3634, 3304, 2954, 1638, 1559, 1436, 1234, 749, 699

EXAMPLE 99

N-[2-(3,5-di-tert-butyl-4-hydroxyphenethyl)phenyl]-N'-(1-benzyl-3-piperidyl)-N'-methylurea

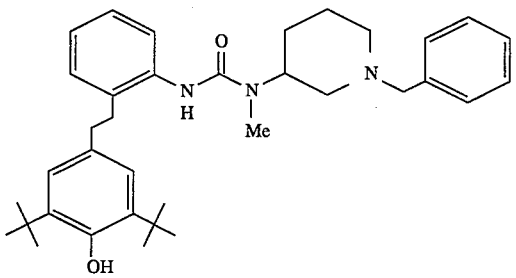

The title compound was prepared in a similar manner to that mentioned in Example 11, using 3-amino-1-benzylpiperazine instead of decylamine.

$^1$H-NMR(δ ppm, CDCl$_3$) 7.59(d, J=8 Hz, 1H), 7.15–7.40(m, 7H), 7.08(t, J=7 Hz, 1H), 6.79(s, 2H), 5.72(bs, 1H), 5.06(s, 1H), 4.22–4.34(m, 1H), 3.48(s, 2H), 2.70–2.80(m, 6H), 2.58(s, 3H), 1.60–1.90(m, 4H), 1.30–1.46(m, 2H), 1.35(s, 18H)

IR(cm$^{-1}$) 3630, 3422, 2940, 1639, 1520, 1485, 1452, 1312, 1249, 1122, 752, 699

EXAMPLE 100

N-[2-(3,5-di-tert-butyl-4-hydroxyphenethyl)phenyl]-N'-[1-[bis(4-fluorophenyl)methyl]-4-piperidyl]urea

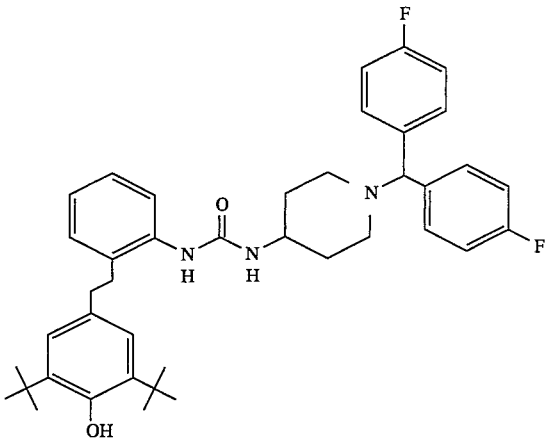

The title compound was prepared in a similar manner to that mentioned in Example 11, using 4-amino-1-[bis(4-fluorophenyl)methyl]piperidine instead of decylamine.

$^1$H-NMR(δ ppm, CDCl$_3$) 7.65–7.80(m, 4H), 7.15–7.30(m, 4H), 7.12(t, J=7 Hz, 2H), 6.84(d, J=9 Hz, 2H), 6.77(s, 2H), 5.11(s, 1H), 5.01(bs, 1H), 4.13(t, J=7 Hz, 2H), 3.75–3.95(m, 3H), 2.91–3.03(m, 2H), 2.75–2.90(m, 4H), 1.92–2.03(m, 2H), 1.25–1.40(m, 2H), 1.37(s, 18H)

IR(cm$^{-1}$) 3314, 2948, 1638, 1602, 1544, 1303, 1226, 1153, 768

EXAMPLE 101

N-[2-(3,5-di-tert-butyl-4-hydroxystyryl)phenyl]-N'-(2-pyridylmethyl)urea

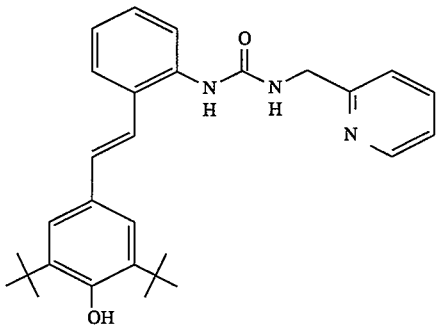

(1) To a solution of 4-(2-aminostyryl)-2,6-di-tert-butylphenol (4.85 g, 15.0 mmol) and diisopropylamine (1.72 g, 17.0 mmol) in methylene chloride (30 ml) was added dropwise under ice-cooling phenyl chloroformate (2.51 g, 16.0 mmol). The mixture was stirred for 7 hrs, while returning slowly to room temperature. To the mixture was added diisopropylamine (0.51 g, 5.0 mmol) and added dropwise under ice-cooling diisopropylamine (0.51 g, 5.0 mmol). This mixture was stirred for 3 hrs, while returning slowly to room temperature. The reaction solution was washed with water and a saturated NaCl solution, dried over MgSO$_4$ and concentrated. Purification of the residue by a silica gel column chromatography gave N-[2-(3,5-di-tertbutyl-4-hydroxystyryl)phenyl]phenyl carbamate (6.65 g, 99%) as a viscous oil.

$^1$H-NMR($\delta$ ppm, CDCl$_3$) 7.91(b, 1H), 6.90–7.53(m, 13H), 5.35(s, 1H), 1.49(s, 18H)

(2) A solution of N-[2-(3,5-di-tert-butyl-4-hydroxystyryl)phenyl]phenyl carbamate (1.00 g, 2.25 mmol) and 2-(aminomethyl)pyridine (0.27 g, 2.50 mmol) in xylene (5 ml) was stirred at 80°–100° C. for 3 hrs. After distilling off the solvent, purification of the residue by a silica gel column chromatography afforded N-[2-(3,5-di-tert-butyl-4-hydroxystyryl)phenyl]-N'-(2-pyridylmethyl)urea (0.54 g, 71%) as crystals. m.p. 207°–210° C.

$^1$H-NMR($\delta$ ppm, CDCl$_3$) 8.37(d, J=4 Hz, 1H), 7.59(dd, J=8, 2 Hz, 1H), 7.51(d, J=7 Hz, 1H), 7.43–7.50(m, 1H), 7.31(s, 2H), 7.16–7.28(m, 3H), 7.17(d, J=16 Hz, 1H), 7.02–7.07(m, 1H), 6.99(d, J=16 Hz, 1H), 6.68–6.91(m, 1H), 5.79–5.87(m, 1H), 5.32(s, 1H), 4.51(d, J=8 Hz, 2H), 1.45(s, 18H)

IR(cm$^{-1}$) 3350, 3270, 2960, 1640, 1560, 1475, 1440, 1235, 1010, 755, 740

EXAMPLE 102

N-[2-(3,5-di-tert-butyl-4-hydroxystyryl)phenyl]-N'-cycloheptylurea

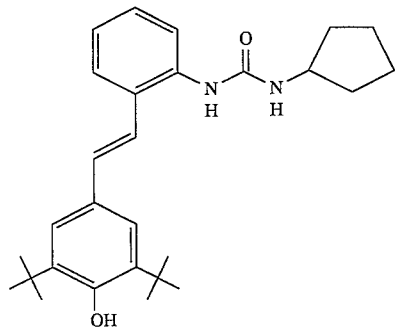

The title compound was prepared in a similar manner to that mentioned in Example 101, using cycloheptylamine instead of 2-(aminomethyl)pyridine.

m.p. 203°–206° C.

$^1$H-NMR($\delta$ ppm, CDCl$_3$) 7.61(d, J=8 Hz, 1H), 7.38(d, J=8 Hz, 1H), 7.33(s, 2H), 7.18–7.28(m, 2H), 7.06(d, J=16 Hz, 1H), 7.00(d, J=16 Hz, 1H), 6.05(s, 1H), 5.33(s, 1H), 4.48–4.55(m, 1H), 4.04–4.16(m, 1H), 1.88–2.00(m, 2H), 1.48–1.62(m, 4H), 1.47(s, 18H), 1.22–1.37(m, 2H)

IR(cm$^{-1}$) 3630, 3310, 2950, 1630, 1560, 1440, 1235, 960, 745

EXAMPLE 103

N-[2-(3,5-di-tert-butyl-4-hydroxystyryl)phenyl]-N'-adamantylurea

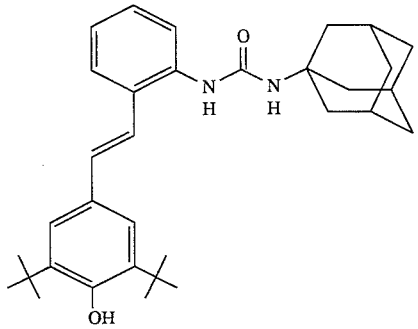

The title compound was prepared in a similar manner to that mentioned in Example 101, using 1-adamantanamine instead of 2-(aminomethyl)pyridine.

m.p. 205°–211° C.

$^1$H-NMR($\delta$ ppm, CDCl$_3$) 7.66(dd, J=7, 2 Hz, 1H), 7.34(s, 2H), 7.29–7.36(m, 1H), 7.15–7.29(m, 2H), 7.06(d, J=16 Hz, 1H), 7.00(d, J=16 Hz, 1H), 5.90(s, 1H), 5.33(s, 1H), 4.34(s, 1H), 1.82–2.06(m, 9H), 1.52–1.67(m, 6H), 1.47(s, 18H)

IR(cm$^{-1}$) 3630, 3330, 2900, 1640, 1560, 1525, 1235, 740,

EXAMPLE 104

N-[2-(3,5-di-tert-butyl-4-hydroxystyryl)phenyl]-N',N'-dibenzylurea

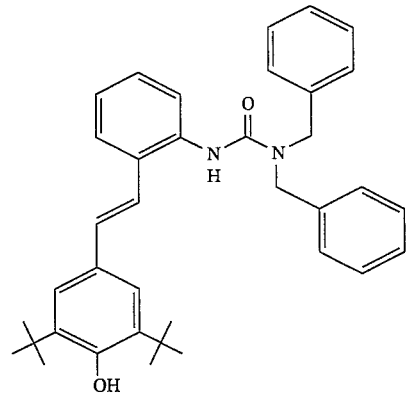

The title compound was prepared in a similar manner to that mentioned in Example 101, using N,N-dibenzylamine instead of 2-(aminomethyl)pyridine.

m.p. 175°–178° C.

$^1$H-NMR($\delta$ ppm, CDCl$_3$) 7.79(dd, J=8, 1Hz, 1H), 7.36(dd, J=8, 1 Hz, 1H), 7.02–7.30(m, 13H), 7.02–7.08(m, 1H), 6.78(d, J=16 Hz, 1H), 6.65(d, J=16 Hz, 1H), 5.31(s, 1H), 4.60(s, 4H), 1.47(s, 18H)

IR(cm$^{-1}$) 3420, 3390, 2940, 1660, 1580, 1520, 1450, 1435, 1230, 960, 755

EXAMPLE 105

N-[2-(3,5-di-tert-butyl-4-hydroxystyryl)phenyl]-N'-methyl-N'-heptylurea

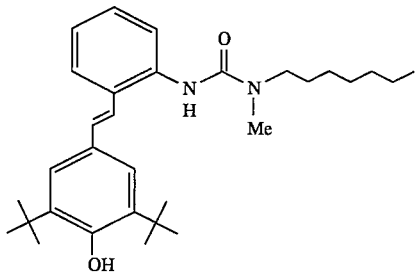

The title compound was prepared in a similar manner to that mentioned in Example 101, using N-methylheptylamine instead of 2-(aminomethyl)pyridine.

¹H-NMR(δ ppm, CDCl₃) 7.81(d, J=8 Hz, 1H), 7.44(d, J=8 Hz, 1H), 7.32(s, 2H), 7.22–7.27(m, 1H), 7.05–7.10(m, 1H), 7.00(d, J=16 Hz, 1H), 6.93(d, J=16 Hz, 1H), 6.36(s, 1H), 5.32(s, 1H), 3.34(d, J=8 Hz, 2H), 3.02(s, 3H), 1.54–1.65(m, 2H), 1.47(s, 18H), 1.16–1.32(m, 8H), 0.84(t, J=7 Hz, 3H)

IR(cm⁻¹) 3640, 3450, 3300, 2960, 2930, 1640, 1580, 1520, 1485, 1440, 1240, 1155, 960, 750

EXAMPLE 106

N-[2-(3,5-di-tert-butyl-4-hydroxystyryl)phenyl]-N'-benzyl-N'-(2-pyridylmethyl)urea

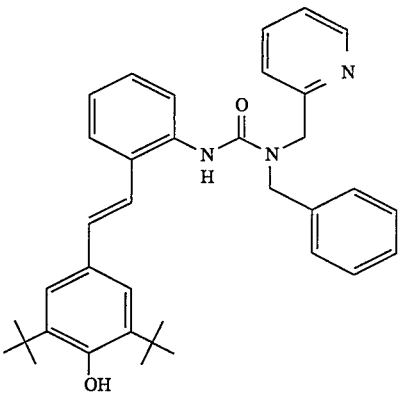

The title compound was prepared in a similar manner to that mentioned in Example 101, using 2-(benzylaminomethyl)pyridine instead of 2-(aminomethyl)pyridine.

¹H-NMR(δ ppm, CDCl₃) 9.74(b, 1H), 8.14(d, J=4 Hz, 1H), 7.87(d, J=8 Hz, 1H), 7.47–7.57(m, 1H), 7.18–7.34(m, 9H), 6.88–7.11(m, 4H), 5.26(s, 1H), 4.65(s, 2H), 4.49(s, 2H), 1.40(s, 18H)

IR(cm⁻¹) 3390, 2950, 1660, 1580, 1525, 1455, 1230, 960, 755, 735, 700

EXAMPLE 107

N-[2-(3,5-di-tert-butyl-4-hydroxystyryl)phenyl]-N'-(3,9-dimethyl-3,9-diazabicyclo[3.3.1]-7-nonyl)urea

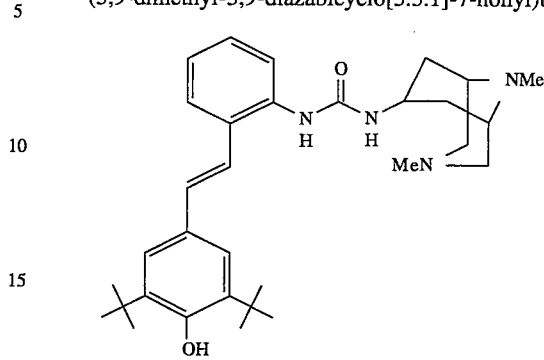

The title compound was prepared in a similar manner to that mentioned in Example 101, using 7-amino-3,9-dimethyl-3,9-diazabicyclo[3.3.1]nonane instead of 2-(aminomethyl)pyridine.

m.p. 188°–191° C.

¹H-NMR(δ ppm, CDCl₃) 8.78(d, J=10 Hz, 1H), 7.64(dd, J=7, 2 Hz, 1H), 7.30–7.35(m, 3H), 7.13–7.27(m, 2H), 7.13(d, J=2 Hz, 1H), 7.02(d, J=2 Hz, 1H), 5.93(s, 1H), 5.35(s, 1H), 4.22–4.33(m, 1H), 2.66–2.72(m, 2H), 2.41(s, 3H), 2.22–2.40(m, 6H), 1.48(s, 3H), 1.47(s, 18H), 1.28–1.38(m, 2H)

IR(cm⁻¹) 3410, 2940, 1630, 1600, 1510, 1440, 1390, 1265, 1185, 965, 760

EXAMPLE 108

N-[2-(3,5-di-tert-butyl-4-hydroxyphenethyl)-4,6-difluorophenyl]-N'-(1-benzyl-4-piperidyl)urea

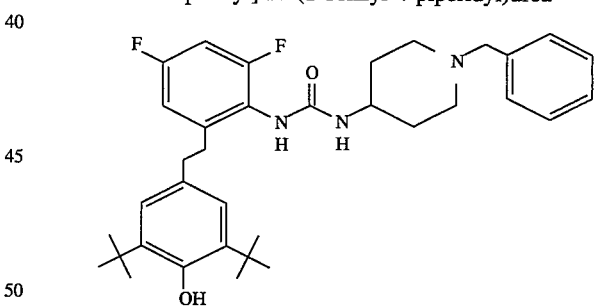

(1) To a solution of 4-(2-amino-3,5-difluorophenethyl)-2,6-di-tert-butylphenol (1.37 g, 3.8 mmol) and diisopropylamine (0.50 g, 4.9 mmol) in methylene chloride (20 ml) was added dropwise under ice-cooling phenyl chloroformate (0.66 g, 4.2 mmol) and the mixture was stirred for 3 hrs, while returning slowly to room temperature. Diisopropylamine (0.19 g, 1.9 mmol) was further added and phenyl chloroformate (0.30 g, 1.9 mmol) was added dropwise under ice-cooling. The mixture was stirred for 3 hrs while returning slowly to room temperature. The reaction solution was washed with water and a saturated NaCl solution, dried over MgSO₄ and concentrated. Purification of the residue by silica gel column chromatography gave N-[2-(3,5-di-tert-butyl-4-hydroxyphenethyl)-4,6-difluorophenyl]phenyl carbamate (1.82 g, 99%) as oil.

¹H-NMR(δ ppm, CDCl₃)7.04–7.42(m, 5H), 6.67–6.85(m, 4H), 5.16(s, 1H), 4.94(s, 1H), 2.76–3.02(m, 4H), 1.37(s, 18H)

(2) A solution of N-[2-(3,5-di-tert-butyl-4-hydroxyphenethyl)-4,6-difluorophenyl]phenyl carbamate (1.82 g, 3.8 mmol) and 4-amino-1-benzylpyridine (0.72 g, 3.8 mmol) in toluene (10 ml) was stirred at 100°–120° C. for 2 hrs. After distilling off the solvent, purification of the residue by a silica gel column chromatography afforded N-[2-(3,5-di-tert-butyl-4-hydroxyphenethyl)-4,6-difluorophenyl]-N'-(1-benzyl-4-piperidyl)urea (1.39 g, 64%) as a noncrystalline solid.

¹H-NMR(δ ppm, CDCl₃) 7.20–7.30(m, 5H), 6.65–6.80(m, 4H), 5.12(s, 1H), 4.79(bs, 1H), 4.14(bd, J=8 Hz, 1H), 3.54–3.66(m, 1H), 3.44(s, 2H), 2.84(d, J=7 Hz, 2H), 2.70–2.79(m, 4H), 1.98–2.10(m, 2H), 1.80–1.92(m, 2H), 1.30–1.40(m, 20H)

IR(cm⁻¹) 3638, 3316, 2952, 1639, 1562, 1494, 1436, 1235, 1122

EXAMPLE 109

N-[2-(3,5-di-tert-butyl-4-hydroxyphenethyl)-4-fluorophenyl]-N'-(1-benzyl-4-piperidyl)urea

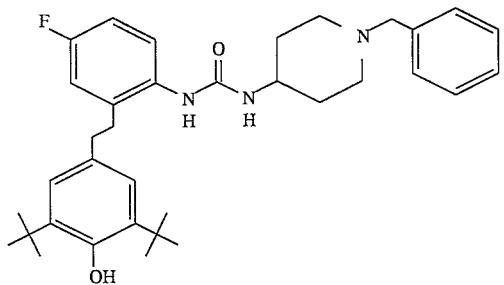

The title compound was prepared in a similar manner to that mentioned in Example 108, using 4-(2-amino-5-fluorophenethyl)-2,6-di-tert-butylphenol instead of 4-(2-amino-3,5-difluorophenethyl)-2,6-di-tert-butylphenol.

m.p. 108°–109° C.

¹H-NMR(δ ppm, CDCl₃)7.21–7.31(m, 5H), 7.16(dd, J=9, 5 Hz, 1H), 6.87–6.96(m, 2H), 6.77(s, 2H), 5.12(s, 1H), 4.86(s, 1H), 3.99(d, J=8 Hz, 1H), 3.55–3.70(m, 1H), 3.44(s, 1H), 2.70–2.85(m, 6H), 2.05(t, J=11 Hz, 2H), 1.85(d, J=10 Hz, 2H), 1.38(s, 18H), 1.25–1.35(m, 2H)

IR(cm⁻¹) 3636, 3280, 1634, 1561, 1495, 1435, 1234, 1213, 1120, 739, 699

EXAMPLE 110

N-[2-(3,5-di-tert-butyl-4-hydroxyphenethyl)-5-fluorophenyl]-N'-(1-benzyl-4-piperidyl)urea

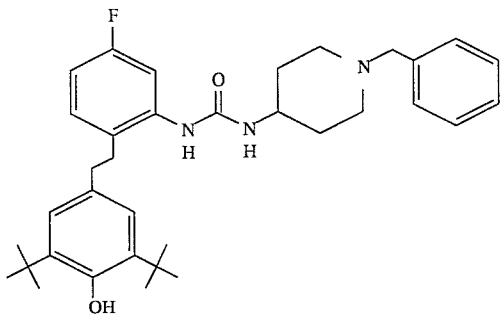

The title compound was prepared in a similar manner to that mentioned in Example 108, using 4-(2-amino-4-fluorophenethyl)-2,6-di-tert-butylphenol instead of 4-(2-amino-3,5-difluorophenethyl)-2,6-di-tert-butylphenol.

m.p. 118°–119° C.

¹H-NMR(δ ppm, CDCl₃) 7.20–7.32(m, 5H), 7.13–7.20(m, 2H), 6.84(dt, J=3, 8 Hz, 1H), 6.78(s, 2H), 5.13(s, 1H), 5.01(s, 1H), 4.02(d, J=8 Hz, 1H), 3.46–3.63(m, 1H), 3.46(s, 2H), 2.77(bs, 6H), 2.06(t, J=11 Hz, 2H), 1.86(d, J=11 Hz, 2H), 1.38(s, 18H), 1.30–1.40(m, 2H)

IR(cm⁻¹) 3630, 3350, 1640, 1602, 1563, 1434, 1233, 738, 700

EXAMPLE 111

N-[2-(3,5-di-tert-butyl-4-hydroxyphenethyl)-4-methoxyphenyl]-N'-(1-benzyl-4-piperidyl)urea

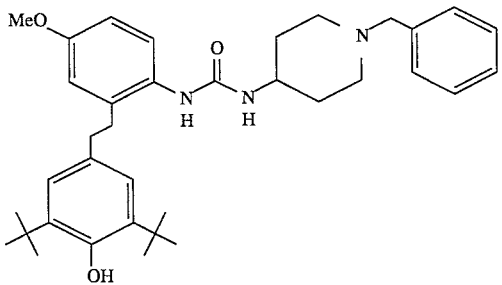

The title compound was prepared in a similar manner to that mentioned in Example 108, using 4-(2-amino-5-methoxyphenethyl)-2,6-di-tert-butylphenol instead of 4-(2-amino-3,5-difluorophenethyl)-2,6-di-tert-butylphenol.

m.p. 174°–175° C.

¹H-NMR(δ ppm, CDCl₃) 7.20–7.30(m, 5H), 7.00–7.07(m, 1H), 6.78(s, 2H), 6.70–6.75(m, 2H), 5.09(s, 1H), 4.91(s, 1H), 4.05(d, J=8 Hz, 1H), 3.79(s, 3H), 3.60–3.65(m, 1H), 3.43(s, 2H), 2.70–2.80(m, 6H), 2.05(t, J=11 Hz, 2H), 1.85(d, J=11 Hz, 2H), 1.38(s, 18H), 1.20–1.40(m, 2H)

IR(cm⁻¹) 3630, 3312, 1634, 1561, 1501, 1436, 1282, 1231, 1055, 880, 750, 710

EXAMPLE 112

N-[4-(3,5-di-tert-butyl-4-hydroxyphenethyl)phenyl]-N'-phenylurea

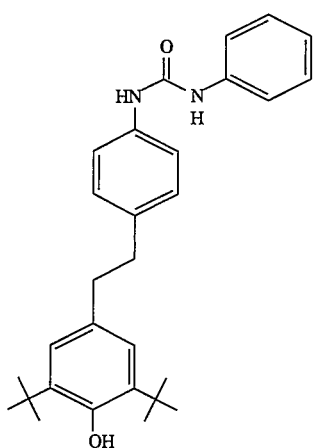

The title compound was prepared in a similar manner to that mentioned in Example 1, using 4-(4-aminophenethyl)-2,6-di-tert-butylphenol instead of 4-(2-aminophenethyl)-2,6-di-tert-butylphenol and using benzoic acid instead of 4-hexyloxybenzoic acid. m.p. 206°–207° C.

$^1$H-NMR($\delta$ ppm, CDCl$_3$) 7.22–7.38(m, 6H), 7.18(d, J=9 Hz, 2H), 7.08–7.14(m, 1H), 6.55(bs, 1H), 6.47(bs, 1H), 2.77–2.92(m, 4H), 1.43(s, 18H)

IR(cm$^{-1}$) 3640, 3330, 2960, 1655, 1605, 1565, 1440, 1320, 1240, 760, 695

EXAMPLE 113

N-[4-(3,5-di-tert-butyl-4-hydroxyphenethyl)phenyl]-N'-heptylurea

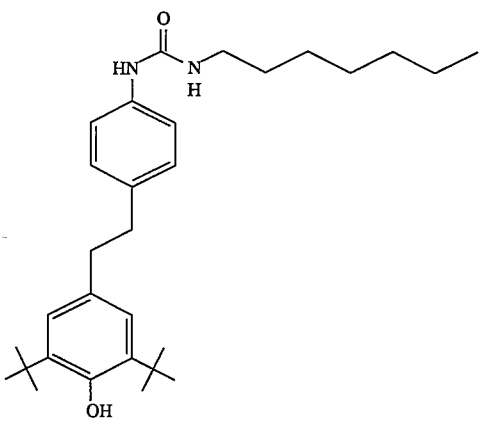

The title compound was prepared in a similar manner to that mentioned in Example 1, using 4-(4-aminophenethyl)-2,6-di-tert-butylphenol instead of 4-(2-aminophenethyl)-2,6-di-tert-butylphenol and n-octanoic acid instead of 4-hexyloxybenzoic acid. m.p. 151°–152° C.

$^1$H-NMR($\delta$ ppm, CDCl$_3$)7.13–7.21(m, 4H), 6.95(s, 2H), 6.22(bs, 1H), 5.06(s, 1H), 4.73(bt, J=5 Hz, 1H), 3.23(dt, J=5, 7 Hz, 2H), 2.75–2.90(m, 42H), 1.45–1.54(m, 2H), 1.42(s, 18H), 1.21–1.36(m, 8H), 0.88(t, J=7 Hz, 3H)

IR(cm$^{-1}$) 3630, 3120, 2960, 2930, 2860, 1645, 1605, 1575, 1520, 1440, 1235

EXAMPLE 114

1-Benzyl-4-[N-[2-(3,5-di-tert-butyl-4-hydroxyphenethyl)phenyl]carbamoyl]piperazine

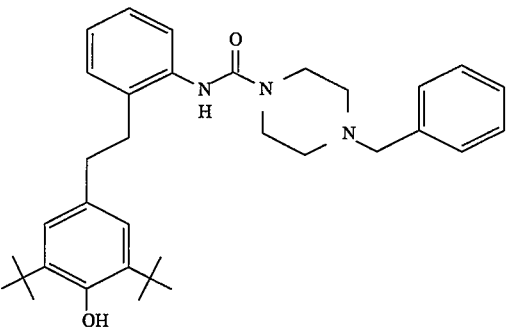

The title compound was prepared in a similar manner to that mentioned in Example 11, using 1-benzylpiperazine instead of decylamine. m.p. 70°–72° C.

$^1$H-NMR($\delta$ ppm, CDCl$_3$) 7.49–7.51(m, 1H), 7.09–7.33(m, 8H), 6.78(s, 2H), 5.61(s, 1H), 5.06(s, 1H), 3.50(s, 2H), 3.22(t, J=5 Hz, 4H), 2.80(s, 4H), 2.39(t, J=5 Hz, 4H), 1.33(s, 18H)

IR(cm$^{-1}$) 3636, 3310, 2952, 1635, 1516, 1435, 1234, 1001, 754

EXAMPLE 115

4-Benzyl-1-[N-[2-(3,5-di-tert-butyl-4-hydroxyphenethyl)phenyl]carbamoyl]piperidine

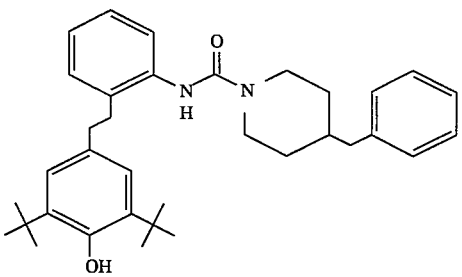

The title compound was prepared in a similar manner to that mentioned in Example 11, using 4-benzylpiperidine instead of decylamine.

$^1$H-NMR($\delta$ ppm, CDCl$_3$) 7.52(d, J=8 Hz, 1H), 7.06–7.32(m, 8H), 6.79(s, 2H), 5.67(s, 1H), 5.06(s, 1H), 3.68–3.76(m, 2H), 2.81(s, 4H), 2.62–2.72(m, 2H), 2.53(t, J=7 Hz, 4H), 1.50–1.73(m, 3H), 1.35(s, 18H), 1.10–1.23(m, 2H)

IR(cm$^{-1}$) 3645, 3440, 3330, 2960, 2925, 1645, 1525, 1455, 1440, 1250, 755, 705

EXAMPLE 116

1-[N-[2-(3,5-di-tert-butyl-4-hydroxyphenethyl)phenyl]carbamoyl]-1,2,3,4-tetrahydroquinoline

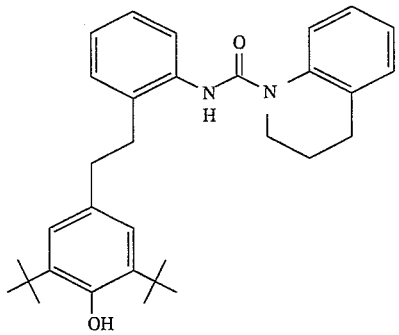

The title compound was prepared in a similar manner to that mentioned in Example 11, using 1,2,3,4-tetrahydroquinoline instead of decylamine.

$^1$H-NMR($\delta$ ppm, CDCl$_3$) 7.82(d, J=7 Hz, 1H), 7.36(d, J=7 Hz, 1H), 7.13–7.21(m, 2H), 7.16(d, J=7 Hz, 1H), 6.99–7.09(m, 3H), 6.89(bs, 1H), 6.82(s, 2H), 5.06(s, 1H), 3.80(t, J=6 Hz, 2H), 2.78(t, J=6 Hz, 2H), 2.69(s, 4H), 1.98(m, 2H), 1.39(s, 18H)

IR(cm$^{-1}$) 3630, 3434, 2946, 1671, 1524, 1492, 1435, 1304, 236, 753

EXAMPLE 117

2-[N-[2-(3,5-di-tert-butyl-4-hydroxyphenethyl)phenyl]carbamoyl]-1,2,3,4-tetrahydroisoquinoline

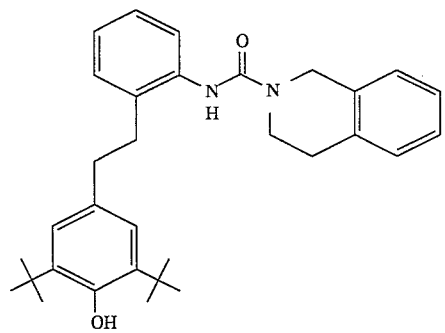

The title compound was prepared in a similar manner to that mentioned in Example 11, using 1,2,3,4-tetrahydroisoquinoline instead of decylamine. m.p. 148°–150° C.

$^1$H-NMR($\delta$ ppm, CDCl$_3$) 7.55(d, J=8 Hz, 1H), 7.10–7.26(m, 7H), 6.83(s, 1H), 5.73(bs, 1H), 5.10(s, 1H), 4.52(s, 2H), 3.44(t, J=6 Hz, 2H), 2.86(t, J=6 Hz, 2H), 2.84(s, 4H), 1.36(s, 18H)

IR(cm$^{-1}$) 3628, 3312, 1630, 1515, 1459, 1437, 1373, 1231, 747

EXAMPLE 118

1-[N-[2-(3,5-di-tert-butyl-4-hydroxyphenethyl)phenyl]carbamoyl]-4-(3,4-methylenedioxybenzyl)piperazine

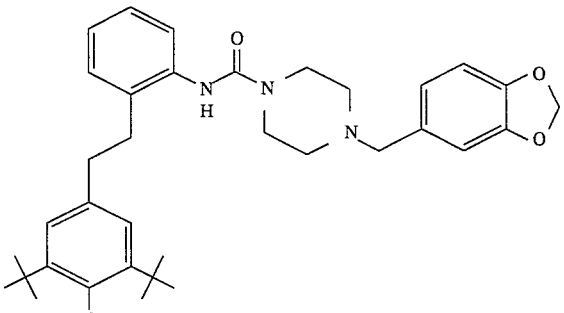

The title compound was prepared in a similar manner to that mentioned in Example 11, using 1-(3,4-methylenedioxybenzyl)piperazine instead of decylamine.

m.p. 149°–151° C.

$^1$H-NMR($\delta$ ppm, CDCl$_3$) 7.50(d, J=7 Hz, 1H), 7.18–7.23(m, 2H), 7.11(dd, J=7, 7 Hz, 1H), 6.83(s, 1H), 6.70–6.76(m, 2H), 5.95(s, 2H), 5.61(bs, 1H), 5.06(s, 1H), 3.40(s, 2H), 3.22(t, J=5 Hz, 4H), 2.80(s, 4H), 2.36(t, J=5 Hz, 4H), 1.34(s, 18H)

IR(cm$^{-1}$) 3626, 3302, 2956, 1632, 1504, 1491, 1438, 1247, 1040, 999, 759

EXAMPLE 119

1-[N-[2-(3,5-di-tert-butyl-4-hydroxyphenethyl)phenyl]carbamoyl]indoline

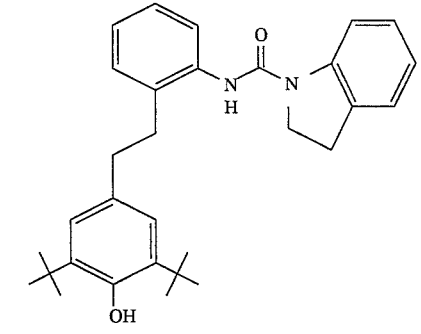

The title compound was prepared in a similar manner to that mentioned in Example 11, using indoline instead of decylamine.

$^1$H-NMR($\delta$ ppm, CDCl$_3$) 7.91(d, J=8 Hz, 1H), 7.61(d, J=8 Hz, 1H), 7.10–7.30(m, 2H), 6.91(dd, J=8, 8 Hz, 2H), 6.81(d, J=8 Hz, 2H), 6.78(s, 2H), 5.65(bs, 1H), 5.10(s, 1H), 3,57(t, J=8 Hz, 2H), 3.14(t, J=8 Hz, 2H), 2.86(s, 4H), 1.35(s, 18H)

IR(cm$^{-1}$) 3622, 3272, 2952, 1654, 1594, 1507, 1485, 1448, 1347, 1234, 753

EXAMPLE 120

1-[N-[2-(3,5-di-tert-butyl-4-hydroxyphenethyl)phenyl]carbamoyl]-4-methylpiperazine

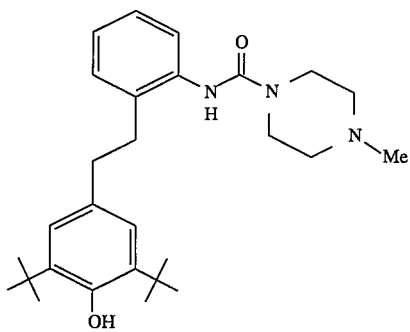

The title compound was prepared in a similar manner to that mentioned in Example 11, using 1-methylpiperazine instead of decylamine. m.p. 134°–137° C.

$^1$H-NMR($\delta$ ppm, CDCl$_3$) 7.47(d, J=8 Hz, 1H), 7.17–7.26(m, 2H), 7.12(ddd, J=7, 7, 2 Hz, 1H), 6.79(s, 2H), 5.56(s, 1H), 5.10(s, 1H), 3.25(t, J=5 Hz, 4H), 2.82(s, 4H), 2.35(t, J=5 Hz, 4H), 2.29(s, 3H), 1.37(s, 18H)

IR(cm$^{-1}$) 3632, 3440, 2940, 1636, 1511, 1437, 1002, 750

EXAMPLE 121

1-[N-[2-(3,5-di-tert-butyl-4-hydroxyphenethyl)phenyl]carbamoyl]perhydroazepine

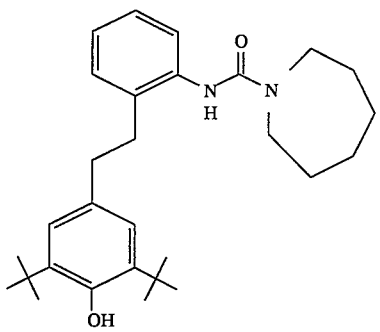

The title compound was prepared in a similar manner to that mentioned in Example 11, using hexamethyleneimine instead of decylamine. m.p. 136°–138° C.

$^1$H-NMR($\delta$ ppm, CDCl$_3$) 7.67(dd, J=7, 2 Hz, 1H), 7.17–7.24(m, 2H), 7.08(ddd, J=7, 7, 2 Hz, 1H), 6.82(s, 2H), 5.78(s, 1H), 5.08(s, 1H), 3.26–3.34(m, 4H), 2.82(bs, 1H), 1.66–1.74(m, 4H), 1.52–1.59(m, 4H), 1.37(s, 18H)

IR(cm$^{-1}$) 3460, 1660, 1587, 1525, 1453, 1436, 755

EXAMPLE 122

4-[N-[2-(3,5-di-tert-butyl-4-hydroxyphenethyl)phenyl]carbamoyl]morpholine

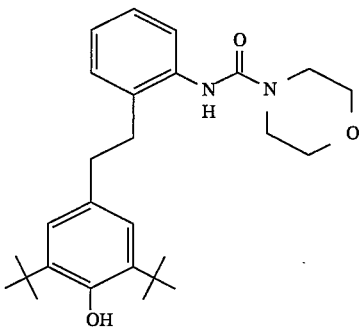

The title compound was prepared in a similar manner to that mentioned in Example 11, using morpholine instead of decylamine. m.p. 186°–189° C.

$^1$H-NMR($\delta$ ppm, CDCl$_3$) 7.47(dd, J=8, 2 Hz, 1H), 7.19–7.27(m, 2H), 7.14(ddd, J=7, 7, 2 Hz, 1H), 6.78(s, 2H), 5.52(s, 1H), 5.09(s, 1H), 3.64(t, J=5 Hz, 4H), 3.19(t, J=5 Hz, 4H), 2.82(s, 4H), 1.36(s, 18H)

IR(cm$^{-1}$) 3644, 3420, 3290, 2956, 1631, 1525, 1435, 1262, 1118, 756

EXAMPLE 123

3-[N-[2-(3,5-di-tert-butyl-4-hydroxyphenethyl)phenyl]carbamoyl]-3-azabicyclo[3.2.2]nonane

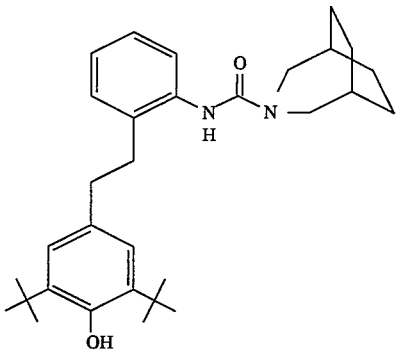

The title compound was prepared in a similar manner to that mentioned in Example 11, using 3-azabicyclo[3.2.2]nonane instead of decylamine.

m.p. 184°–186° C.

$^1$H-NMR($\delta$ ppm, CDCl$_3$) 7.52(d, J=8 Hz, 1H), 7.26–7.34(m, 2H), 7.09(dd, J=7, 7 Hz, 1H), 6.81(s, 2H), 5.71(s, 1H), 5.08(s, 1H), 3.40(d, J=4 Hz, 4H), 2.82(s, 4H), 1.96–2.04(m, 2H), 1.57–1.72(m, 8H), 1.37(s, 18H)

IR(cm$^{-1}$) 3630, 3430, 3334, 2930, 2860, 1627, 1511, 754

EXAMPLE 124

1-[N-[2-(3,5-di-tert-butyl-4-hydroxyphenethyl)phenyl]carbamoyl]-4-phenylpiperazine

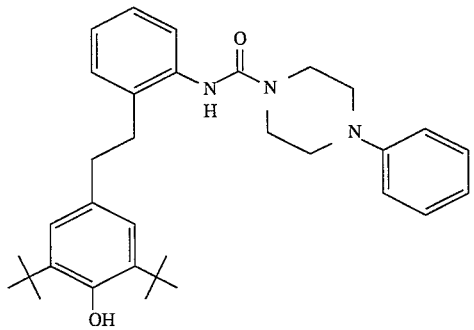

The title compound was prepared in a similar manner to that mentioned in Example 11, using 1-phenylpiperazine instead of decylamine. m.p. 155°–156° C.

$^1$H-NMR(δ ppm, CDCl$_3$) 7.11–7.48(m, 6H), 6.88–6.92(m, 1H), 6.89(d, J=8 Hz, 2H), 6.79(s, 2H), 5.61(t, J=5 Hz, 4H), 3.12(t, J=5 Hz, 4H), 2.83(s, 4H), 1.37(s, 18H)

IR(cm$^{-1}$) 3584, 3372, 2960, 1639, 1601, 1505, 1435, 1234, 999, 753

EXAMPLE 125

8-[N-[2-(3,5-di-tert-butyl-4-hydroxyphenethyl)phenyl]carbamoyl]-1,4-dioxa-8-azaspiro[4.5]decane

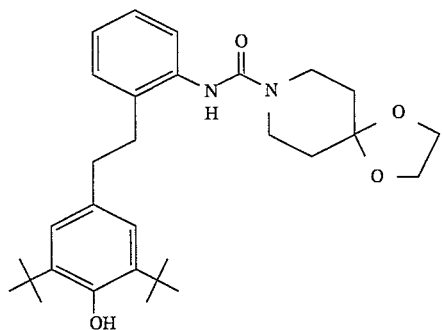

The title compound was prepared in a similar manner to that mentioned in Example 11, using 1,4-dioxa-8-azaspiro[4.5]decane instead of decylamine. m.p. 163°–164° C.

$^1$H-NMR(δ ppm, CDCl$_3$) 7.45(d, J=7 Hz, 1H), 7.17–7.26(m, 2H), 7.12(dd, J=7, 7 Hz, 1H), 6.78(s, 2H), 5.59(bs, 1H), 5.09(s, 1H), 3.96(s, 4H), 3.30(t, J=6 Hz, 4H), 2.82(s, 4H), 1.65(t, J=6 Hz, 4H), 1.36(s, 18H)

IR(cm$^{-1}$) 3430, 3300, 2955, 1645, 1510, 1490, 1455, 1440, 1250, 1120, 950, 750

EXAMPLE 126

1-[N-[2-(3,5-di-tert-butyl-4-hydroxyphenethyl)phenyl]carbamoyl]-4-(1-pyrrolidinylcarbonylmethyl)piperazine

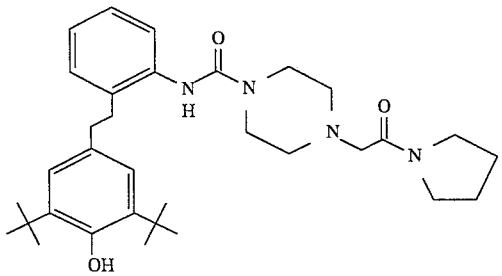

The title compound was prepared in a similar manner to that mentioned in Example 11, using 1-(1-pyrrolidinylcarbonylmethyl)piperazine instead of decylamine.

m.p. 212°–214° C.

$^1$H-NMR(δ ppm, CDCl$_3$) 7.47(d, J=8 Hz, 1H), 7.16–7.25(m, 2H), 7.11(ddd, J=7, 7, 1 Hz, 1H), 6.78(s, 2H), 5.59(s, 1H), 5.10(s, 1H), 3.45–3.52(m, 4H), 3.28(t, J=5 Hz, 4H), 3.11(s, 2H), 2.81(s, 4H), 2.50(t, J=5 Hz, 4H), 1.80–2.00(m, 4H), 1.36(s, 18H)

IR(cm$^{-1}$) 3500, 3328, 2960, 1626, 1521, 1457, 1437, 750

EXAMPLE 127

1-[N-[2-(3,5-di-tert-butyl-4-hydroxyphenethyl)phenyl]carbamoyl]-4-piperidinopiperidine

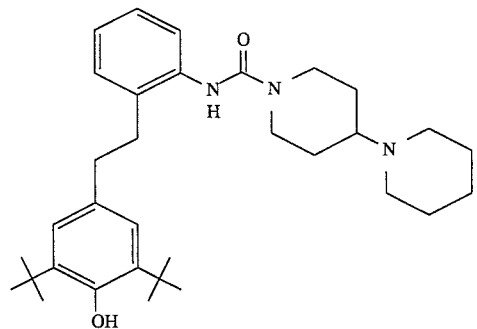

The title compound was prepared in a similar manner to that mentioned in Example 11, using 4-piperidinopiperidine instead of decylamine. m.p. 64°–67° C.

$^1$H-NMR(δ ppm, CDCl$_3$) 7.48(d, J=7 Hz, 1H), 7.16–7.25(m, 2H), 7.11(ddd, J=7, 7, 2 Hz, 1H), 6.79(s, 2H), 5.62(s, 1H), 5.09(s, 1H), 3.73–3.81(m, 2H), 2.81(s, 4H), 2.65–2.75(m, 2H), 2.44–2.51(m, 4H), 2.33–2.44(m, 1H), 1.75–1.82(m, 2H), 1.54–1.62(m, 4H), 1.39–1.50(m, 4H), 1.37(s, 18H)

IR(cm$^{-1}$) 3636, 3420, 2934, 1640, 1520, 1450, 1250, 750

EXAMPLE 128

1-[N-[2-(3,5-di-tert-butyl-4-hydroxyphenethyl)phenyl]carbamoyl]-4-(p-toluenesulfonyl)piperazine

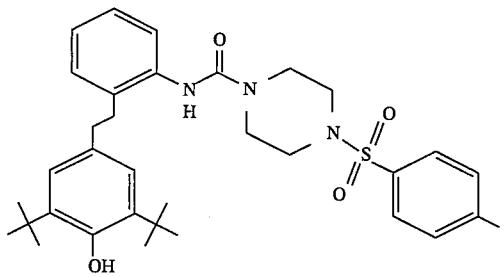

The title compound was prepared in a similar manner to that mentioned in Example 11, using 1-(p-toluenesulfonyl)piperazine instead of decylamine.

m.p. 195°–197° C.

$^1$H-NMR($\delta$ ppm, CDCl$_3$) 7.61(d, J=8 Hz, 2H), 7.29–7.36(m, 3H), 7.19–7.24(m, 3H), 6.73(s, 2H), 5.41(bs, 1H), 5.12(s, 1H), 3.26(t, J=5 Hz, 4H), 2.93(t, J=5 Hz, 4H), 2.70–2.83(m, 4H), 2.45(s, 3H), 1.35(s, 18H)

IR(cm$^{-1}$) 3630, 3410, 2950, 1635, 1625, 1350, 1170, 730

EXAMPLE 129

1-Benzoyl-4-[N-[2-(3,5-di-tert-butyl-4-hydroxyphenethyl)phenyl]carbamoyl]piperazine

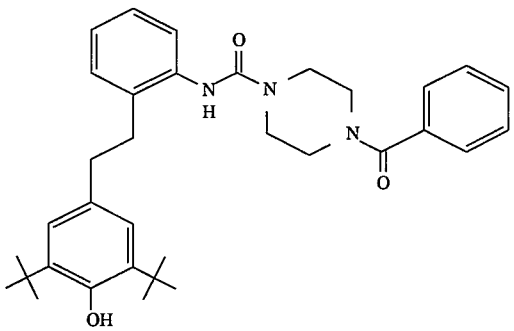

The title compound was prepared in a similar manner to that mentioned in Example 11, using 1-benzoylpiperazine instead of decytamine. m.p. 207°–209° C.

$^1$H-NMR($\delta$ ppm, CDCl$_3$) 7.37–7.48(m, 6H), 7.12–7.27(m, 3H), 6.76(s, 2H), 5.52(bs, 1H), 5.08(s, 1H), 3.12–3.85(m, 8H), 2.82(s, 4H), 1.33(s, 18H)

IR(cm$^{-1}$) 3570, 3266, 2950, 1629, 1530, 1435, 1260, 1007, 754

EXAMPLE 130

1-[N-[2-(3,5-di-tert-butyl-4-hydroxyphenethyl)phenyl]carbamoyl]decahydroquinoline

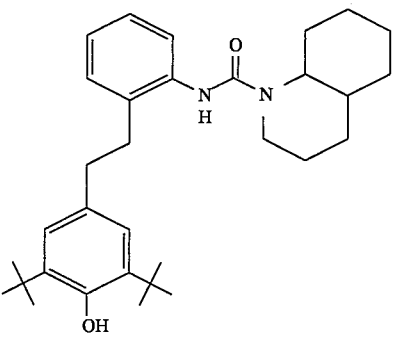

The title compound was prepared in a similar manner to that mentioned in Example 11, using decahydroquinoline instead of decylamine.

$^1$H-NMR($\delta$ ppm, CDCl$_3$) 7.57(d, J=8 Hz, 1H), 7.12–7.21(m, 2H), 7.07(dd, J=7, 7 Hz, 1H), 6.86(s, 2H), 5.88(bs, 1H), 5.08(s, 1H), 4.06(m, 1H), 3.45(m, 1H), 2.75–2.90(m, 5H), 1.90(m, 1H), 1.63–1.80(m, 4H), 1.20–1.60(m, 8H), 1.39(m, 18H)

IR(cm$^{-1}$) 3430, 2924, 1632, 1510, 1434, 750

EXAMPLE 131

1-[N-[2-(3,5-di-tert-butyl-4-hydroxyphenethyl)phenyl]carbamoyl]4-pentanoylpiperazine

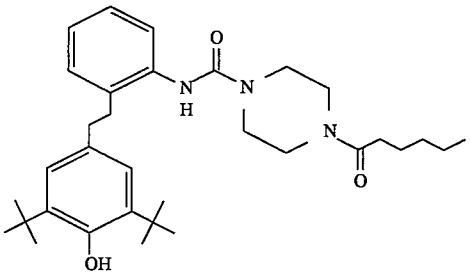

The title compound was prepared in a similar manner to that mentioned in Example 11, using 1-pentanoylpiperazine instead of decylamine. m.p. 126°–128° C.

$^1$H-NMR($\delta$ ppm, CDCl$_3$) 7.44(d, J=9 Hz, 1H), 7.12–7.27(m, 3H), 6.77(s, 2H), 5.52(bs, 1H), 5.12(s, 1H), 3.56–3.63(m, 2H), 3.40–3.46(m, 2H), 3.27–3.34(m, 2H), 3.08–3.14(m, 2H), 2.82(s, 4H), 2.30(t, J=5 Hz, 2H), 1.58–1.67(m, 2H), 1.36(s, 18H), 1.28–1.38(m, 4H)

IR(cm$^{-1}$) 3300, 2952, 1636, 1530, 1435, 1240, 994, 755

EXAMPLE 132

1-[N-[2-(3,5-di-tert-butyl-4-hydroxystyryl)phenyl]carbamoyl]-4-methylpiperazine

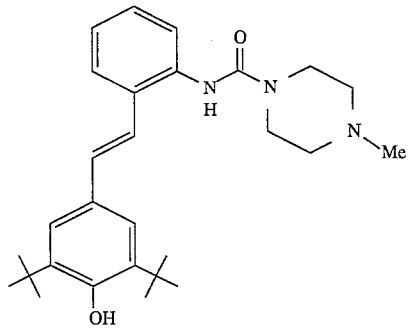

The title compound was prepared in a similar manner to that mentioned in Example 101, using 1-methylpiperazine instead of 2-(aminomethyl)pyridine. m.p. 192°–194° C.

$^1$H-NMR($\delta$ ppm, CDCl$_3$) 7.65(d, J=8 Hz, 1H), 7.46–7.50(m, 1H), 7.33(s, 2H), 7.20–7.26(m, 1H), 7.11(dd, J=9, 1 Hz, 1H), 6.99(d, J=16 Hz, 1H), 6.94(d, J=16 Hz, 1H), 6.39(bs, 1H), 5.34(s, 1H), 3.51(t, J=5 Hz, 4H), 2.43(t, J=8 Hz, 4H), 2.32(m, 3H), 1.47(s, 18H)

IR(cm$^{-1}$) 3636, 3420, 3288, 2952, 1635, 1525, 1485, 1439, 1236, 1149, 959, 765, 755

EXAMPLE 133

1-[N-[2-(3,5-di-tert-butyl-4-hydroxyphenethyl)phenyl]carbamoyl]-4-nicotinoylpiperazine

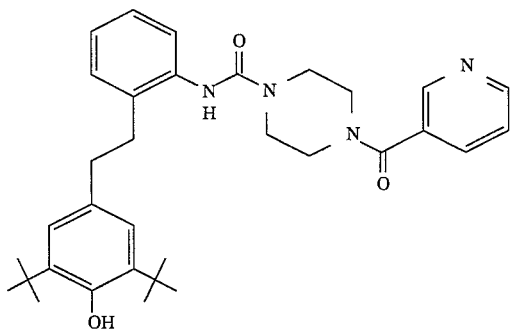

The title compound was prepared in a similar manner to that mentioned in Example 11, using 1-nicotinoylpiperazine instead of decylamine. m.p. 171°–172° C.

$^1$H-NMR($\delta$ ppm, CDCl$_3$) 8.70(dd, J=5, 2 Hz, 1H), 8.66(d, J=1 Hz, 1H), 7.75(ddd, J=8, 8, 2 Hz, 1H), 7.36–7.42(m, 2H), 7.14–7.27(m, 3H), 6.75(s, 2H), 5.52(s, 1H), 5.11(s, 1H), 3.10–3.80(m, 8H), 2.82(s, 4H), 1.33(s, 18)

IR(cm$^{-1}$) 3636, 3420, 3288, 2952, 1635, 1525, 1485, 1439, 1236, 1149, 959, 765, 755

EXAMPLE 134

N-[2-(3,5-di-tert-butyl-4-hydroxyphenethyl)phenyl]-N'-(1-cyclohexyl-4-piperidyl)urea

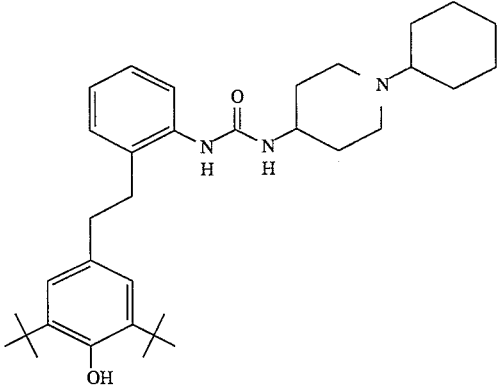

The title compound was prepared in a similar manner to that mentioned in Example 11, using 4-amino-1-cyclohexylpiperidine instead of decylamine.

$^1$H-NMR($\delta$ ppm, CDCl$_3$) 7.15–7.25(m, 4H), 6.79(s, 2H), 5.38(bs, 2H), 5.12(s, 1H), 4.55(bs, 1H), 3.65–3.75(m, 1H), 2.90–2.98(m, 2H), 2.75–2.90(m, 4H), 2.35–2.45(m, 3H), 1.85–2.00(m, 4H), 1.78(bs, 2H), 1.45–1.65(m, 3H), 1.38(s, 18H), 1.00–1.35(m, 5H)

IR(cm$^{-1}$) 3638, 3262, 1658, 1643, 1560, 1542, 1435, 1233, 754

EXAMPLE 135

N-[2-(3,5-di-tert-butyl-4-hydroxyphenethyl)phenyl]-N'-(3-morpholinopropyl)urea

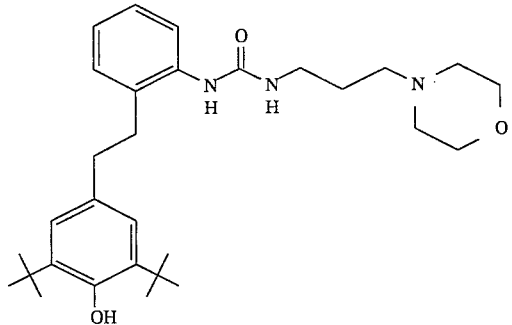

The title compound was prepared in a similar manner to that mentioned in Example 11, using 4-(3-aminopropyl)morpholine instead of decylamine. m.p. 138°–139° C.

$^1$H-NMR($\delta$ ppm, CDCl$_3$)7.19–7.29(m, 4H), 6.80(s, 2H), 5.19(bs, 1H), 5.12(s, 1H), 5.04(t, J=5 Hz, 1H), 3.44(bs, 4H), 3.25(q, J=6 Hz, 2H), 2.77–2.87(m, 4H), 2.25–2.35(m, 6H), 1.60(quint., J=7 Hz, 2H), 1.38(s, 18H)

IR(cm$^{-1}$) 3528, 3304, 1633, 1565, 1436, 1238, 1116, 872,

EXAMPLE 136

N-[2-(3,5-di-tert-butyl-4-hydroxyphenethyl)phenyl]-
N'-(2-morpholinoethyl)urea

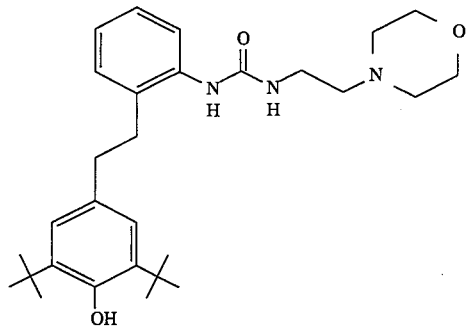

The title compound was prepared in a similar manner to that mentioned in Example 11, using 4-(2-aminoethyl)morpholine instead of decylamine. m.p. 166°–167° C.

$^1$H-NMR(δ ppm, CDCl$_3$) 7.19–7.28(m, 4H), 6.80(s, 2H), 5.19(s, 1H), 5.14(s, 1H), 4.91(s, 1H), 3.56(t, J=6 Hz, 4H), 3.24(t, J=6 Hz, 2H), 2.75–2.89(m, 4H), 2.30–2.42(m, 6H), 1.38(s, 18H)·

IR(cm$^{-1}$) 3566, 3326, 1643, 1574, 1436, 1300, 1238, 755

EXAMPLE 137

N-[2-(3,5-di-tert-butyl-4-hydroxyphenethyl)phenyl]-
N'-[3-(2-methyl-1-piperidyl)propyl]urea

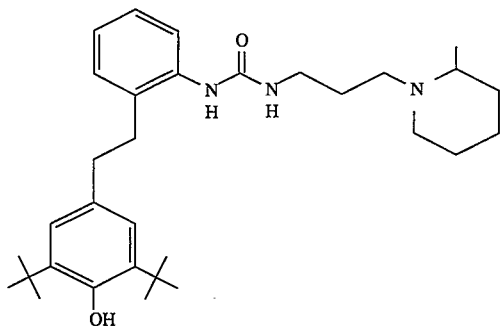

The title compound was prepared in a similar manner to that mentioned in Example 11, using 1-(3-aminopropyl)-2-methylpiperidine instead of decylamine.

$^1$H-NMR(δ ppm, CDCl$_3$) 7.14–7.30(m, 4H), 6.81(s, 2H), 5.43(bs, 1H), 5.36(bs, 1H), 5.11(s, 1H), 3.15–3.30(m, 2H), 2.70–2.87(m, 6H), 2.20–2.30(m, 2H), 2.01(t, J=10 Hz, 1H), 1.40–1.65(m, 5H), 1.38(s, 18H), 1.00–1.40(m, 3H), 0.98(d, J=6 Hz, 3H)

IR(cm$^{-1}$) 3638, 3294, 1643, 1543, 1436, 1234, 754

EXAMPLE 138

N-[2-(3,5-di-tert-butyl-4-hydroxyphenethyl)phenyl]-
N'-[2-(1-pyrrolidinyl)ethyl]urea

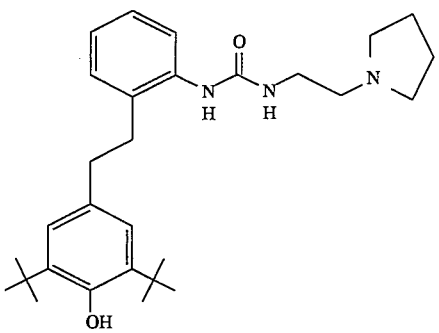

The title compound was prepared in a similar manner to that mentioned in Example 11, using 1-(2-aminoethyl)pyrrolidine instead of decylamine.

$^1$H-NMR(δ ppm, CDCl$_3$) 7.37(d, J=7 Hz, 1H), 7.11–7.21(m, 3H), 6.82(s, 2H), 5.55(bs, 1H), 5.26(s, 1H), 5.03(s, 1H), 3.29(t, J=6 Hz, 2H), 2.65–2.85(m, 5H), 2.59(t, J=6 Hz, 2H), 2.53(bs, 3H), 1.74(bs, 4H), 1.38(s, 18H)

IR(cm$^{-1}$) 3638, 3350, 1686, 1546, 1436, 1234, 753

EXAMPLE 139

N-[2-(3,5-di-tert-butyl-4-hydroxyphenethyl)phenyl]-
N'-[1-(2-propyl)-4-piperidyl]urea

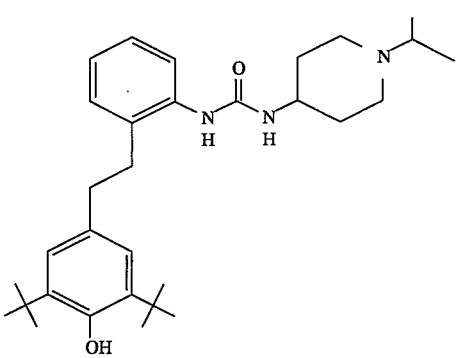

The title compound was prepared in a similar manner to that mentioned in Example 11, using 4-amino-1-(2-propyl)piperidine instead of decylamine. m.p. 191°–193° C.

$^1$H-NMR(δ ppm, CDCl$_3$) 7.15–7.26(m, 4H), 6.78(s, 2H), 5.11(bs, 2H), 4.30(bs, 1H), 3.59–3.72(m, 1H), 2.73–2.90(m, 7H), 2.25–2.37(m, 2H), 1.87–1.98(m, 2H), 1.30–1.50(m, 2H), 1.38(s, 18H), 1.07(d, J=6 Hz, 6H)

IR(cm$^{-1}$) 3358, 2948, 1641, 1561, 1435, 1235

EXAMPLE 140

N-[2-(3,5-di-tert-butyl-4-hydroxyphenethyl)phenyl]-
N'-[2-(4-fluorophenyl)-2-methylpropyl]urea

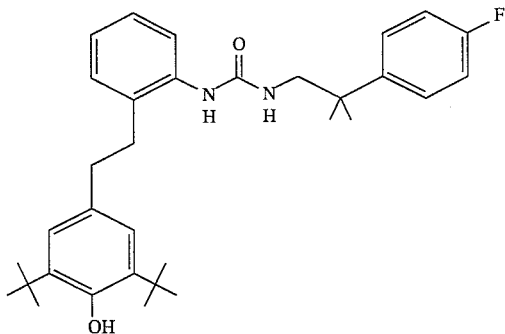

The title compound was prepared in a similar manner to that mentioned in Example 11, using 4-fluoro-β,β-dimethylphenethylamine instead of decylamine. m.p. 179°–180° C.

¹H-NMR(δ ppm, CDCl₃) 7.14–7.20(m, 4H), 7.08(t, J=7 Hz, 1H), 6.87–6.96(m, 3H), 6.74(s, 2H), 5.08(s, 1H), 5.00(s, 1H), 3.95–4.05(m, 1H), 3.30(d, J=6 Hz, 2H), 2.70–2.80(m, 4H), 1.36(s, 18H), 1.24(s, 6H)

IR(cm⁻¹) 3638, 3370, 1644, 1653, 1613, 1436, 1231, 1166, 833, 762

EXAMPLE 141

N-[2-(3,5-di-tert-butyl-4-hydroxyphenethyl)phenyl]-
N'-[2-[4-(1-pyrrolidinyl)phenyl]-2-methylpropyl]urea

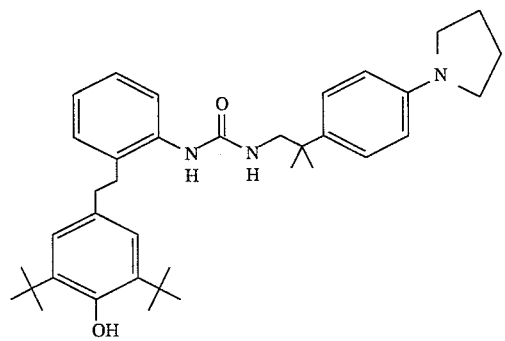

The title compound was prepared in a similar manner to that mentioned in Example 11, using 1-[4-(1-amino-2-methyl-2-propyl)phenyl]pyrrolidine instead of decylamine. m.p. 195°–196° C.

¹H-NMR(δ ppm, CDCl₃) 7.02–7.18(m, 6H), 6.77(s, 2H), 6.43(d, J=9 Hz, 2H), 5.08(s, 2H), 4.14(t, J=6 Hz, 1H), 3.28(t, J=6 Hz, 2H), 3.22–3.25(m, 4H), 2.70–2.78(m, 4H), 1.97–2.01(m, 4H), 1.37(s, 18H), 1.23(s, 6H)

IR(cm⁻¹) 3642, 3354, 1642, 1615, 1562, 1524, 1369, 1234, 814, 750

EXAMPLE 142

N-[2-(3,5-di-tert-butyl-4-hydroxyphenethyl)phenyl]-
N'-(1-benzyl-3-piperidyl)urea

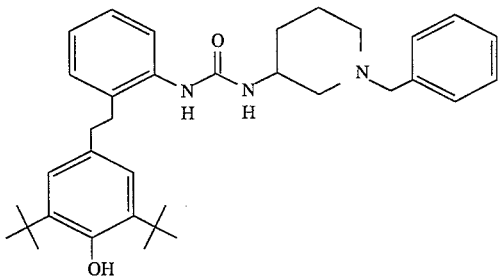

The title compound was prepared in a similar manner to that mentioned in Example 11, using 3-amino-1-benzylpiperidine instead of decylamine.

¹H-NMR(δ ppm, CDCl₃) 7.20–7.40(m, 9H), 6.79(s, 2H), 5.12(bs, 1H), 5.09(s, 1H), 3.87–3.96(m, 1H), 3.49(bs, 1H), 3.37(d, J=13 Hz, 1H), 3.28(d, J=13 Hz, 1H), 2.70–2.90(m, 4H), 2.40–2.50(m, 2H), 1.30–1.70(m, 24H)

IR(cm⁻¹) 3632, 3338, 2948, 1639, 1542, 1435, 1234, 744, 699

EXAMPLE 143

N-[2-(3,5-di-tert-butyl-4-hydroxyphenethyl)phenyl]-
N'-[2-(2-fluorophenyl)-2-methylpropyl]urea

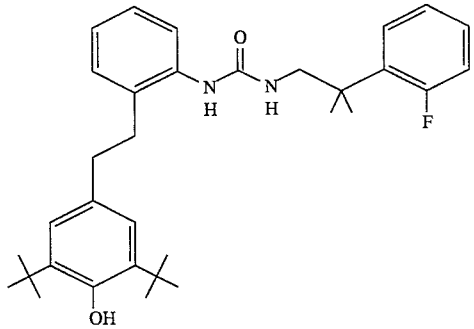

The title compound was prepared in a similar manner to that mentioned in Example 11, using 2-fluoro-β,β-dimethylphenethylamine instead of decylamine. m.p. 182°–183° C.

¹H-NMR(δ ppm, CDCl₃) 6.88–7.21(m, 8H), 6.75(s, 2H), 5.07(s, 1H), 5.02(s, 1H), 4.02–4.09(m, 1H), 3.50(d, J=6 Hz, 2H), 2.67–2.78(m, 4H), 1.36(s, 18H), 1.33(s, 6H)

IR(cm⁻¹) 3650, 3330, 2960, 1640, 1575, 1445, 1255, 765

EXAMPLE 144

N-[2-(3,5-di-tert-butyl-4-hydroxyphenethyl)phenyl]-
N'-[2-(3-fluorophenyl)-2-methylpropyl]urea

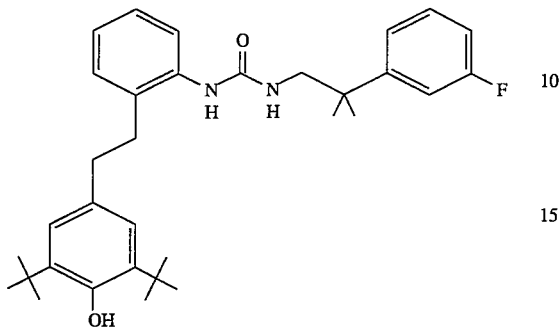

The title compound was prepared in a similar manner to that mentioned in Example 11, using 3-fluoro-β,β-dimethylphenethylamine instead of decylamine. m.p. 165°–166° C.

$^1$H-NMR(δ ppm, CDCl$_3$) 7.04–7.23(m, 4H), 6.80–7.00(m, 4H), 6.74(s, 2H), 5.08(s, 1H), 4.94(s, 1H), 3.98(t, J=6 Hz, 1H), 3.32(d, J=6 Hz, 2H), 2.68–2.79(m, 4H), 1.36(s, 18H), 1.25(s, 6H)

IR(cm$^{-1}$) 3640, 3350, 2970, 1645, 1615, 1590, 1560, 1440, 910, 765, 700

EXAMPLE 145

N-[2-(3,5-di-tert-butyl-4-hydroxyphenethyl)phenyl]-
N'-(1-benzyl-4-piperidyl)-N'-ethylurea

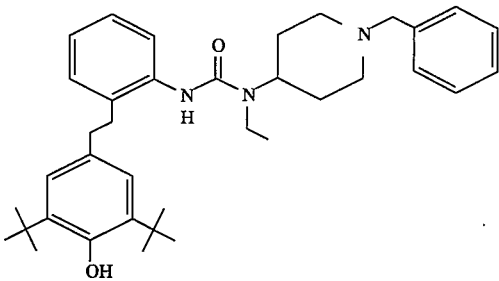

The title compound was prepared in a similar manner to that mentioned in Example 11, using 4-ethylamino-1-benzylpiperidine instead of decylamine. m.p. 149°–151° C.

$^1$H-NMR(δ ppm, CDCl$_3$) 7.72(d, J=8 Hz, 1H), 7.15–7.33(m, 7H), 7.07(t, J=7 Hz, 1H), 6.83(s, 2H), 5.91(bs, 1H), 5.07(s, 1H), 4.16–4.38(m, 1H), 3.48(s, 2H), 3.02(q, J=7 Hz, 2H), 2.93(d, J=12 Hz, 2H), 2.82(bs, 4H), 2.03–2.10(m, 2H), 1.60–1.75(m, 4H), 1.37(s, 18H), 1.16(t, J=7 Hz, 3H)

IR(cm$^{-1}$) 3334, 2954, 1631, 1520, 1502, 1263, 1202, 743

EXAMPLE 146

N-[2-(3,5-di-tert-butyl-4-hydroxyphenethyl)phenyl]-
N'-(1-benzyl-4-piperidyl)-N'-propylurea

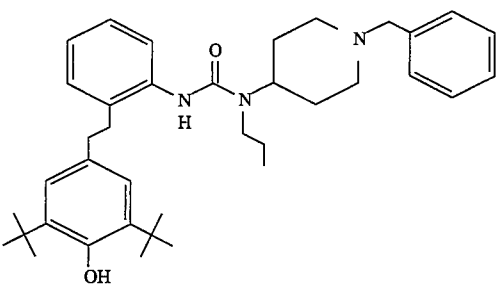

The title compound was prepared in a similar manner to that mentioned in Example 11, using 1-benzyl-4-propylaminopiperidine instead of decylamine.

$^1$H-NMR(δ ppm, CDCl$_3$) 7.76(d, J=7 Hz, 1H), 7.10–7.35(m, 7H), 7.04(td, J=6, 1 Hz, 1H), 6.87(s, 2H), 6.07(bs, 1H), 5.06(s, 1H), 4.12–4.23(m, 1H), 3.48 (s, 2H), 3.04(bt, J=8 Hz, 2H), 2.94(d, J=12 Hz, 2H), 2.81(s, 4H), 2.00–2.10(m, 2H), 1.50–1.75(m, 6H), 1.39(s, 18H), 0.86(t, J=7 Hz, 3H), IR(cm$^{-1}$) 3634, 3450, 2956, 1650, 1509, 1451, 1234, 742

EXAMPLE 147

N-[2-(3,5-di-tert-butyl-4-hydroxyphenethyl)phenyl]-
N'-(1-benzyl-4-piperidyl)-N'-(2-propyl)urea

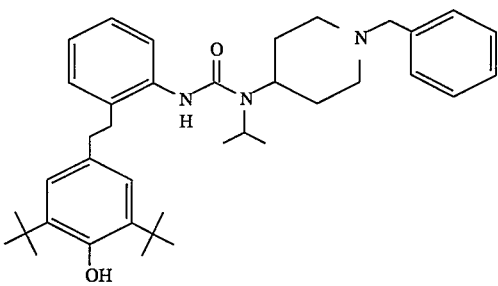

The title compound was prepared in a similar manner to that mentioned in Example 11, using 1-benzyl-4-[(2-propyl)amino]piperidine instead of decylamine.

$^1$H-NMR(δ ppm, CDCl$_3$) 7.65(d, J=8 Hz, 1H), 7.10–7.30(m, 7H), 7.04(td, J=7, 1 Hz, 1H), 6.89(s, 2H), 6.03(bs, 1H), 5.05(s, 1H), 3.70–3.90(m, 2H), 3.47(s, 2H), 2.75–2.98(m, 6H), 1.90–2.05(m, 4H), 1.55–1.70(m, 2H), 1.39(s, 18H), 1.31(d, J=7 Hz, 6H)

IR(cm$^{-1}$) 3450, 2954, 1650, 1521, 1451, 1237, 744

EXAMPLE 148

N-[2-(3,5-di-tert-butyl-4-hydroxyphenethyl)phenyl]-N'-[1-(2-fluorobenzyl)-4-piperidyl]urea

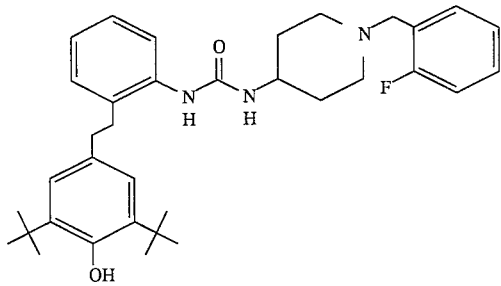

The title compound was prepared in a similar manner to that mentioned in Example 11, using 4-amino-1-(2-fluorobenzyl)piperidine instead of decylamine.

m.p. 136°–137° C.

$^1$H-NMR($\delta$ ppm, CDCl$_3$) 7.14–7.34(m, 6H), 6.95–7.10(m, 2H), 6.77(s, 2H), 5.10(s, 1H), 4.99(s, 1H), 4.10(d, J=8 Hz, 1H), 3.55–3.71(m, 1H), 3.52(s, 2H), 2.68–2.88(m, 6H), 2.07–2.17(m, 2H), 1.82–1.90(m, 2H), 1.37(s, 18H), 1.24–1.35(m, 2H)

IR(cm$^{-1}$) 3640, 3340, 2960, 1650, 1590, 1570, 1495, 1235, 765

EXAMPLE 149

N-[2-(3,5-di-tert-butyl-4-hydroxyphenethyl)phenyl]-N'-[1-(3-fluorobenzyl)-4-piperidyl]urea

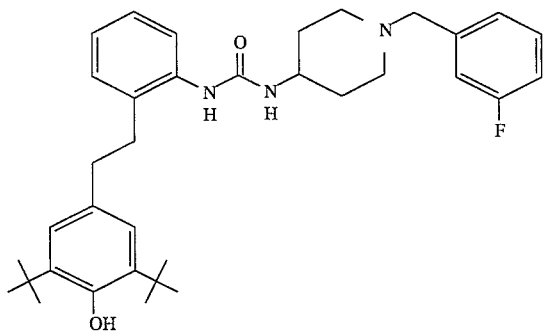

The title compound was prepared in a similar manner to that mentioned in Example 11, using 4-amino-1-(3-fluorobenzyl)piperidine instead of decylamine. m.p. 99°–100° C.

$^1$H-NMR($\delta$ ppm, CDCl$_3$) 7.15–7.27(m, 5H), 7.67–7.04(m, 2H), 6.86–6.94(m, 1H), 5.10(s, 1H), 4.12(d, J=8 Hz, 1H), 3.57–3.70(m, 1H), 3.42(s, 2H), 2.66–2.86(m, 6H), 2.06(t, J=12 Hz, 2H), 1.86(d, J=12 Hz, 2H), 1.38(s, 18H), 1.24–1.35(m, 2H)

IR(cm$^{-1}$) 3635, 3340, 2950, 1640, 1590, 1565, 1490, 1440, 1235, 880, 750, 690

EXAMPLE 150

N-[2-(3,5-di-tert-butyl-4-hydroxyphenethyl)phenyl]-N'-[1-(4-chlorobenzyl)-4-piperidyl]urea

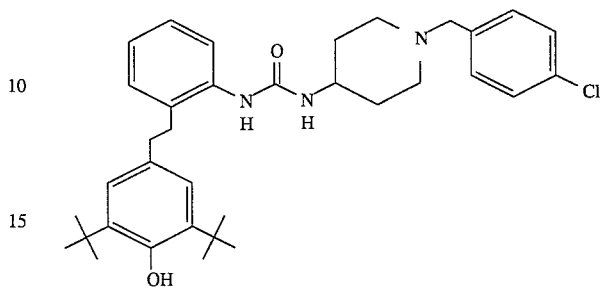

The title compound was prepared in a similar manner to that mentioned in Example 11, using 4-amino-1-(4chlorobenzyl)piperidine instead of decylamine.

m.p. 184°–185° C.

$^1$H-NMR($\delta$ ppm, CDCl$_3$) 7.15–7.32(m, 8H), 6.77(s, 2H), 5.10(s, 1H), 4.98(s, 1H), 4.09(d, J=8 Hz, 1H), 3.57–3.70(m, 1H), 3.39(s, 2H), 2.74–2.87(m, 4H), 2.69(d, J=11 Hz, 2H), 2.04(t, J=11 Hz, 2H), 1.81–1.88(m, 2H), 1.37(s, 18H), 1.14–1.22(m, 2H)

IR(cm$^{-1}$) 3645, 3360, 2940, 1640, 1590, 1555, 1490, 1435, 1295, 1235, 1095, 750

EXAMPLE 151

N-[2-(3,5-di-tert-butyl-4-hydroxyphenethyl)phenyl]-N'-[1-(3,4-difluorobenzyl)-4-piperidyl]urea

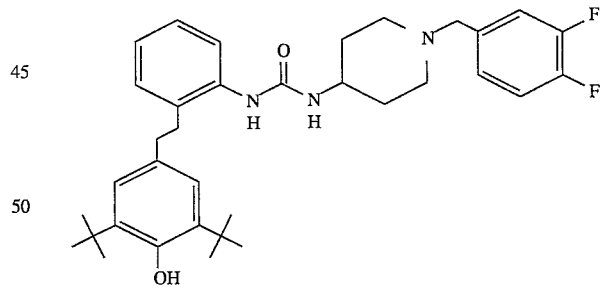

The title compound was prepared in a similar manner to that mentioned in Example 11, using 4-amino-1-(3,4-difluorobenzyl)piperidine instead of decylamine.

m.p. 155°–156° C.

$^1$H-NMR($\delta$ ppm, CDCl$_3$) 6.92–7.28(m, 7H), 6.77(s, 2H), 5.10(s, 1H), 4.97(s, 1H), 4.08(d, J=8 Hz, 1H), 3.58–3.72(m, 1H), 3.37(s, 2H), 2.74–2.87(m, 4H), 2.05(t, J=11 Hz, 2H), 1.82–1.90(m, 2H), 1.38(s, 18H), 1.24–1.35(m, 2H)

IR(cm$^{-1}$) 3650, 3370, 2965, 1645, 1570, 1525, 1440, 1295, 1240, 885, 785, 765

EXAMPLE 152

N-[2-(3,5-di-tert-butyl-4-hydroxyphenethyl)phenyl]-N'-[1-(4-fluorophenethyl)-4-piperidyl]urea

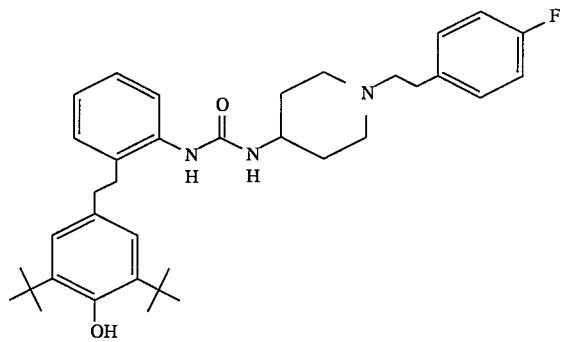

The title compound was prepared in a similar manner to that mentioned in Example 11, using 4-amino-1-(4-fluorophenethyl)piperidine instead of decylamine.

m.p. 117°–119° C.

$^1$H-NMR($\delta$ ppm, CDCl$_3$) 7.10–7.20(m, 6H), 6.94(td, J=7, 2 Hz, 2H), 6.78(s, 2H), 5.11(s, 1H), 5.04(bs, 1H), 4.13(bd, J=8 Hz, 1H), 3.58–3.70(m, 1H), 2.70–2.90(m, 8H), 2.45–2.55(m, 2H), 2.08–2.12(m, 2H), 1.85–1.95(m, 2H), 1.30–1.40(m, 2H), 1.38(s, 18H)

IR(cm$^{-1}$) 3630, 3314, 2948, 1634, 1565, 1510, 1228, 748

EXAMPLE 153

N-[2-(3,5-di-tert-butyl-4-hydroxyphenethyl)phenyl]-N'-[1-(3,5-difluorobenzyl)-4-piperidyl]urea

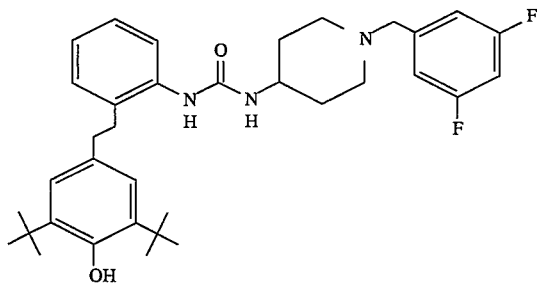

The title compound was prepared in a similar manner to that mentioned in Example 11, using 4-amino-1-(3,5-difluorobenzyl)piperidine instead of decylamine.

m.p. 119°–120° C.

$^1$H-NMR($\delta$ ppm, CDCl$_3$) 7.17–7.28(m, 4H), 6.82(d, J=6 Hz, 2H), 6.77(s, 2H), 6.62–6.69(m, 1H), 5.11(s, 1H), 4.97(s, 1H), 4.09(d, J=8 Hz, 1H), 3.58–3.71(m, 1H), 3.40(s, 2H), 2.66–2.88(m, 6H), 2.07(t, J=11 Hz, 2H), 1.83–1.92(m, 2H), 1.38(s, 18H), 1.25–1.36(m, 2H)

IR(cm$^{-1}$) 3640, 3350, 2960, 1635, 1605, 1505, 1440, 1325, 1235, 1120, 995, 855

EXAMPLE 154

2-[N-[2-(3,5-di-tert-butyl-4-hydroxyphenethyl)phenyl]carbamoyl]-cis-decahydroquinoline

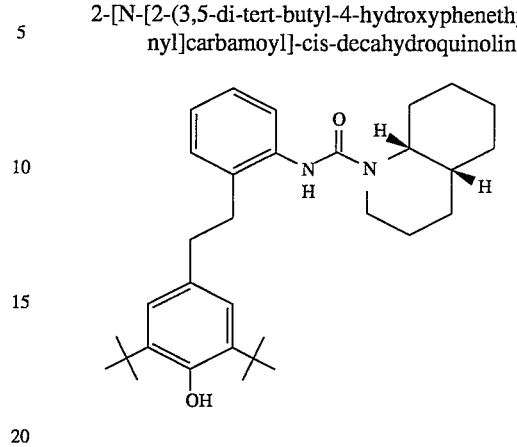

The title compound was prepared in a similar manner to that mentioned in Example 11, using cis-decahydroquinoline instead of decylamine. m.p. 132°–133° C.

$^1$H-NMR($\delta$ ppm, CDCl$_3$) 7.64(d, J=8 Hz, 1H), 7.23–7.30(m, 2H), 7.11(t, J=7 Hz, 1H), 6.93(s, 2H), 5.94(s, 1H), 5.14(s, 1H), 4.09–4.20(m, 1H), 3.48–3.59(m, 1H), 2.83–2.94(m, 5H), 1.50–2.00(m, 9H), 1.45(s, 18H), 1.24–1.42(m, 4H)

IR(cm$^{-1}$) 3640, 3320, 2925, 2860, 1630, 1515, 1435, 1360, 1275, 1235, 1160, 755

EXAMPLE 155

N-[2-(3,5-di-tert-butyl-4-hydroxyphenethyl)-3-fluorophenyl]-N'-(1-benzyl-4-piperidyl)urea

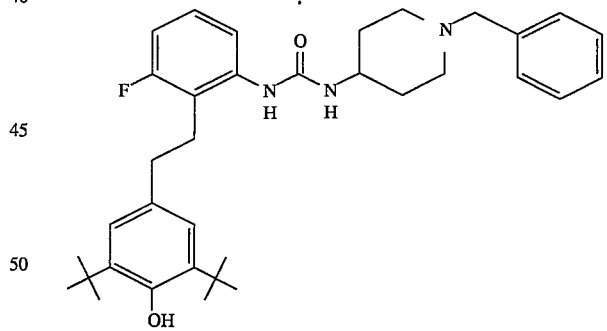

The title compound was prepared in a similar manner to that mentioned in Example 108, using 4-(2-amino-6-fluorophenethyl)-2,6-di-tert-butylphenol instead of 4-(2-amino-3,5-difluorophenethyl)-2,6-di-tert-butylphenol.

m.p. 103°–105° C.

$^1$H-NMR($\delta$ ppm, CDCl$_3$) 7.20–7.35(m, 5H), 7.13(t, J=8 Hz, 1H), 7.03(d, J=8 Hz, 1H), 6.93(t, J=9 Hz, 1H), 6.75(s, 2H), 5.13(s, 1H), 4.60(bs, 1H), 3.95(bd, J=8 Hz, 1H), 3.54–3.66(m, 1H), 3.44(s, 2H), 2.70–2.90(m, 6H), 2.00–2.10(m, 2H), 1.80–1.90(m, 2H), 1.30–1.40(m, 2H), 1.36(s, 18H)

IR(cm$^{-1}$) 3630, 3300, 2948, 1632, 1565, 1452, 1235, 699

EXAMPLE 156

N-[2-(3,5-di-tert-butyl-4-hydroxyphenethyl)phenyl]-N'-[1-(4-fluorobenzyl)-4-piperidyl]-N'-methylurea

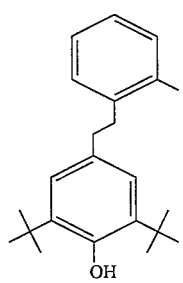

The title compound was prepared in a similar manner to that mentioned in Example 11, using 1-(4-fluorobenzyl)-4-(methylamino)piperidine instead of decylamine. m.p. 177°–178° C.

$^1$H-NMR($\delta$ ppm, CDCl$_3$) 7.63(d, J=8 Hz, 1H), 7.17–7.28(m, 4H), 7.08–7.13(m, 1H), 6.95–7.03(m, 2H), 6.78(s, 2H), 5.61(s, 1H), 5.08(s, 1H), 4.17–4.28(m, 1H), 3.43(s, 2H), 2.90(d, J=12 Hz, 2H), 2.81(s, 4H), 2.50(s, 3H), 1.98–2.07(m, 2H), 1.54–1.68(m, 4H), 1.35(s, 18H)

IR(cm$^{-1}$) 3630, 3330, 2970, 1635, 1520, 1440, 1330, 1230, 1050, 760,

EXAMPLE 157

N-[2-(3,5-di-tert-butyl-4-hydroxystyryl)phenyl]-N'-[1-(4-fluorobenzyl)-4-piperidyl]-N'-methylurea

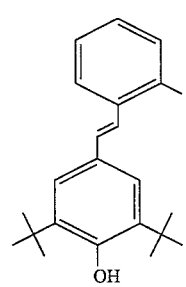

The title compound was prepared in a similar manner to that mentioned in Example 101, using 1-(4-fluorobenzyl)-4-(methylamino)piperidine instead of 2-(aminomethyl)pyridine. m.p. 174°–175° C.

$^1$H-NMR($\delta$ ppm, CDCl$_3$) 7.79(d, J=8 Hz, 1H), 7.45(dd, J=7, 1 Hz, 1H), 7.31(s, 2H), 7.20–7.30(m, 3H), 7.05–7.13(m, 1H), 6.93–7.03(m, 4H), 6.38(s, 1H), 5.32(s, 1H), 4.14–4.26(m, 1H), 3.46(s, 2H), 2.85–2.96(m, 5H), 1.99–2.10(m, 2H), 1.63–1.82(m, 4H), 1.46(s, 18H)

IR(cm$^{-1}$) 3640, 3450, 2960, 1640, 1510, 1225, 1160, 1045, 965, 760

EXAMPLE 158

N-[2-(3,5-di-tert-butyl-4-hydroxystyryl)phenyl]-N'-(1-benzy4-piperidyl)-N'-methylurea

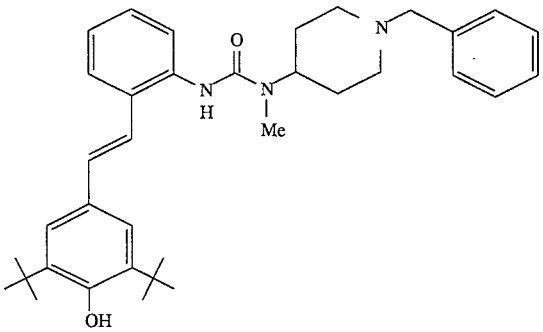

The title compound was prepared in a similar manner to that mentioned in Example 101, using 1-benzyl-4-(methylamino)piperidine instead of 2-(aminomethyl)pyridine. m.p. 163°–164° C.

$^1$H-NMR($\delta$ ppm, CDCl$_3$) 7.78(d, J=7 Hz, 1H), 7.45(dd, J=8, 1 Hz, 1H), 7.20–7.35(m, 8H), 7.04–7.12(m, 1H), 7.00(d, J=16 Hz, 1H), 6.93(d, J=16 Hz, 1H), 6.38(s, 1H), 5.32(s, 1H), 4.14–4.27(m, 1H),3.48(s, 2H), 2.94(d, J=12 Hz, 2H), 2.90(s, 3H), 2.00–2.11(m, 2H), 1.60–1.84(m, 4H), 1.46(s, 18H)

IR(cm$^{-1}$) 3625, 3440, 3260, 2960, 1625, 1530, 1485, 1240, 1150, 1045, 960, 755, 745, 700

EXAMPLE 159

2-[N-[2-(3,5-di-tert-butyl-4-hydroxystyryl)phenyl] carbamoyl]-cis-decahydroquinoline

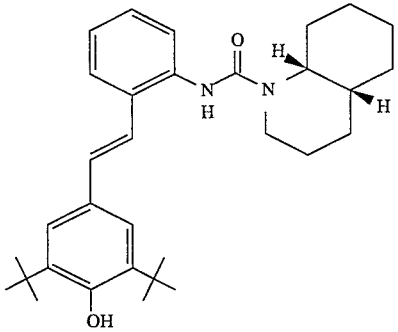

The title compound was prepared in a similar manner to that mentioned in Example 101, using cis-decahydroquinoline instead of 2-(aminomethyl)pyridine.

$^1$H-NMR($\delta$ ppm, CDCl$_3$) 7.71(d, J=8 Hz, 1H), 7.46(d, J=6 Hz, 1H), 7.33(s, 2H), 7.20–7.28(m, 1H), 7.05–7.11(m, 1H), 7.00(d, J=16 Hz, 1H), 6.93(d, J=16 Hz, 1H), 6.41(s, 1H), 5.32(s, 1H), 3.85–4.07(m, 2H), 1.68–1.97(m, 5H), 1.47–1.64(m, 5H), 1.47(s, 18H), 1.18–1.43(m, 3H)

IR(cm$^{-1}$) 3640, 3450, 3300, 2930, 2870, 1645, 1525, 1445, 1240, 1160, 965, 755

EXAMPLE 160

N-[4-(3,5-di-tert-butyl-4-hydroxyphenethyl)phenyl]-N'-(1-benzyl-4-piperidyl)urea

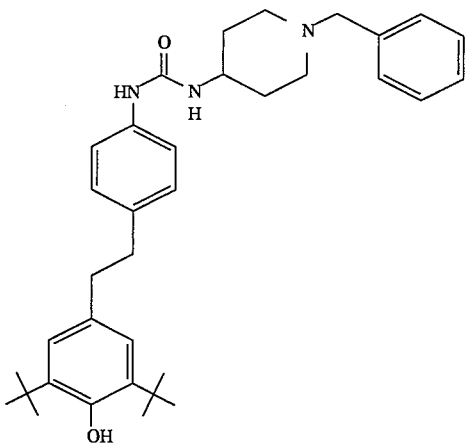

The title compound was prepared in a similar manner to that mentioned in Example 11, using 4-(4-aminophenethyl)-2,6-di-tert-butylphenol instead of 4-(2-aminophenethyl)-2,6-di-tert-butylphenol and using 4-amino-1-benzylpiperidine instead of decylamine. m.p. 195°–197° C.

$^1$H-NMR(δ ppm, CDCl$_3$) 7.22–7.34(m, 5H), 7.15(s, 4H), 6.92(s, 2H), 6.10(s, 1H), 5.06(s, 1H), 4.56(d, J=8 Hz, 1H), 3.66–3.78(m, 1H), 3.49(s, 2H), 2.75–2.90(m, 6H), 2.07–2.18(m, 2H), 1.91–1.99(m, 2H), 1.36–1.47(m, 2H), 1.43(s, 18H)

IR(cm$^{-1}$) 3620, 3378, 2946, 1659, 1604, 1542, 1515, 1435, 1324, 1234, 740

EXAMPLE 161

N-[2-(3,5-di-tert-butyl-4-hydroxyphenethyl)phenyl]-N'-allylurea

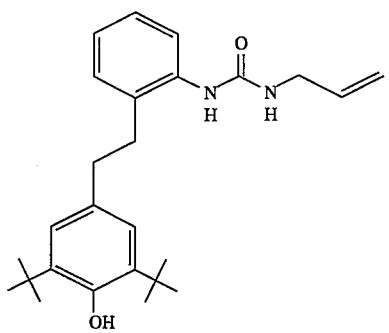

The title compound was prepared in a similar manner to that mentioned in Example 11, using allylamine instead of decylamine. m.p. 169°–172° C.

$^1$H-NMR(δ ppm, CDCl$_3$) 7.16–7.32(m, 5H), 6.78(s, 2H), 5.73–5.85(m, 1H), 4.96–5.14(m, 3H), 4.20–4.26(m, 1H), 3.73–3.80(m, 2H), 2.76–2.90(m, 4H), 1.37(s, 18H)

IR(cm$^{-1}$) 3632, 3334, 2956, 1653, 1587, 1570, 1561, 1436, 1235, 924, 769

EXAMPLE 162

N-[2-(3,5-di-tert-butyl-4-hydroxyphenethyl)phenyl]-N'-(4-nitrophenethyl)urea

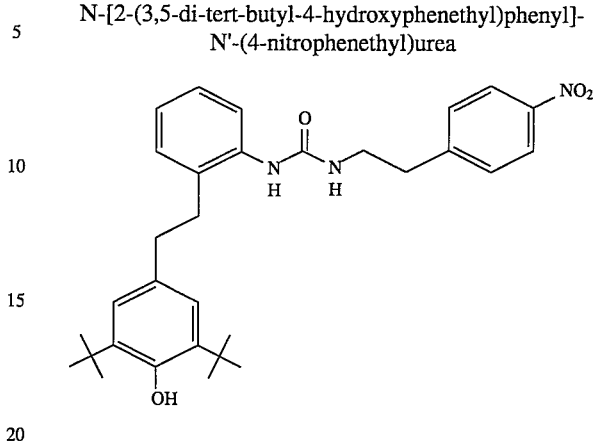

The title compound was prepared in a similar manner to that mentioned in Example 11, using 4-nitrophenethylamine instead of decylamine. m.p. 134°–136° C.

$^1$H-NMR(δ ppm, CDCl$_3$) 8.08(d, J=8 Hz, 1H), 7.10–7.29(m, 6H), 6.75(s, 2H), 5.12(s, 1H), 5.05(s, 1H), 4.28(t, J=6 Hz, 1H), 3.39(td, J=7, 6 Hz, 2H), 2.73–2.90(m, 6H), 1.35(s, 18H)

IR(cm$^{-1}$) 3630, 3314, 2954, 1639, 1561, 1519, 1436, 1347, 753

EXAMPLE 163

N-[2-(3,5-di-tert-butyl-4-hydroxyphenethyl)-6-methoxyphenyl]-N'-(1-benzyl-4-piperidyl)urea

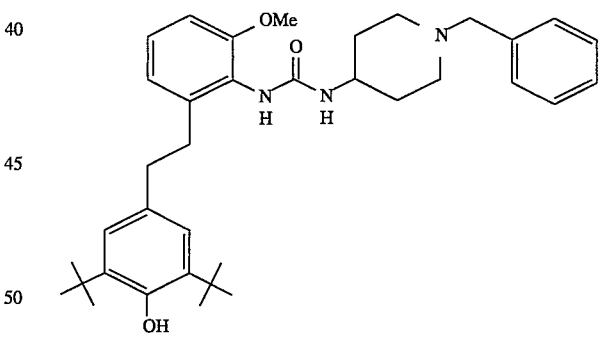

The title compound was prepared in a similar manner to that mentioned in Example 108, using 4-(2-amino-3-methoxyphenethyl)-2,6-di-tert-butylphenol instead of 4-(2-amino-3,5-difluorophenethyl)-2,6-di-tert-butylphenol.

m.p. 184°–185° C.

$^1$H-NMR(δ ppm, CDCl$_3$) 7.20–7.30(m, 6H), 6.88(d, J=8 Hz, 1H), 6.80(s, 2H), 6.77(d, J=8 Hz, 1H), 5.07(s, 1H), 4.88(s, 1H), 4.09(d, J=8 Hz, 1H), 3.76(s, 3H), 3.60–3.70(m, 1H), 3.43(s, 2H), 2.86–2.90(m, 2H), 2.70–2.77(m, 4H), 2.05(t, J=11 Hz, 2H), 1.86(d, J=10 Hz, 2H), 1.38(s, 18H), 1.25(q, J=10 Hz, 2H), IR(cm$^{-1}$) 3638, 3308, 1653, 1589, 1563, 1556, 1468, 1454, 1435, 1260, 1232, 738

EXAMPLE 164

N-[2-(3,5-di-tert-butyl-4-hydroxyphenethyl)phenyl]-N'-[endo-9-(4-fluorobenzyl)-3-oxa-9-azabicyclo[3.3.1]non-7-yl]urea

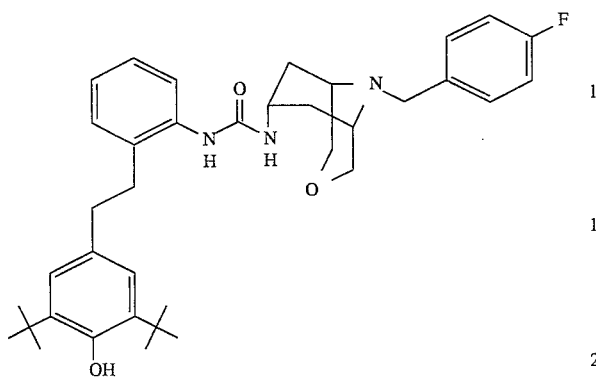

The title compound was prepared in a similar manner to that mentioned in Example 11, using endo-7-amino-9-(4-fluorobenzyl)-3-oxa-9-azabicyclo[3.3.1]nonane instead of decylamine.

$^1$H-NMR($\delta$ ppm, CDCl$_3$) 7.18–7.29(m, 6H), 7.06(d, J=11 Hz, 1H), 6.99 (d, J=9 Hz, 1H), 6.96 (d, J=9 Hz, 1H), 6.83 (s, 2H), 5.22(s, 1H), 5.09(s, 1H), 4.37(dd, J=17, 7 Hz, 1H), 3.73(d, J=15 Hz, 2H), 3.71(s, 2H), 3.39(d, J=11 Hz, 2H), 2.84–2.87(m, 2H), 2.76–2.79(m, 2H), 2.52(s, 2H), 2.30–2.37(m, 2H), 1.39(s, 18H), 1.31–1.40(m, 2H)

IR(cm$^{-1}$) 3636, 3324, 1652, 1525, 1511, 1506, 1436, 1223, 787, 759

EXAMPLE 165

N-[2-(3,5-di-tert-butyl-4-hydroxyphenethyl)-4,6-difluorophenyl]-N'-(1-benzyl-4-piperidyl)-N'-methylurea

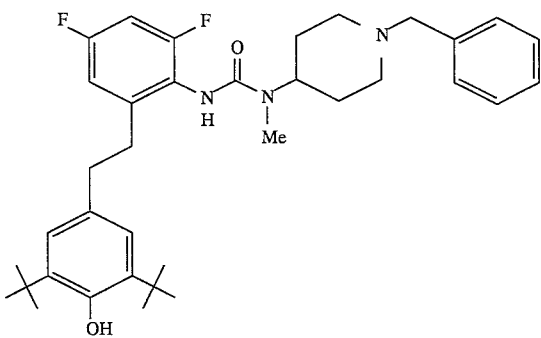

The title compound was prepared in a similar manner to that mentioned in Example 108, using 1-benzyl-4-(methylamino)piperidine instead of 4-amino-1-benzylpiperidine.
m.p. 187°–191° C.

$^1$H-NMR($\delta$ ppm, CDCl$_3$) 7.20–7.40(m, 5H), 6.70–6.80(m, 4H), 5.09(s, 1H), 4.91(bs, 1H), 4.10–4.23(m, 1H), 3.47(s, 2H), 2.90–3.00(m, 2H), 2.80–2.90(m, 4H), 2.58(s, 3H), 2.00–2.10(m, 2H), 1.60–1.80(m, 4H), 1.36(s, 18H)

IR(cm$^{-1}$) 3616, 3312, 1638, 1510, 1436, 1323, 1118

EXAMPLE 166

2-[N-[2-(3,5-di-tert-butyl-4-hydroxyphenethyl)-4,6-difluorophenyl]carbamoyl]-cis-decahydroquinoline

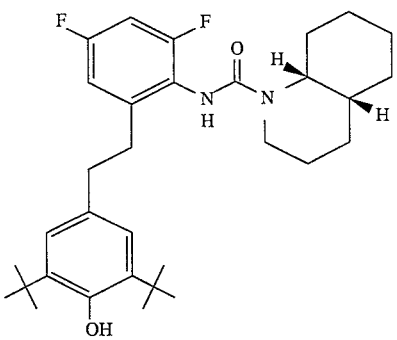

The title compound was prepared in a similar manner to that mentioned in Example 108, using cis-decahydroquinoline instead of 4-amino-1-benzylpiperidine.
m.p. 83°–85° C.

$^1$H-NMR($\delta$ ppm, CDCl$_3$) 6.83(s, 2H), 6.70–6.80(m, 2H), 5.26(bs, 1H), 5.09(s, 1H), 4.05(bs, 1H), 3.49(bs, 2H), 2.70–2.90(m, 5H), 1.84–1.94(m, 1H), 1.65–1.80(m, 4H), 1.20–1.60(m, 8H), 1,39(s, 18H)

IR(cm$^{-1}$) 3588, 3316, 2924, 1713, 1638, 1511, 1435, 1120

EXAMPLE 167

N-[2-(3,5-di-tert-butyl-4-hydroxyphenethyl)-4,6-difluorophenyl]-N'-(1-benzyl-4-piperidyl)urea hydrochloride

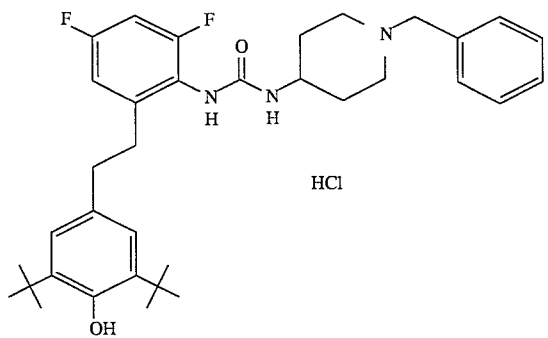

N-[2-(3,5-di-tert-butyl-4-hydroxyphenethyl)-4,6-difluorophenyl]-N'-(1-benzyl-4-piperidyl)urea (1.15 g) was suspended in ethanol (20 ml) and heated at 50° C. to dissolve it. To the solution was added 4N hydrochloric acid/ethyl acetate solution (anhydrous)(0.5 ml). This solution was concentrated to a volume of 5 ml, cooled to 0°–5° C. and allowed to stand for 4 hrs. The resultant crystals were filtered and dried to afford the title compound (1.00 g, 81%).
m.p. 170°–175° C.

$^1$H-NMR($\delta$ ppm, CDCl$_3$) 12.09(bs, 1H), 7.55(d, J=6 Hz, 2H), 7.30–7.40(m, 3H), 6.84(s, 2H), 6.72(d, J=8 Hz, 1H), 6.65(td, J=8, 2 Hz, 1H), 5.10(s, 1H), 4.12(d, J=7 Hz, 1H), 3.75–3.86(m, 1H), 3.35–3.40(m, 2H), 2.65–2.85(m, 6H), 2.10–2.25(m, 4H), 1.39(s, 18H)

IR(cm$^{-1}$) 3430, 3300, 2952, 1680, 1554, 1436, 1236, 1122

EXAMPLE 168

N-[2-(3,5-di-tert-butyl-4-hydroxyphenethyl)-6-methylphenyl]-N'-(1-benzyl-4-piperidyl)urea

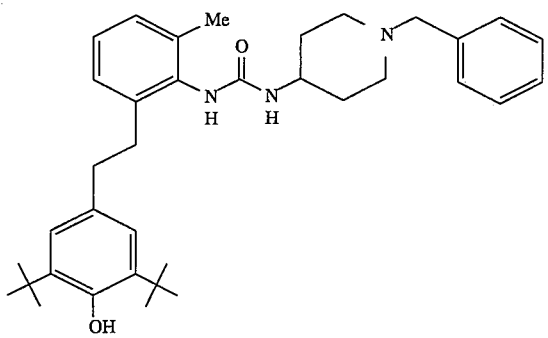

The title compound was prepared in a similar manner to that mentioned in Example 108, using 4-(2-amino-3-methylphenethyl)-2,6-di-tert-butylphenol instead of 4-(2-amino-3,5-difluorophenethyl)-2,6-di-tert-butylphenol.

m.p. 185°–186° C.

$^1$H-NMR($\delta$ ppm, CDCl$_3$) 7.04–7.34(m, 8H), 6.78(s, 2H), 5.08(s, 1H), 4.83(s, 1H), 3.90(d, J=8 Hz, 1H), 3.57–3.72(m, 1H), 3.42(s,2H), 2.62–2.90(m, 6H), 2.19(s, 3H), 2.03(dd, J=12, 11 Hz, 2H), 1.83(d, J=11 Hz, 2H), 1.38(s, 18H), 1.16–1.32(m, 2H)

IR(cm$^{-1}$) 3638, 3324, 2950, 1639, 1555, 1436, 1233, 769, 734, 698

EXAMPLE 169

N-[2-(3,5-di-tert-butyl-4-hydroxyphenethyl)-4,6-difluorophenyl]-N'-(1-benzyl-4-piperidyl)urea methanesulfonate

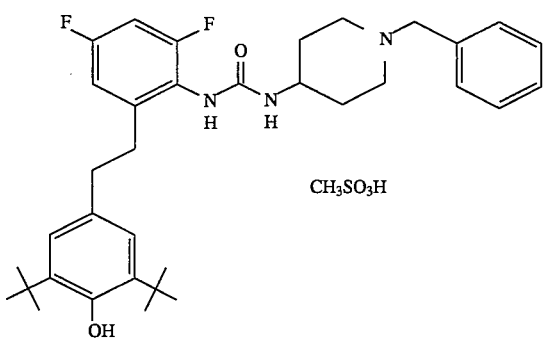

N-[2-(3,5-di-tert-butyl-4-hydroxyphenethyl)-4,6-difluorophenyl]-N'-(1-benzyl-4-piperidyl)urea (0.50 g) was suspended in ethanol (10 ml) and heated at 50° C. to dissolve it. To the solution was added methanesulfonic acid (56 µl) and this solution was concentrated. The concentrate was dissolved with a mixed solvent of ethyl acetate (1 ml) and diisopropylether (3 ml). The solution was cooled to 0°–5° C. and allowed to stand overnight. The resultant crystals were filtered and dried to give the title compound (0.51 g, 87%).

m.p. 252°–254° C.

$^1$H-NMR($\delta$ ppm, CDCl$_3$) 10.23(bs, 1H), 7.30–7.45(m, 5H), 6.80–6.92(m, 3H), 6.57–6.68(m, 1H), 5.10(s, 1H), 4.30(bs, 1H), 4.12(bs, 1H), 3.74–3.88(m, 1H), 3.40–3.50(m, 2H), 3.20–3.32(m, 1H), 2.60–2.80(m, 9H), 1.90–2.15(m, 4H), 1.39(s, 18H)

IR(cm$^{-1}$) 3262, 2954, 1657, 1562, 1438, 1220, 1163, 1119, 1041

EXAMPLE 170

(S)-N-[2-(3,5-di-tert-butyl-4-hydroxyphenethyl)phenyl]-N'-(α-methoxycarbonyl)benzylurea

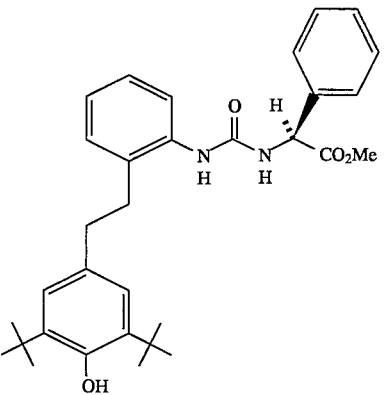

The title compound was prepared in a similar manner to that mentioned in Example 11, using (S)-α-phenylglycine methyl ester instead of decylamine.

m.p. 145°–150° C.

$^1$H-NMR($\delta$ ppm, CDCl$_3$) 7.170–7.34(m, 9H), 6.76(s, 2H), 5.51(d, J=8 Hz, 1H), 5.23(d, J=7 Hz, 1H), 5.13(s, 1H), 5.09(s, 1H), 3.68(s, 3H), 2.74–2.88(m, 4H), 1.35(s, 18H)

IR(cm$^{-1}$) 3644, 3345, 2944, 1752, 1644, 1546, 1436, 1211

EXAMPLE 171

N-[2-(3,5-di-tert-butyl-4-hydroxyphenethyl)phenyl]-N'-(2,4-dimethyl-1,8-naphthyridin-7-yl)urea

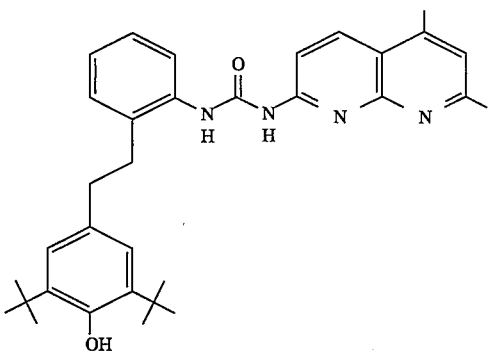

The title compound was prepared in a similar manner to that mentioned in Example 11, using 7-amino-2,4-dimethyl-1,8-naphthyridine instead of decylamine.

m.p. 235°–237° C.

$^1$H-NMR($\delta$ ppm, CDCl$_3$) 8.22(d, J=9 Hz, 1H), 7.86–7.96(m, 1H), 7.10–7.30(m, 3H), 7.02(s, 1H), 6.80(s, 2H), 4.93(s, 1H), 3.15–3.27(m, 2H), 2.90–3.01(m, 2H), 2.62(s, 3H), 2.56(bs, 3H), 23(s, 18H)

IR(cm$^{-1}$) 3636, 2952, 1687, 1615, 1599, 1560, 1527, 1403, 1307, 751

EXAMPLE 172

N-[2-(3,5-di-tert-butyl-4-hydroxyphenethyl)phenyl]-N'-(bicyclo[3.3.0]-2-octyl)urea

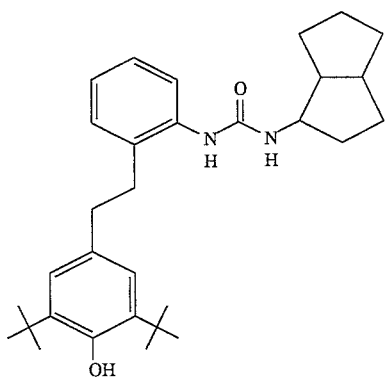

The title compound was prepared in a similar manner to that mentioned in Example 11, using 1-aminobicyclo[3.3.0]octane instead of decylamine.

$^1$H-NMR($\delta$ ppm, CDCl$_3$) 7.14–7.29(m, 4H), 6.80(s, 2H), 5.11(s, 1H), 5.060(s, 1H), 4.15(d, J=8 Hz, 1H), 3.62–3.72(m, 1H), 2.75–2.88(m, 4H), 2.34–2.45(m, 1H), 1.87–2.01(m, 2H), 1.72–1.83(m, 1H), 1.43–1.63(m, 4H), 1.38(s, 18H), 1.07–1.31(m, 3H)

IR(cm$^{-1}$) 3634, 2948, 2864, 1637, 1563, 1434, 1231, 760

EXAMPLE 173

(S)-N-[2-(3,5-di-tert-butyl-4-hydroxyphenethyl)phenyl]-N'-($\alpha$-benzyloxycarbonyl)benzylurea

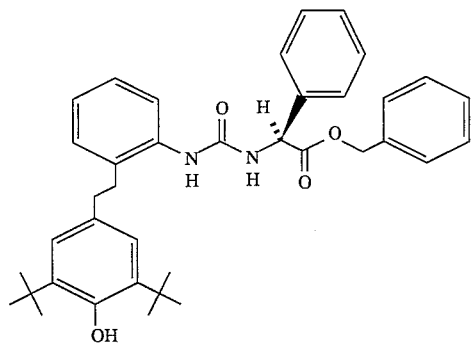

The title compound was prepared in a similar manner to that mentioned in Example 11, using (S)-$\alpha$-phenylglycine benzyl ester instead of decylamine.

m.p. 132°–134° C.

$^1$H-NMR($\delta$ ppm, CDCl$_3$) 7.13–7.33(m, 14H), 6.75(s, 2H), 5.57(d, J=8 Hz, 1H), 5.27(d, J=7 Hz, 1H), 5.15(s, 1H), 5.11(s, 2H), 5.08(s, 1H), 2.74–2.87(m, 4H), 1.34(s, 18H)

IR(cm$^{-1}$) 3642, 3344, 2944, 1749, 1643, 1587, 1553, 1168, 749, 697

EXAMPLE 174

1-[N-[2-(3,5-di-tert-butyl-4-hydroxyphenethyl)phenyl]carbamoyl]-2-ethylpiperidine

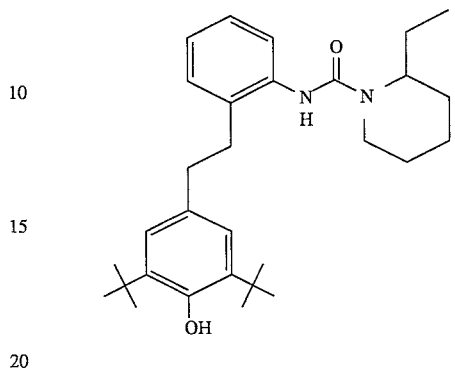

The title compound was prepared in a similar manner to that mentioned in Example 11, using 2-ethylpiperidine instead of decylamine. m.p. 137°–138° C.

$^1$H-NMR($\delta$ ppm, CDCl$_3$) 7.52–7.58(m, 1H), 7.16–7.23(m, 2H), 7.04–7.10(m, 1H), 6.84(s, 2H), 5.78(s, 1H), 5.08(s, 1H), 3.91–4.00(m, 1H), 3.51–3.61(m, 1H), 2.76–2.87(m, 5H), 1.45–1.80(m, 8H), 1.38(s, 18H), 0.86(t, J=7 Hz, 3H)

IR(cm$^{-1}$) 3450, 3300, 2960, 1640, 1510, 1490, 1455, 1250, 885, 765

EXAMPLE 175

1-[N-[2-(3,5-di-tert-butyl-4-hydroxyphenethyl)phenyl]carbamoyl]-3-methylpiperidine

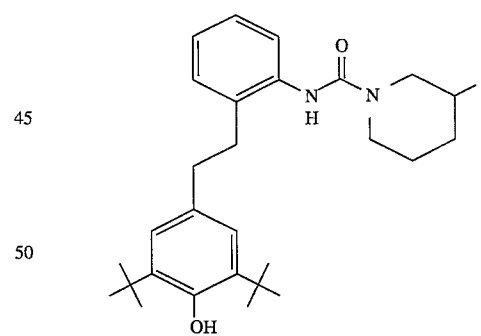

The title compound was prepared in a similar manner to that mentioned in Example 11, using 3-methylpiperidine instead of decylamine.

$^1$H-NMR($\delta$ ppm, CDCl$_3$) 7.49–7.54(m, 1H), 7.16–7.24(m, 2H), 7.07–7.13(m, 1H), 6.83(s, 2H), 5.72(s, 1H), 5.09(s, 1H), 3.80–3.87(m, 1H), 3.46–3.54(m, 1H), 2.82(s, 4H), 2.70–2.82(m, 2H), 2.35–2.44(m, 1H), 1.76–1.84(m, 1H), 1.40–1.67(m, 3H), 1.38(s, 18H), 1.02–1.14(m, 1H), 0.88(t, J=6 Hz, 3H)

IR(cm$^{-1}$) 3645, 3430, 3310, 2960, 2870, 1640, 1525, 1435, 1250, 1150, 750

EXAMPLE 176

1-[N-[2-(3,5-di-tert-butyl-4-hydroxyphenethyl)phenyl]carbamoyl]-2-[2-(benzyloxy)ethyl]piperidine

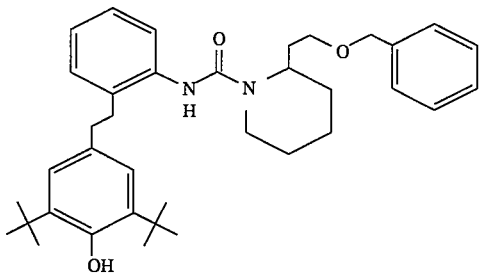

The title compound was prepared in a similar manner to that mentioned in Example 11, using 2-[2-(benzyloxy)ethyl]methylpiperidine instead of decylamine.

m.p. 113°–114° C.

$^1$H-NMR($\delta$ ppm, CDCl$_3$) 7.53(d, J=8 Hz, 1H), 7.02–7.22(m, 8H), 6.89(s, 2H), 6.74(bs, 1H), 5.05(s, 1H), 4.35–4.44(m, 2H), 4.23–4.32(m, 1H), 4.03–4.15 (m, 1H), 3.44–3.59(m, 2H), 2.63–2.77(m, 5H), 2.00–2.12(m, 1H), 1.44–1.82(m, 7H), 1.37(s, 18H)

IR(cm$^{-1}$) 3600, 3420, 2940, 2870, 1665, 1595, 1535, 1450, 1400, 1380, 1270, 1240, 1100, 765, 745

EXAMPLE 177

1-[N-[2-(3,5-di-tert-butyl-4-hydroxyphenethyl)phenyl]carbamoyl]-3,3-dimethylpiperidine

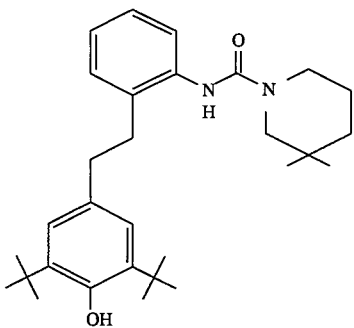

The title compound was prepared in a similar manner to that mentioned in Example 11, using 3,3-dimethylpiperidine instead of decylamine.

$^1$H-NMR($\delta$ ppm, CDCl$_3$) 7.54(dd, J=8, 1 Hz, 1H), 7.16–7.23(m, 2H), 7.04–7.12(m, 1H), 6.84(s, 2H), 5.77(s, 1H), 5.08(s, 1H), 3.19(t, J=6 Hz, 2H), 3.05(s, 2H), 2.82(s, 4H), 1.52–1.61(m, 2H), 1.33–1.43(m, 2H), 1.39(s, 18H), 0.92(s, 6H)

IR(cm$^{-1}$) 3645, 3430, 3320, 2960, 2870, 1640, 1520, 1440, 1250, 1165, 755

EXAMPLE 178

N-[2-(3,5-di-tert-butyl-4-hydroxyphenethyl)phenyl]-N'-(4-fluorobenzyl)-N'-methylurea

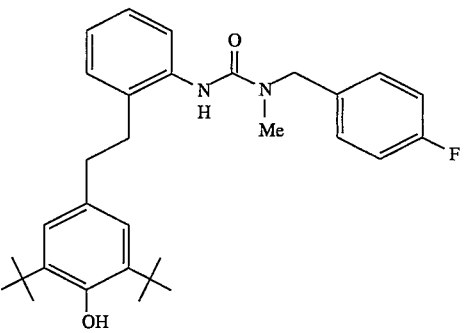

The title compound was prepared in a similar manner to that mentioned in Example 11, using 4-fluoro-N-methylphenethylamine instead of decylamine.

$^1$H-NMR($\delta$ ppm, CDCl$_3$) 7.63(d, J=8 Hz, 1H), 7.17–7.26(m, 4H), 7.11(dd, J=8, 7 Hz, 1H), 6.97(dd, J=9, 9 Hz, 2H), 6.75(s, 2H), 5.66(s, 1H), 5.06(s, 1H), 4.45(s, 2H), 2.73–2.84(m, 4H), 2.64 (s, 3H), 1.33(s, 18H)

IR(cm$^{-1}$) 3645, 3430, 3320, 2965, 1650, 1515, 1440, 1380, 1300, 1230, 1160, 760

EXAMPLE 179

N-[2-(3,5-di-tert-butyl-4-hydroxyphenethyl)phenyl]-N'-(3,4-methylenedioxybenzyl)-N'-methylurea

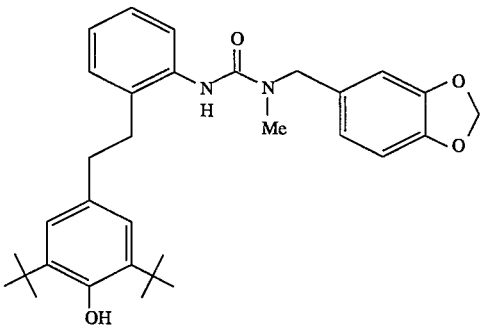

The title compound was prepared in a similar manner to that mentioned in Example 11, using 5-(methylaminomethyl)-1,3-dioxaindane instead of decylamine.

m.p. 152°–153° C.

¹H-NMR(δ ppm, CDCl₃) 7.65(d, J=8 Hz, 1H), 7.16–7.25(m, 2H), 7.10(dd, J=7, 7 Hz, 1H), 6.76(s, 2H), 6.65–6.73(m, 2H), 5.92(s, 2H), 5.69(s, 1H), 5.06(s, 1H), 4.39(s, 2H), 2.72–2.83(m, 4H), 2.66(s, 3H), 1.34(s, 18H)

EXAMPLE 180

1-[N-[2-(3,5-di-tert-butyl-4-hydroxyphenethyl)phenyl]carbamoyl]-3-(benzyloxy)piperidine

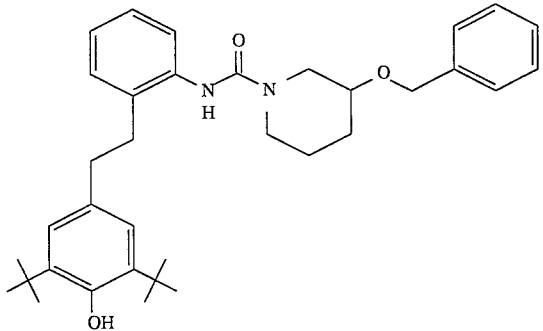

The title compound was prepared in a similar manner to that mentioned in Example 11, using 3-benzyloxypiperidine instead of decylamine.

¹H-NMR(δ ppm, CDCl₃) 7.44(d, J=8 Hz, 1H), 7.22–7.34(m, 5H), 7.18(dd, J=7 Hz, 1H), 7.08 (dd, J =7, 7 Hz, 1H), 6.80 (s, 2H), 5.82(s, 1H), 5.06(s, 1H), 4.47–4.56(m, 2H), 3.68–3.76(m, 1H), 3.43–3.51(m, 1H), 3.09–3.22(m, 3H), 2.71–2.83(m, 4H), 1.61–1.96(m, 3H), 1.38–1.50(m, 1H), 1.36(s, 18H)

IR(cm⁻¹) 3625, 3280, 2960, 1635, 1525, 1490, 1445, 1245, 1045, 940, 765

EXAMPLE 181

1-[N-[2-(3,5-di-tert-butyl-4-hydroxyphenethyl)phenyl]carbamoyl]-2-(2-hydroxyethyl)piperidine

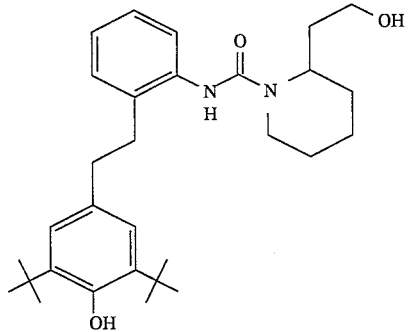

The title compound was prepared in a similar manner to that mentioned in Example 11, using 2-(2-hydroxyethyl)piperidine instead of decylamine.

¹H-NMR(δ ppm, CDCl₃) 7.46(d, J=8 Hz, 1H), 7.16–7.24(m, 2H), 7.11(ddd, J=8, 7, 1 Hz, 1H), 6.84(s, 2H), 6.00–6.21(br, 1H), 5.08(s, 1H), 4.51–4.62(m, 1H), 3.57–3.66(m, 1H), 3.48–3.18(m, 3H), 2.69–2.88(m, 5H), 1.40–2.03(m, 8H), 1.38(s, 18H)

IR(cm⁻¹) 3640, 3320, 2950, 2870, 1640, 1530, 1440, 1275, 1230, 1175, 755

EXAMPLE 182

1-[N-[2-(3,5-di-tert-butyl-4-hydroxyphenethyl)phenyl]carbamoyl]-2-(2-acetoxyethyl)piperidine

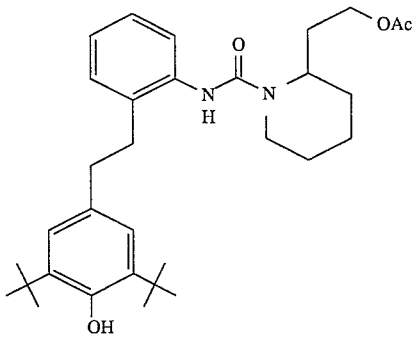

The title compound was prepared in a similar manner to that mentioned in Example 11, using 2-(2-acetoxyethyl)piperidine instead of decylamine.

¹H NMR(δ ppm, CDCl₃) 7.49(d, J=8 Hz, 1H), 7.17–7.23(m, 2H), 7.09(d, J=7 Hz, 1H), 6.84(s, 2H), 5.84(s, 1H), 5.08(s, 1H), 4.33–4.43(m, 1H), 4.00–4.16(m, 2H), 3.41–3.51(m, 1H), 2.76–2.90(m, 5H), 2.00–2.12(m, 1H), 1.97(s, 3H), 1.74–1.85(m, 1H), 1.38–1.72(m, 6H), 1.38(s, 18H)

IR(cm⁻¹) 3640, 3425, 2960, 2870, 1740, 1640, 1520, 1435, 1370, 1235, 750

EXAMPLE 183

N-[2-(3,5-di-tert-butyl-4-hydroxyphenethyl)-5-chlorophenyl]-N'-(1-benzyl-4-piperidyl)urea

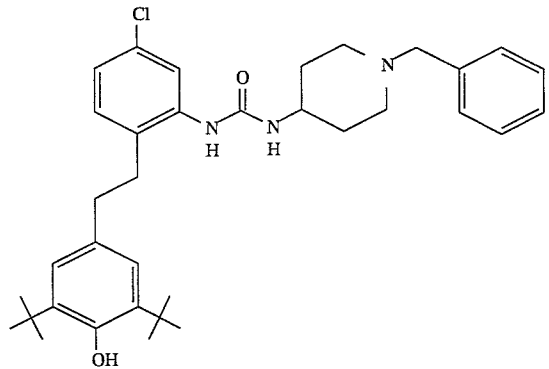

The title compound was prepared in a similar manner to that mentioned in Example 108, using 4-(2-amino-4-chlorophenethyl)-2,6-di-tert-butylphenol instead of 4-(2-amino-3,5-difluorophenethyl)-2,6-di-tert-butylphenol.

m.p. 155°–156° C.

¹H-NMR(δ ppm, CDCl₃) 7.41(s, 1H), 7.22–7.31(m, 5H), 7.08(s, 2H), 6.77(s, 2H), 5.22(s, 1H), 5.12(s, 1H), 4.20(d, J=8 Hz, 1H), 3.45–3.65(m, 1H), 3.45(s, 2H), 2.75(s, 4H), 2.73–2.77(m, 2H), 2.04(t, J=11 Hz, 2H), 1.85(d, J=11 Hz, 2H), 1.38(s, 18H), 1.22–1.42(m, 2H)

IR(cm⁻¹) 3645, 3370, 1633, 1545, 1438, 1234, 699

EXAMPLE 184

N-[2-(3,5-di-tert-butyl-4-hydroxyphenethyl)-5-chlorophenyl]-N'-[2-(2-fluorophenyl)-2-methylpropyl]-N'-methylurea

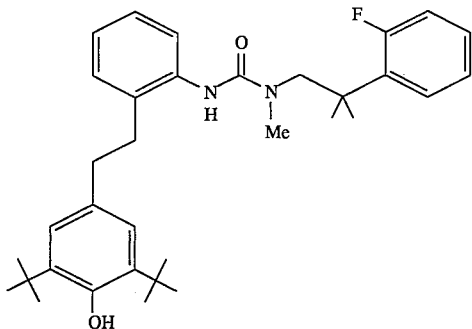

The title compound was prepared in a similar manner to that mentioned in Example 11, using 2-fluoro-β,β-dimethylphenethylamine instead of decylamine.

$^1$H-NMR(δ ppm, CDCl$_3$) 7.53(d, J=8 Hz, 1H), 7.17–7.28(m, 4H), 7.05–7.14(m, 2H), 6.94–7.03(m, 1H), 6.73(s, 2H), 5.49(s, 1H), 5.01(s, 1H), 3.70(s, 2H), 2.73–2.83(m, 4H), 2.21(s, 3H), 1.37(s, 6H), 1.29(s, 18H)

IR(cm$^{-1}$) 3640, 3430, 2965, 1660, 1510, 1490, 1440, 1210, 760

EXAMPLE 185

N-[2-(3,5-di-tert-butyl-4-hydroxyphenethyl)-5-chlorophenyl]-N'-methyl-N'-[1-(3,4-methylenedioxyphenyl)cyclopentyl]methylurea

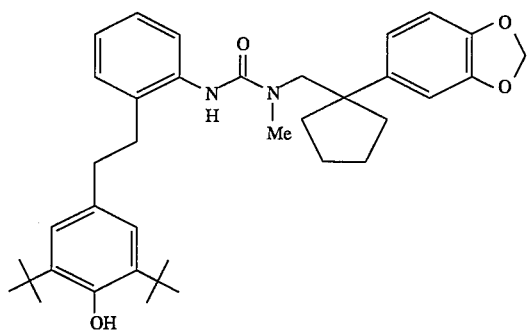

The title compound was prepared in a similar manner to that mentioned in Example 11, using 5-[1-(N-methylaminomethyl)cyclopentyl]-1,3-dioxaindane instead of decylamine.

$^1$H-NMR(δ ppm, CDCl$_3$) 7.45(d, J=7 Hz, 1H), 7.16–7.24(m, 2H), 7.06–7.13(m, 1H), 6.78(s, 1H), 6.72(s, 4H), 5.92(s, 2H), 5.32(s, 1H), 5.03(s, 1H), 3.42(s, 2H), 2.73–2.82(s, 4H), 2.02(s, 3H), 2.58–2.98(m, 8H), 1.30(s, 18H)

IR(cm$^{-1}$) 3640, 3430, 2960, 1660, 1510, 1490, 1435, 1235, 1450, 760

EXAMPLE 186

N-[2-(3,5-di-tert-butyl-4-hydroxyphenethyl)-5-chlorophenyl]-N'-(α-methylbenzyl)urea

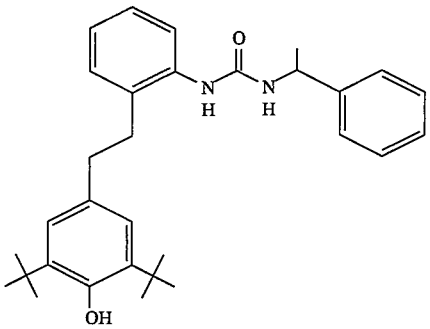

The title compound was prepared in a similar manner to that mentioned in Example 11, using α-methylbenzylamine instead of decylamine. m.p. 167°–168° C.

$^1$H-NMR(δ ppm, CDCl$_3$) 7.12–7.33(m, 9H), 6.77(s, 2H), 5.15(s, 1H), 5.09(s, 1H), 4.96(dq, J=7, 7 Hz, 1H), 4.53(d, J=7 Hz, 1H), 2.70–2.82(m, 4H), 1.40(d, J=7 Hz, 3H), 1.37(s, 18H)

IR(cm$^{-1}$) 3625, 3320, 3275, 2960, 1630, 1565, 1435, 1235, 745, 700

EXAMPLE 187

N-[2-(3,5-di-tert-butyl-4-hydroxyphenethyl)-5-chlorophenyl]-N'-[2-(3,4-dichlorophenyl)-2-methylpropyl]-N'-methylurea

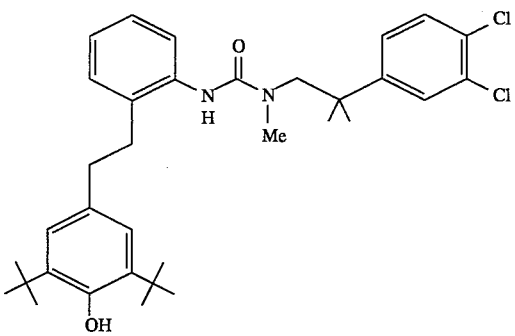

The title compound was prepared in a similar manner to that mentioned in Example 11, using N-methyl-3,4-dichloro-β,β-dimethylphenethylamine instead of decylamine.

$^1$H-NMR(δ ppm, CDCl$_3$) 7.48(d, J=8 Hz, 1H), 7.43(d, J=2 Hz, 1H), 7.37(d, J=10 Hz, 1H), 7.17–7.27(m, 3H), 7.09–7.15(m, 1H), 6.71(s, 2H), 5.38(s, 1H), 5.08(s, 1H), 3.48(s, 2H), 2.72–2.84(m, 4H), 2.13(s, 3H), 1.36(s, 6H), 1.29(s, 18H)

IR(cm$^{-1}$) 3640, 3430, 3330, 2970, 1660, 1515, 1480, 1450, 1440, 1310, 1250, 1030, 880, 760

EXAMPLE 188

N-[2-(3,5-di-tert-butyl-4-hydroxyphenethyl)-5-chlorophenyl]-N'-[4-(4-fluorobenzyl)-3-morpholinyl]methylurea

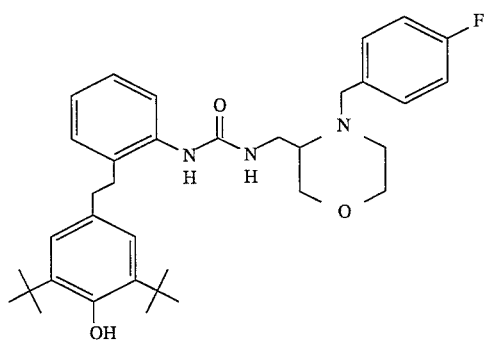

The title compound was prepared in a similar manner to that mentioned in Example 11, using 3-methylamino-4-(4-fluorobenzyl)morpholine instead of decylamine.

$^1$H-NMR($\delta$ ppm, CDCl$_3$) 7.19–7.37(m, 4H), 6.80–6.89(m, 4H), 6.76(s, 2H), 5.11(s, 1H), 5.05(s, 1H), 4.96(bs, 1H), 3.89(d, J=13 Hz, 1H), 3.74(dd, J=12, 3 Hz, 1H), 3.64(d, J=12 Hz, 1H), 3.31–3.42(m, 4H), 3.03(d, J=13 Hz, 1H), 2.70–2.88(m, 4H), 2.48–2.56(m, 1H), 2.45(d, J=12 Hz, 1H), 2.10(dt J=11, 3 Hz, 1H), 1.37(s, 18H)

EXAMPLE 189

N-[2-(3,5-di-tert-butyl-4-hydroxyphenethyl)-5-chlorophenyl]-N'-[2-(3,4-dichlorophenyl)-2-propyl]-N'-methylurea

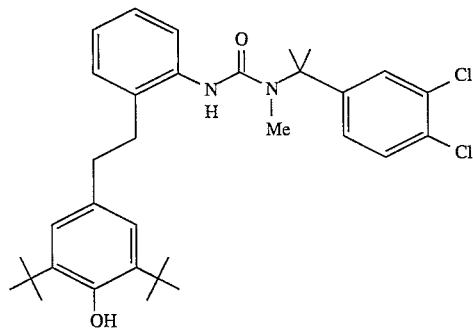

The title compound was prepared in a similar manner to that mentioned in Example 11, using 3,4--dichloro-N,α,α-trimethylbenzylamine instead of decylamine.

$^1$H-NMR($\delta$ ppm, CDCl$_3$) 7.36–7.42(m, 2H), 7.24–7.29(m, 1H), 7.09–7.17(m, 3H), 7.02–7.07(m, 1H), 6.79(s, 2H), 5.52(s, 1H), 5.09(s, 1H), 2.81(s, 3H), 2.61–2.78(m, 4H), 1.63(s, 6H), 1.38(s, 18H)

IR(cm$^{-1}$) 3640, 3290, 2960, 2875, 1640, 1520, 1485, 1440, 1340, 1245, 1140, 1030, 755

EXAMPLE 190

N-[2-(3,5-di-tert-butyl-4-hydroxyphenethyl)-5-chlorophenyl]-N'-[2-(N-benzyl-N-ethylamino)ethyl]urea

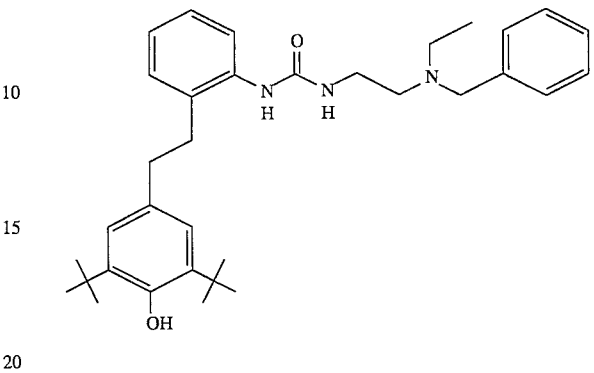

The title compound was prepared in a similar manner to that mentioned in Example 11, using N-benzyl-N-ethylethylenediamine instead of decylamine.

m.p. 132°–133° C.

$^1$H-NMR($\delta$ ppm, CDCl$_3$) 7.16–7.36(m, 7H), 6.92–6.98(m, 2H), 6.79(s, 2H), 5.12(bs, 1H), 5.09(s, 1H), 5.00–5.05(m, 1H), 3.43(s, 2H), 3.21(td, J=6, 5 Hz, 2H), 2.74–2.90(m, 4H), 2.46(t, J=6 Hz, 2H), 2.37(q, J=7 Hz, 2H), 1.38(s, 18H), 0.87(t, J=7 Hz, 3H)

IR(cm$^{-1}$) 3650, 3340, 3280, 2960, 2810, 1640, 1585, 1560, 1440, 1235, 1150, 865, 745, 705

EXAMPLE 191

1-[N-[2-(3,5-di-tert-butyl-4-hydroxyphenethyl)phenyl]carbamoyl]-3-ethoxycarbonylpiperidine

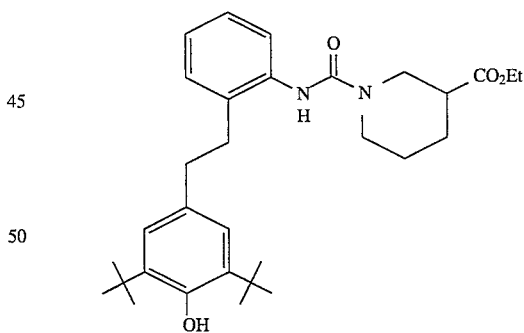

The title compound was prepared in a similar manner to that mentioned in Example 11, using 3-ethoxycarbonylpiperidine instead of decylamine.

$^1$H-NMR($\delta$ ppm, CDCl$_3$) 7.53(d, J=8 Hz, 1H), 7.15–7.22(m, 2H), 7.04–7.09(m, 1H), 6.84(s, 2H), 6.30(s, 1H), 5.07(s, 1H), 4.06–4.15(m, 2H), 3.74–3.81(m, 1H), 3.30–3.42(m, 2H), 3.10–3.17(m, 1H), 2.78–2.92(m, 4H), 2.52–2.59(m, 1H), 1.83–2.00(m, 2H), 1.46–1.66(m, 2H), 1.38(s, 18H), 1.22(t, J=7 Hz, 3H)

IR(cm$^{-1}$) 3425, 2945, 2870, 1725, 1650, 1595, 1530, 1450, 1375, 1300, 1210, 1030, 885, 760

EXAMPLE 192

N-[2-(3,5-di-tert-butyl-4-hydroxyphenethyl)-5-chlorophenyl]-N'-(1-phenylcyclopentyl)-N'-methylurea

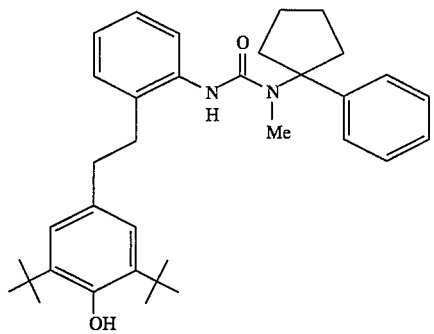

The title compound was prepared in a similar manner to that mentioned in Example 11, using N-methyl-1-phenylcyclopentylamine instead of decylamine.

$^1$H-NMR($\delta$ ppm, CDCl$_3$) 7.47(d, J=8 Hz, 1H), 7.33(dd, J=8, 1 Hz, 1H), 7.08–7.18(m, 3H), 6.93–7.02(m, 3H), 6.78(s, 2H), 5.75(s, 1H), 5.07(s, 1H), 3.15(s, 3H), 2.57(t, J=8 Hz, 2H), 2.23–2.39(m, 4H), 2.20(t, J=8 Hz, 2H), 1.64–1.85(m, 4H), 1.42(s, 18H)

IR(cm$^{-1}$) 3630, 3410, 2950, 1640, 1520, 1440, 1345, 1230, 755, 700

EXAMPLE 193

N-[2-(3,5-di-tert-butyl-4-hydroxyphenethyl)-5-chlorophenyl]-N'-(1-benzyl-4-hydroxy-4-piperidyl)methylurea

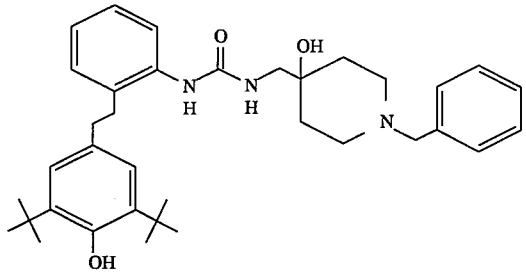

The title compound was prepared in a similar manner to that mentioned in Example 11, using 4-aminomethyl-1-benzyl-4-hydroxypiperidine instead of decylamine.

$^1$H-NMR($\delta$ ppm, CDCl$_3$) 7.15–7.35(m, 9H), 6.76(s, 2H), 5.12(s, 1H), 5.08(bs, 1H), 4.56(t, J=5 Hz, 1H), 3.51(s, 2H), 3.37(bs, 1H), 3.14(d, J=8 Hz, 2H), 2.70–2.85(m, 4H), 2.50–2.60(m, 2H), 2.30–2.40(m, 2H), 1.45–1.60(m, 4H), 1.36(s, 18H)

IR(cm$^{-1}$) 3350, 2952, 1639, 1550, 1435, 1234, 741, 699

EXAMPLE 194

N-[2-(3,5-di-tert-butyl-4-hydroxyphenethyl)-4,6-difluorophenyl]-N'-cyclohexyl-N'-methylurea

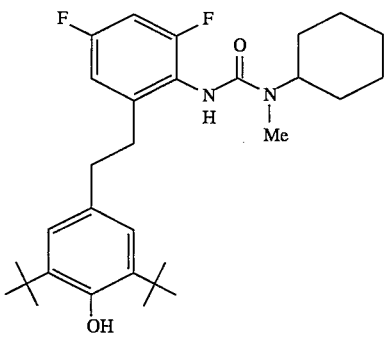

The title compound was prepared in a similar manner to that mentioned in Example 108, using N-methylcyclohexylamine instead of 4-amino-1-benzylpiperidine.

$^1$H-NMR($\delta$ ppm, CDCl$_3$) 6.70–6.80(m, 2H), 6.79(s, 2H), 5.09(s, 1H), 4.98(bs, 1H), 4.00–4.10(m, 1H), 2.75–2.90(m, 4H), 2.60(s, 3H), 1.60–1.80(m, 4H), 1.20–1.50(m, 24H)

IR(cm$^{-1}$) 3630, 3420, 2930, 1639, 1499, 1435, 1317, 1237, 1119

EXAMPLE 195

N-[2-(3,5-di-tert-butyl-4-hydroxyphenethyl)-4,6-difluorophenyl]-N'-[2-(3,4-dichlorophenyl)-2-methylpropyl]urea

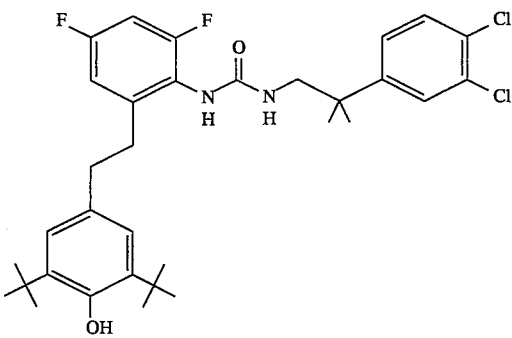

The title compound was prepared in a similar manner to that mentioned in Example 108, using 3,4-dichloro-$\beta,\beta$-dimethylphenethylamine instead of 4-amino-1-benzylpiperidine. m.p. 159°–160° C.

$^1$H-NMR($\delta$ ppm, CDCl$_3$) 7.05–7.30(m, 3H), 6.65–6.78(m, 4H), 5.08–5.11(m, 1H), 4.27(bs, 1H), 3.72(bt, J=6 Hz, 1H), 3.28–3.31(m, 2H), 2.65–2.80(m, 4H), 1.30–1.40(m, 18H), 1.20–1.30(m, 6H)

IR(cm$^{-1}$) 3640, 3310, 2958, 1638, 1566, 1436, 1235, 1118

EXAMPLE 196

N-[2-(3,5-di-tert-butyl-4-hydroxyphenethyl)-4,6-difluorophenyl]-N'-(1-adamantyl)urea

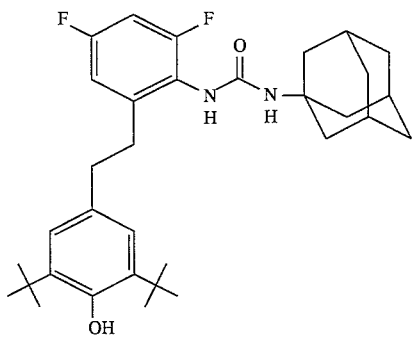

The title compound was prepared in a similar manner to that mentioned in Example 108, using 1-adamantanamine instead of 4-amino-1-benzylpiperidine.

m.p. 218°–220° C.

$^1$H-NMR($\delta$ ppm, CDCl$_3$) 6.81(s, 2H), 6.70–6.80(m, 2H), 5.12(s, 1H), 4.60(bs, 1H), 3.93(bs, 1H), 2.88(t, J=7 Hz, 2H), 2.78(t, J=7 Hz, 2H), 2.03(bs, 3H), 1.91(d, J=3 Hz, 6H), 1.64(bs, 6H), 1.40(s, 18H)

IR(cm$^{-1}$) 3642, 3375, 2910, 1650, 1562, 1495, 1436, 1235, 1120

EXAMPLE 197

N-[2-(3,5-di-tert-butyl-4-hydroxyphenethyl)-4,6-difluorophenyl]-N'-[2-(3,4-dichlorophenyl)-2-methylpropyl]-N'-methylurea

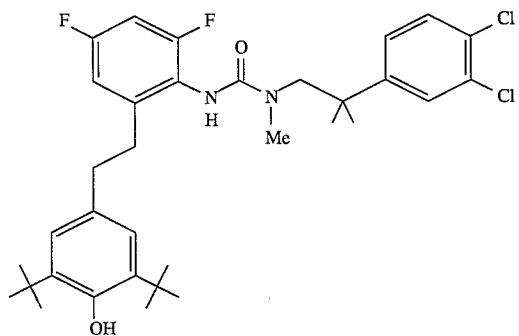

The title compound was prepared in a similar manner to that mentioned in Example 108, using N-methyl-3,4-dichloro-β,β-dimethylphenethylamine instead of 4-amino-1-benzylpiperidine. m.p. 145°–147° C.

$^1$H-NMR($\delta$ ppm, CDCl$_3$) 7.15–7.40(m, 3H), 6.65–6.80(m, 4H), 5.04–5.06(m, 1H), 4.70–4.73(m, 1H), 3.46–3.49(m, 2H), 2.75–2.85(m, 4H), 2.20–2.24(m, 3H), 1.30–1.34(m, 24H)

IR(cm$^{-1}$) 3572, 3420, 2954, 1665, 1505, 1434, 1120

EXAMPLE 198

(R)-N-[2-(3,5-di-tert-butyl-4-hydroxyphenethyl)-4,6-difluorophenyl]-N'-(α-ethoxycarbonylbenzyl)urea

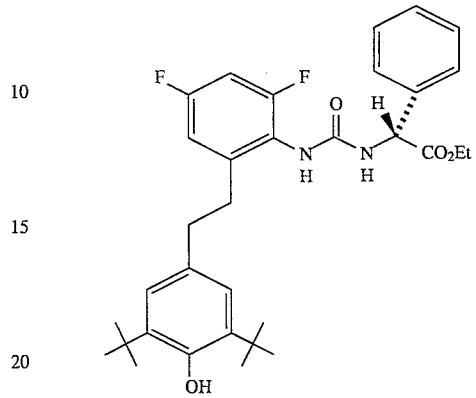

The title compound was prepared in a similar manner to that mentioned in Example 108, using (R)-α-phenylglycine ethyl ester instead of 4-amino-1-benzylpiperidine. m.p. 162°–164° C.

$^1$H-NMR($\delta$ ppm, CDCl$_3$) 7.26–7.32(m, 5H), 6.73–6.80(m, 4H), 5.45(d, J=7 Hz, 1H), 5.22(bd, J=7 Hz, 1H), 5.12(s, 1H), 4.68(bs, 1H), 4.08–4.20(m, 2H), 2.72–2.89(m, 4H), 1.37(s, 18H), 1.18(t, J=7 Hz, 3H)

IR(cm$^{-1}$) 3640, 3350, 2956, 1737, 1641, 1561, 1438, 1122

EXAMPLE 199

N-[2-(3,5-di-tert-butyl-4-hydroxyphenethyl)-4,6-difluorophenyl]-N'-[2-(3,4-dichlorophenyl)-2-propyl]urea

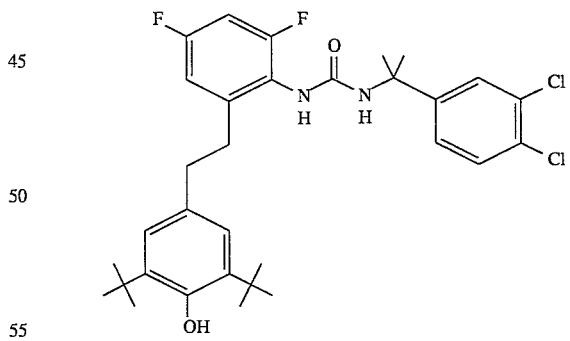

The title compound was prepared in a similar manner to that mentioned in Example 108, using 3,4-dichloro-α,α-dimethylbenzylamine instead of 4-amino-1-benzylpiperidine. m.p. 224°–226° C.

$^1$H-NMR($\delta$ ppm, CDCl$_3$) 7.42(d, J=2 Hz, 1H), 7.31(d, J=9 Hz, 1H), 7.18(dd, J=9, 2 Hz, 1H), 6.75–6.80(m, 4H), 5.13(s, 1H), 4.62(bs, 1H), 4.53(bs, 1H), 2.56(t, J=7 Hz, 2H), 2.77(t, J=7 Hz, 2H), 1.57(s, 6H), 1.40(s, 18H)

IR(cm$^{-1}$) 3634, 3354, 2954, 1649, 1562, 1435, 1277, 1238, 1122

EXAMPLE 200

1-[N-[2-(3,5-di-tert-butyl-4-hydroxyphenethyl)-4,6-difluorophenyl]carbamoyl]-4-benzylpiperidine

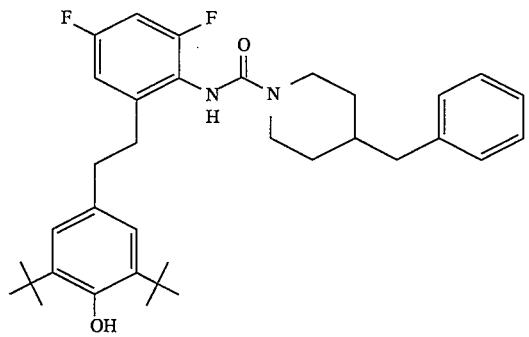

The title compound was prepared in a similar manner to that mentioned in Example 108, using 4-benzylpiperidine instead of 4-amino-1-benzylpiperidine.

$^1$H-NMR($\delta$ ppm, CDCl$_3$) 7.25–7.31(m, 2H), 7.20(t, J=7 Hz, 1H), 7.12(d, J=7 Hz, 2H), 6.71–6.80(m, 2H), 6.75(s, 2H), 5.09(s, 1H), 4.96(s, 1H), 3.73(bd, J=13 Hz, 2H), 2.78–2.85(m, 4H), 2.67(t, J=12 Hz, 2H), 2.53(d, J=7 Hz, 2H), 1.58–1.71(m, 3H), 1.36(s, 18H), 1.12–1.22(m, 2H)

IR(cm$^{-1}$) 3636, 3418, 3026, 1627, 1499, 1435, 1235, 1120, 789, 748, 700

EXAMPLE 201

N-[2-(3,5-di-tert-butyl-4-hydroxyphenethyl)-4,6-difluorophenyl]-N'-[1-(4-dimethylaminophenyl)cyclopentyl]methylurea

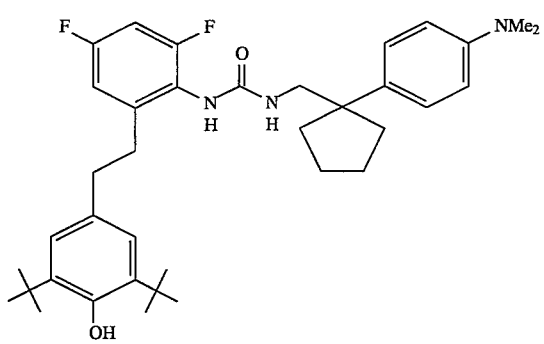

The title compound was prepared in a similar manner to that mentioned in Example 108, using 4-[(1-aminomethyl)-1-cyclopentyl]-N,N-dimethylaniline instead of 4-amino-1-benzylpiperidine. m.p. 165°–166° C.

$^1$H-NMR($\delta$ ppm, CDCl$_3$) 6.92(d, J=9 Hz, 2H), 6.75(s, 2H), 6.68–6.76(m, 2H), 6.54(d, J=9 Hz, 2H), 5.08(s, 1H), 4.59(s, 1H), 3.82(bs, 1H), 3.19(d, J=6 Hz, 2H), 2.89(s, 6H), 2.76(t, J=7 Hz, 2H), 2.67(t, J=7 Hz, 2H), 1.67–1.90(m, 8H), 1.37(s, 18H)

IR(cm$^{-1}$) 3674, 3250, 1615, 1520, 1435, 1233, 1121

EXAMPLE 202

N-[2-(3,5-di-tert-butyl-4-hydroxyphenethyl)-4,6-difluorophenyl]-N'-heptyl-N'-methylurea

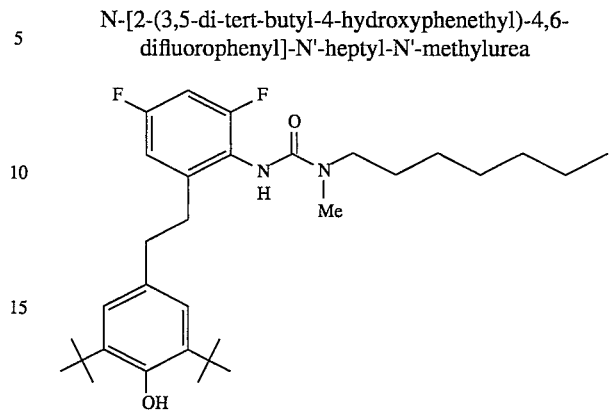

The title compound was prepared in a similar manner to that mentioned in Example 108, using N-methylheptylamine instead of 4-amino-1-benzylpiperidine.

$^1$H-NMR($\delta$ ppm, CDCl$_3$) 6.70–6.80(m, 2H), 6.77(s, 2H), 5.10(s, 1H), 4.96(s, 1H), 3.21(t, J=8 Hz, 2H), 2.75–2.86(m, 4H), 2.75(s, 3H), 1.42–1.56(m, 2H), 1.37(s, 18H), 1.20–1.35(m, 8H), 0.87(t, J=7 Hz, 3H)

IR(cm$^{-1}$) 3640, 3300, 1638, 1503, 1435, 1236, 1120

The preparation of the compound of formula (II) used in each of the above examples is illustrated by the following reference examples.

Reference Example 1

4-(2-Aminophenethyl)-2,6-di-tert-butylphenol (1) 2,6-di-tert-Butyl-4-(2-nitrostyryl)phenol

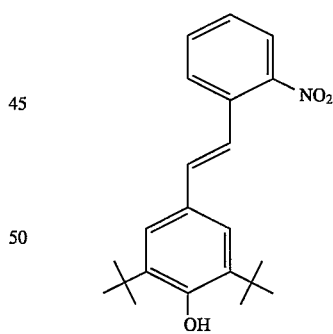

To a solution of 3,5-di-tert-butyl-4-hydroxybenzaldehyde (8.09 g, 34.5 mmol) and 2-nitrophenylacetic acid (9.40 g, 51.9 mmol) in xylene (60 ml) was added piperidine (0.3 ml) and the mixture was heated under reflux for 26 hrs while removing water producing with the progress of reaction. After allowing to stand overnight, hexane was added to afford as crystals 2,6-di-tert-butyl-4-(2-nitrostyryl)phenol (7.67 g, 62.9%).

$^1$H-NMR($\delta$ ppm, CDCl$_3$) 7.94(dd, J=8, 1 Hz, 1H), 7.76(d, J=8 Hz, 1H), 7.57(dd, J=8, 8 Hz, 1H), 7.44(d, J=16 Hz, 1H), 7.33–7.37(m, 3H), 7.07(d, J=16 Hz, 1H), 5.38(s, 1H), 1.48(s, 18H)

117

(2) 4-(2-Aminophenethyl)-2,6-di-tert-butylphenol

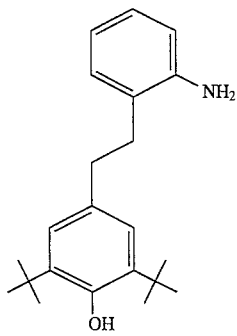

To a suspension of 2,6-di-tert-butyl-4-(2-nitrostyryl)phenol (16.4 g, 23.3 mmol) in ethanol (150 ml) was added a catalytic amount of 10% palladium carbon and the suspension was subjected to catalytic reduction at room temperature at 1–2.5 atms for 8 hrs and at 40° C. for 3 hrs. After filtering the catalyst, distilling off the solvent gave 4-(2-aminophenethyl)-2,6-di-tert-butylphenol (15.1 g, 100%) as a viscous oil.

$^1$H-NMR ($\delta$ ppm, CDCl$_3$) 7.02–7.07(m, 2H), 6.94(s, 2H), 6.74–6.78(m, 1H), 6.67(d, J=8 Hz, 1H), 5.06(s, 1H), 3.3–3.7(bs, 2H), 2.73–2.87(m, 4H), 1.41(s, 18H)

Reference Example 2

(1) 2,6-Diisopropyl-4-(2-nitrostyryl)phenol

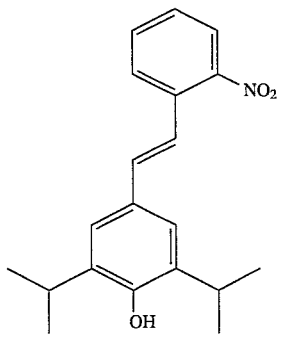

To a solution of 3,5-diisopropyl-4-hydroxybenzaldehyde (0.95 g, 4.6 mmol) and 2-nitrophenyl acetic acid (1.1 g, 6.2 mmol) in xylene (10 ml) was added piperidine (0.05 ml) and the mixture was heated under reflux for 8 hrs while removing water producing with the progress of reaction. After distilling off the solvent followed by purification of the residue by a silica gel column chromatography, recrystallization from hexane gave 2,6-diisopropyl-4-(2-nitrostyryl)phenol (1.3 g, 87%) as crystals.

$^1$H-NMR ($\delta$ ppm, CDCl$_3$) 7.93–7.95(m, 1H), 7.75–7.77(m, 1H), 7.55–7.57(m, 1H), 7.45(d, J=16 Hz, 1H), 7.34–7.38(m, 1H), 7.24(s, 2H), 7.07(d, J=16 Hz, 1H), 4.95(s, 1H), 3.12–3.22(m, 2H), 1.32(s, 6H), 1.30(s, 6H)

118

(2) 4-(2-Aminophenethyl)-2,6-diisopropylphenol

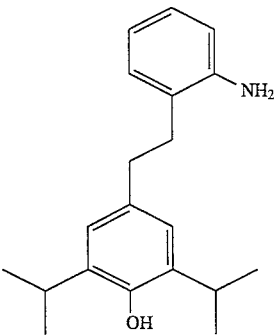

To a suspension of 2,6-diisopropyl-4-(2nitrostyryl)phenol (1.3 g, 4.0 mmol) in ethanol (20 ml) was added a catalytic amount of 10% palladium carbon and the suspension was subjected to catalytic reduction at 1–2.5 atms at room temperature for 7 hrs. After filtering the catalyst, distilling off the solvent gave 4-(2-aminophenethyl)-2,6-diisopropylphenol (1.0 g, 84%) as a viscous oil.

$^1$H-NMR($\delta$ ppm, CDCl$_3$) 7.02–7.06(m, 2H), 6.83(s, 2H), 6.70–6.77(m, 1H), 6.65(d, J=7 Hz, 1H), 4.67(s, 1H), 3.43(bs, 2H), 3.08–3.18(m, 2H), 2.73–2.87(m, 4H), 1.24(s, 6H), 1.22(s, 6H)

Reference Example 3

4-(2-Aminostyryl)-2,6-di-tert-butylphenol

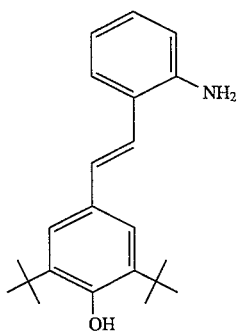

To a solution of 2,6-di-tert-butyl-4-(2-nitrostyryl)phenol (1.1 g, 3.1 mmol) in methanol (15 ml) was added water (4 ml), conc. hydrochloric acid (0.2 ml) and iron powder (1.7 g, 30 mmol) and the mixture was heated under reflux for 5 hrs. After filtration, followed by extraction with ethyl acetate and water, the extract was washed with water, dried over MgSO$_4$ and concentrated. Purification of the residue by a silica gel column chromatography followed by recrystallization from hexane afforded 4-(2-aminostyryl)-2,6-di-tert-butylphenol (0.70 g, 70%).

$^1$H-NMR($\delta$ ppm, CDCl$_3$) 7.36–7.38(m, 1H), 7.34(s, 2H), 7.06–7.10(m, 1H), 6.91–7.10(m, 2H), 6.78–6.82(m, 1H), 6.70–6.72(m, 1H), 5.29(s, 1H), 3.79(s, 2H), 1.47(s, 18H)

Pharmacological Test

1. ACAT inhibitory activity

The enzyme preparation, ACAT was prepared from liver microsme fractions of male rabbits according to the method of E. E. Largis et al. (Journal of Lipid Research, Vol. 30, pages 681–690, 1989). The activity was calculated by assaying the amount of the labelled cholesteryl esters formed from [1-$^{14}$C]oleoyl-CoA and endogenous cholesterol according to the method of Kazuichi NATORI et al. (Japan J. Pharmacol., Vol. 42, pages 517–523, 1986).

The result is shown in Table 1, in which percent inhibition of the formation of the labelled cholesteryl esters with a compound added at $10^{-7}$M is indicated as index for the ACAT inhibitory activity.

The data reveals that the compounds of the invention have a superior ACAT inhibitory activity.

2. Antioxidative activity

Human LDL was incubated in the presence of cupric sulfate ($5\times10^{-6}$M) and in the presence or absence of a compound ($10^{-5}$M) for 5 hrs. After the incubation, the peroxidation of low-density lipoproteins (LDL) is evaluated by the formation of malondialdehyde (MDA), which is a sort of lipid peroxides according to the method of Simon J. T. Mao et al. (J. Med. Chem., Vol. 34, pages 298–302, 1991). Activity of the compound is shown by percent inhibition of the MDA formation as compared with control. The result is shown in Table 1. The data indicates that the compounds of the invention significantly lower the formation of the lipid peroxide (MDA).

3. Cholesterol-lowering activity

Sprague-Dawley male rats were given a powdery feed containing 1% cholesterol and 0.5% cholic acid in an amount of 15 g per day per animal for 3 days to produce hypercholesteremic rats. Four days later, a compound suspended in 0.5% methylcellulose was administered orally at a dose of 30 mg/kg. Blood was drawn prior to and 5 hrs after the administration of the compound, for which the plasma cholesterol level was measured using a commercially available assay kit (Cholesterol E Test Wako, Wako Junyaku K.K.). The result is shown in Table 2.

The data shows that the compounds of the invention significantly reduce blood cholesterol level.

TABLE 1

| Compounds of Example | ACAT Inhibition (%) | Antioxidant Activity (%) |
| --- | --- | --- |
| 1 | 83 | 94 |
| 4 | 95 | 98 |
| 5 | 89 | 100 |
| 6 | 99 | 98 |
| 12 | 91 | 94 |
| 13 | 90 | 92 |
| 14 | 93 | 98 |
| 15 | 76 | 99 |
| 16 | 93 | 95 |
| 17 | 92 | 99 |
| 18 | 97 | 97 |
| 19 | 100 | 94 |
| 29 | 99 | 95 |
| 30 | 84 | 92 |
| 35 | 82 | 94 |
| 38 | 71 | 94 |
| 39 | 88 | 87 |
| 40 | 96 | 98 |
| 41 | 97 | 99 |
| 42 | 95 | 97 |
| 43 | 99 | 99 |
| 44 | 90 | 94 |
| 50 | 88 | 90 |
| 52 | 97 | 94 |
| 57 | 89 | 95 |
| 69 | 96 | 95 |
| 72 | 97 | 97 |
| 74 | 96 | 95 |
| 75 | 88 | 95 |
| 76 | 98 | 96 |
| 77 | 96 | 95 |
| 80 | 92 | 96 |
| 83 | 96 | 96 |

TABLE 1-continued

| Compounds of Example | ACAT Inhibition (%) | Antioxidant Activity (%) |
| --- | --- | --- |
| 85 | 97 | 94 |
| 90 | 92 | 93 |
| 92 | 99 | 96 |
| 97 | 89 | 96 |
| 99 | 100 | 95 |
| 108 | 97 | 93 |
| 114 | 82 | 98 |
| 115 | 87 | 98 |
| 117 | 91 | 97 |
| 124 | 81 | 95 |
| 130 | 99 | 95 |
| 140 | 96 | |
| 141 | 86 | |
| 146 | 85 | |
| 155 | 94 | |
| 159 | 97 | |
| 163 | 81 | |
| 165 | 99 | |
| 166 | 100 | |
| 167 | 100 | |
| 168 | 93 | |
| 173 | 95 | |
| 177 | 98 | |
| 183 | 91 | |

TABLE 2

| Compound of Example | Percent Reduction of Cholesterol (%) |
| --- | --- |
| 35 | 48.4 |
| 83 | 44.6 |
| 92 | 79.9 |
| 105 | 45.9 |
| 108 | 71.8 |
| 130 | 71.5 |

The pharmaceutical preparations comprising the compounds of the invention are prepared by conventional method in accordance with the following formulations.

| Tablets (per tablet) | |
| --- | --- |
| Compound of Example 6 | 50 mg |
| Hydroxypropylcellulose | 2 mg |
| Corn starch | 10 mg |
| Lactose | 100 mg |
| Magnesium stearate | 3 mg |
| Talc | 3 mg |
| Capsules (per capsule) | |
| Compound of Example 17 | 200 mg |
| Starch | 8 mg |
| Microcrystalline cellulose | 23 mg |
| Talc | 8 mg |
| Magnesium stearate | 5 mg |
| Granules (per divided packet) | |
| Coumpound of Example 41 | 1 mg |
| Lactose | 99 mg |
| Corn starch | 50 mg |
| Crystalline cellulose | 50 mg |
| Hydroxypropylcellulose | 10 mg |
| Ethanol | 9 mg |

What is claimed is:

1. A compound of formula (I) or a pharmaceutically acceptable salt thereof

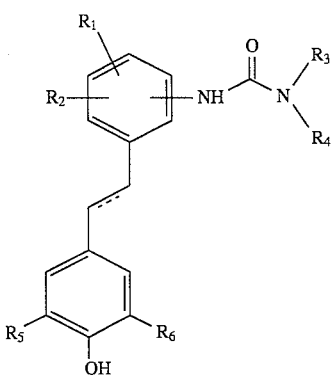 (I)

in which:
R$_1$ and R$_2$, which may be the same or different, each represents
a hydrogen atom,
a halogen atom,
a straight or branched (C$_1$–C$_6$)alkyl group or
a straight or branched (C$_1$–C$_6$)alkoxy group,
R$_3$ and R$_4$, which may be the same or different, each represents
a hydrogen atom,
a straight or branched (C$_1$–C$_{12}$)alkyl group,
a straight or branched (C$_2$–C$_{20}$)alkenyl group,
a (C$_1$–C$_6$)alkoxy(C$_1$–C$_6$)alkyl group,
a (C$_1$–C$_6$)alkoxycarbonyl (C$_1$–C$_9$)alkyl group,
a benzyloxycarbonyl(C$_1$–C$_6$)alkyl group in which the alkyl moiety is optionally substituted by phenyl,
a N,N-di(C$_1$–C$_6$)alkylamino(C$_1$–C$_6$)alkyl group,
a N-(C$_1$–C$_6$)alkyl-N-benzylamino(C$_1$–C$_6$)alkyl group,
a (C$_1$–C$_6$)alkylthio(C$_1$–C$_6$)alkyl group,
an oxo(C$_1$–C$_9$)alkyl group,
a hydroxy(C$_1$–C$_6$)alkyl group,
a dihydroxy(C$_1$–C$_6$)alkyl group,
a cyclo(C$_3$–C$_{15}$)alkyl group,
a cyclo(C$_3$–C$_8$)alkyl(C$_1$–C$_6$)alkyl group,
a dicyclo(C$_3$–C$_9$)alkyl(C$_1$–C$_6$)alkyl group,
a bicyclo(C$_6$–C$_9$)alkyl group,
a tricyclo(C$_9$–C$_{12}$)alkyl group,
in which in all cases the cycloalkyl group or the cycloalkyl moiety is optionally substituted by one or two substituents selected from the group consisting of (C$_1$–C$_6$)alkyl, hydroxy, amino, acetoxy, acetamido, phenyl, benzyloxy, dimethylaminophenyl, and methylenedioxyphenyl, which may be further fused with a benzene ring,
an aryl group,
an aryl(C$_1$–C$_6$)alkyl group,
a diaryl(C$_1$–C$_6$)alkyl group,
in which in all cases the aryl group or the aryl moiety is optionally substituted by one, two or three substituents selected from the group consisting of (C$_1$–C$_6$)alkyl, (C$_1$–C$_6$)alkyloxy, halogen, nitro, hydroxy, amino, dimethylamino, methylenedioxy, and pyrrolidinyl,
a heterocyclic group or
a heterocyclic group attached to a (C$_1$–C$_6$)alkylene chain,
in which in all cases the heterocyclic group represents a saturated or unsaturated, 5 to 8 membered ring monocyclic or bicyclic, heterocyclic group containing 1 to 3 heteroatoms selected from the group consisting of S, O and N, and the heterocyclic group is optionally substituted by one or two substituents selected from the group consisting of acetyl, hydroxy, (C$_1$–C$_9$)alkyl, (C$_1$–C$_9$)alkyloxy, cyclo(C$_3$–C$_8$)alkyl, cyclo(C$_3$–C$_9$)alkyl(C$_3$–C$_{10}$)alkyl, pyridyl(C$_1$–C$_6$)alkyl, phenyl, phenyl(C$_1$–C$_6$)alkyl, diphenyl (C$_1$–C$_6$)alkyl, and phenylpiperazinyl, the phenyl group or the phenyl moiety being optionally substituted by one or two substituents selected from the group consisting of halogen, hydroxy, (C$_1$–C$_6$)alkyl, (C$_1$–C$_6$)alkoxy, cyano, diethylamino and trifluoromethyl, which may be further fused with a benzene ring, and further R$_3$ and R$_4$, together with the nitrogen atom to which they are attached, may form a saturated or unsaturated heterocyclic group,
in which the heterocyclic group represents a 5 to 8 membered ring monocyclic or bicyclic, heterocyclic group or a group derived from a heterocyclic spiro compound, which may contain one or two heteroatoms selected from the group consisting of S, O or N, the heterocyclic group being optionally substituted by one or two substituents selected from the group consisting of (C$_1$–C$_6$)alkyl, hydroxy, hydroxy(C$_1$–C$_6$)alkyl, (C$_1$–C$_6$)alkoxy(C$_1$–C$_6$)alkyl, acetoxy(C$_1$–C$_6$)alkyl, (C$_1$–C$_9$)alkylcarbonyl, (C$_1$–C$_6$)alkoxycarbonyl, amino, tosyl, phenyl, halogenophenyl, (C$_1$–C$_6$)alkoxyphenyl, phenyl(C$_1$–C$_6$)alkyl, benzyloxy, benzyloxy(C$_1$–C$_6$)alkyl, tolyl, xylyl, benzoyl, methylenedioxyphenyl(C$_1$–C$_6$)alkyl, pyridyl, pyridylcarbonyl, piperidyl, pyrrolidinyl (C$_1$–C$_6$)alkyl and pyrrolidinylcarbonyl(C$_1$–C$_6$)alkyl, which may be further fused with a benzene ring,
in which in all cases the alkyl and alkoxy moieties may be either straight or branched,
with the proviso that both R$_3$ and R$_4$ do not represent a hydrogen atom at the same time;
R$_5$ and R$_6$, which may be the same or different, each represents a straight or branched (C$_1$–C$_6$)alkyl group; and the line

represents —CH$_2$CH$_2$— or —CH=CH—.

2. A compound of claim 1 wherein R$_3$ and R$_4$, which may be the same or different, each represents
a hydrogen atom,
a straight or branched (C$_1$–C$_{10}$)alkyl group,
a straight or branched (C$_3$–C$_{17}$)alkenyl group,
a (C$_1$–C$_4$)alkoxy(C$_1$–C$_4$)alkyl group,
a (C$_1$–C$_4$)alkoxycarbonyl(C$_1$–C$_4$)alkyl group,
a benzyloxycarbonyl(C$_1$–C$_4$)alkyl group in which the alkyl moiety is optionally substituted by phenyl,
a (C$_1$–C$_4$)alkylthio(C$_1$–C$_4$)alkyl group, a cyclo(C$_3$–C$_{12}$)alkyl group or a cyclo(C$_5$–C$_7$)alkyl(C$_1$–C$_4$)alkyl group in which the cycloalkyl group or the cycloalkyl moiety is optionally monosubstituted by a substituent selected from the group consisting of (C$_1$–C$_4$)alkyl, hydroxy, amino, acetoxy, acetamide, phenyl, benzyloxy, dimethylaminophenyl and methylenedioxyphenyl, or the cycloalkyl group or the cycloalkyl moiety is optionally fused with a benzene ring; a dicyclohexyl($C_1$–$C_4$)alkyl group, a bicyclooctyl group, an adamantyl group, a phenyl group optionally substituted by ($C_1$–$C_4$)alkyl or hexyloxy, a naphthyl group, an anthryl group, a phenyl($C_1$–$C_4$)alkyl group in which the phenyl moiety is optionally substituted by one or two substituents selected from the group consisting of ($C_1$–$C_4$)alkyl, ($C_1$–$C_4$)alkyloxy, halogen, nitro, hydroxy, amino, dimethylamino, methylenedioxy and pyrrolidinyl;

a diphenyl($C_1$–$C_4$)alkyl group, a heterocyclic group or a heterocyclic group attached to a ($C_1$–$C_4$)alkylene chain in which the heterocyclic group represents a saturated or unsaturated, 5 or 6 membered ring monocyclic or bicyclic, heterocyclic group containing 1 or 2 nitrogen atoms and the heterocyclic group is optionally substituted by one or two substituents selected from the group consisting of acetyl, hydroxy, ($C_1$–$C_6$)alkyl, cyclohexyl, pyridyl($C_1$–$C_4$)alkyl, phenyl($C_1$–$C_4$)alkyl or diphenyl($C_1$–$C_4$)alkyl in which the phenyl moiety is optionally substituted by one or two substituents selected from the group consisting of halogen, ($C_1$–$C_4$)alkyl, ($C_1$–$C_4$)alkoxy, cyano, diethylamino and trifluoromethyl, and phenylpiperazinyl, which may be further fused with a benzene ring;

and further $R_3$ and $R_4$, together with the nitrogen atom to which they are attached may form a saturated or unsaturated heterocyclic ring, in which the heterocyclic group represents a 5 to 7 membered ring monocyclic or bicyclic, heterocyclic group or a group derived from a heterocyclic spiro compound, which contain one or two nitrogen atoms, the heterocyclic group being optionally substituted by one or two substituents selected from the group consisting of ($C_1$–$C_4$)alkyl, hydroxy($C_1$–$C_4$)alkyl, acetoxy($C_1$–$C_4$)alkyl, ($C_1$–$C_6$)alkylcarbonyl, ($C_1$–$C_4$)alkoxycarbonyl, tosyl, phenyl, phenyl($C_1$–$C_4$)alkyl, benzyloxy, benzyloxy($C_1$–$C_4$)alkyl, benzoyl, methylenedioxyphenyl($C_1$–$C_4$)alkyl, pyridylcarbonyl, piperidyl and pyrrolidinylcarbonyl($C_1$–$C_4$)alkyl.

3. A compound of claim 2 wherein $R_3$ and $R_4$, which may be the same or different, each represents a hydrogen atom, a straight or branched ($C_1$–$C_7$)alkyl group, a cyclo($C_4$–$C_8$)alkyl group, a heterocyclic group or a heterocyclic group attached to a ($C_1$–$C_4$)alkylene chain in which the heterocyclic group represents a saturated or unsaturated, 5 or 6 membered ring monocyclic or bicyclic, heterocyclic group containing one nitrogen atom and the heterocyclic group is optionally substituted by one or two substituents selected from the group consisting of methyl, ethyl, cyclohexyl, pyridylmethyl, and phenyl($C_1$–$C_3$)alkyl in which the phenyl moiety being optionally substituted by one or two substituents selected from the group consisting of halogen, methoxy, cyano, dimethylamino and trifluoromethyl, which may be further fused with a benzene ring.

4. A compound of claim 3 wherein $R_3$ and $R_4$, which may be the same or different, each represents a hydrogen atom, a straight or branched ($C_1$–$C_4$)alkyl group, cyclohexyl, cycloheptyl, pyrrolidinyl or piperidyl, the latter two heterocyclic groups being optionally substituted by one or two substituents selected from the group consisting of methyl, ethyl, cyclohexyl, pyridylmethyl, and phenyl($C_1$–$C_3$)alkyl in which the phenyl moiety being optionally substituted by one or two substituents selected from the group consisting of halogen, methoxy, cyano, diethylamino and trifluoromethyl, which may be further fused with a benzene ring.

5. A compound of claim 2 wherein $R_3$ and $R_4$, together with the nitrogen atom to which they are attached, may form a saturated or unsaturated heterocyclic ring, in which the heterocyclic group represents a 5 or 6 membered ring monocyclic or bicyclic, heterocyclic group which contain one or two nitrogen atoms, the heterocyclic group being optionally substituted by one or two substituents selected from the group consisting of methyl, hydroxyethyl, acetoxyethyl, pentylcarbonyl, ethoxycarbonyl, tosyl, phenyl, benzyl, benzyloxy, benzyloxyethyl, benzoyl, methylenedioxybenzyl, pyridylcarbonyl and piperidyl, which may be further fused with a benzene ring.

6. An ACAT inhibitor comprising a compound of claim 1 or a pharmaceutically acceptable salt thereof.

7. A pharmaceutical composition comprising as an active ingredient a compound of claim 1 or a pharmaceutically acceptable salt thereof and a pharmaceutically acceptable carrier and/or excipient.

8. A pharmaceutical composition of claim 7 for use in the prophylaxis and treatment of hypercholesterolemia and atherosclerosis.

* * * * *